(12) United States Patent
Malackowski et al.

(10) Patent No.: US 8,285,363 B2
(45) Date of Patent: Oct. 9, 2012

(54) SURGICAL TRACKER AND IMPLANTABLE MARKER FOR USE AS PART OF A SURGICAL NAVIGATION SYSTEM

(75) Inventors: Donald W. Malackowski, Schoolcraft, MI (US); Chunwu Wu, Kalamazoo, MI (US); Robert Brindley, Delton, MI (US); Paul M. Hoekstra, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 681 days.

(21) Appl. No.: 12/174,914

(22) Filed: Jul. 17, 2008

(65) Prior Publication Data

US 2008/0312530 A1    Dec. 18, 2008

Related U.S. Application Data

(63) Continuation of application No. PCT/US2007/060573, filed on Jan. 16, 2007.

(51) Int. Cl.
*A61B 5/05* (2006.01)
(52) U.S. Cl. .......................... 600/424; 600/476; 600/473
(58) Field of Classification Search .................. 600/407, 600/424, 476, 473; 606/130
See application file for complete search history.

(56) References Cited

U.S. PATENT DOCUMENTS

| | | | |
|---|---|---|---|
| 5,394,457 A | 2/1995 | Leibinger et al. | |
| 5,465,041 A * | 11/1995 | Sanders et al. | 323/312 |
| 5,891,034 A | 4/1999 | Bucholz | |
| 5,902,238 A * | 5/1999 | Golden et al. | 600/424 |
| 5,944,663 A | 8/1999 | Kuth et al. | |
| 6,017,354 A | 1/2000 | Culp et al. | |
| 6,026,315 A | 2/2000 | Lenz et al. | |
| 6,172,499 B1 * | 1/2001 | Ashe | 324/207.12 |
| 6,235,038 B1 * | 5/2001 | Hunter et al. | 606/130 |
| 6,402,762 B2 | 6/2002 | Hunter et al. | |
| 6,405,072 B1 | 6/2002 | Cosman | |
| 7,422,582 B2 | 9/2008 | Malackowski et al. | |
| 2001/0011175 A1 | 8/2001 | Hunter et al. | |
| 2002/0193685 A1 | 12/2002 | Mate et al. | |
| 2003/0004411 A1 | 1/2003 | Govari et al. | |
| 2003/0052785 A1 | 3/2003 | Gisselberg et al. | |
| 2004/0125916 A1 | 7/2004 | Herron et al. | |
| 2006/0004286 A1 * | 1/2006 | Chang et al. | 600/435 |
| 2006/0264732 A1 | 11/2006 | Wu | |
| 2007/0085496 A1 | 4/2007 | Philipp et al. | |
| 2008/0269596 A1 * | 10/2008 | Revie et al. | 600/424 |

FOREIGN PATENT DOCUMENTS

WO    2005/087125 A2    9/2005

OTHER PUBLICATIONS

PCT App. No. PCT/US2007/060573, EPO Partial Search Report, May 2007.

* cited by examiner

*Primary Examiner* — Brian Casler
*Assistant Examiner* — Christopher Cook

(57) ABSTRACT

A marker for use with a surgical navigation system for tracking the tissue with which the marker is associated. The overall dimensions of the mark is such that it is shaped to be disposed below the skin of the patient in which the marker is implanted. The marker has a stem or a spike that allows the marker to be implanted in hard tissue such as bone. A head, containing navigation system components is located above the stem or spike. Once the procedure is completed the marker is removed from the patient by breaking the head free from the stem Alternatively the head may be rotated to cause the whole of the marker to break free from the bone in which the marker is implanted.

20 Claims, 40 Drawing Sheets

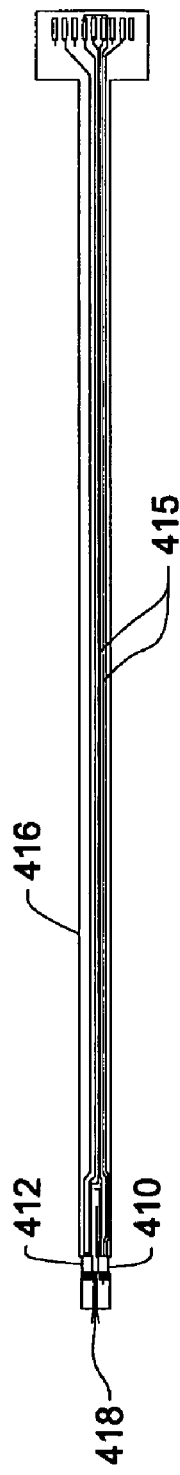
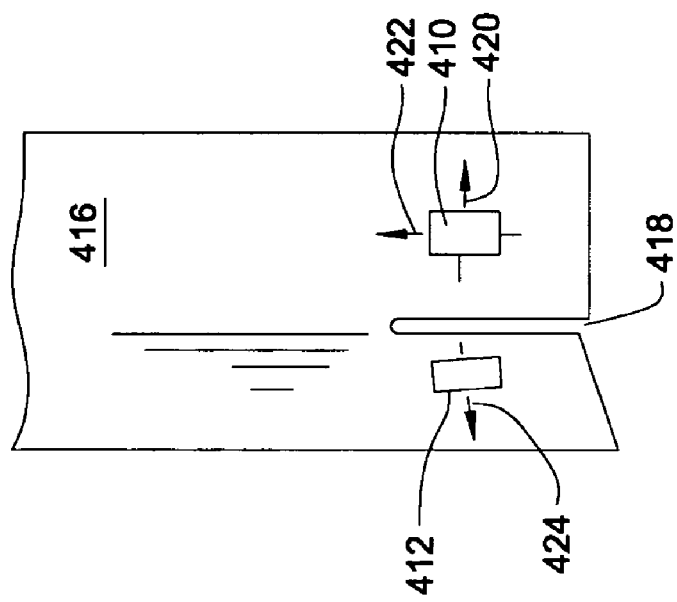
FIG. 19
FIG. 20

498 ↘

| MARKER IDENTIFICATION | 540 |
| MARKER AUTHORIZATION | 542 |
| MARKER USER HISTORY | 544 |
| EFF. COEFS. TRANSDUCER 1 | 546 |
| EFF. COEFS. TRANSDUCER 2 | 548 |
| EFF. COEFS. TRANSDUCER 3 | 550 |

FIG. 28

SURGICAL TRACKER AND IMPLANTABLE MARKER FOR USE AS PART OF A SURGICAL NAVIGATION SYSTEM

RELATIONSHIPS TO EARLIER FILED APPLICATIONS

This application is a continuation of PCT App. No. PCT/US2007/060573 filed 16 Jan. 2007 which claims priority from U.S. patent application Ser. No. 11/333,558 filed 17 Jan. 2006, now abandoned. Both PCT App. No. PCT/US2007/060573 and U.S. patent application Ser. No. 11/333,558 are explicitly incorporated herein by reference.

FIELD OF THE INVENTION

This invention relates generally to a surgical navigation system used to track the position of body tissue. More particularly, this invention relates to a surgical navigation for tracking body tissue that does not expose the tissue to excessive trauma and that can be used in the presence of ferromagnetic objects.

BACKGROUND OF THE INVENTION

Surgical navigation systems are increasingly used as aids in surgical procedures. Generally, a surgical navigation includes a tracker, a localizer and a processor. The tracker is attached to an instrument or section of tissue the position of which is to be tracked. The localizer, relative to the tracker, is static. One or more transmitters are contained in either the tracker or localizer. The other of the localizer or the tracker contains one or more complementary receivers able to detect the energy emitted by the transmitters. It is known to construct surgical navigation systems out of transmitter receiver pairs wherein the transmitted energy is photonic energy, (visible light, UV and/or IR), sonic energy, electromagnetic energy or RF energy. The processor receives signals from the receiver(s) indicating the strength of the energy emitted from the transmitter(s) or other position/orientation dependent characteristic. Based on these signals, the processor generates data representative of the position and orientation of the tracker relative to the localizer. By inference, this leads to the position and orientation of the body tissue or instrument to which the localizer is attached. Often this information is presented on a display connected to the processor.

There are a number of reasons why, in a surgical procedure, it is desirable to track the position of body tissue. In an orthopedic surgical procedure, for example, it is desirable to track the position of hard tissue, bone. This tracking is often performed as part of a procedure to replace a joint such as knee, hip or shoulder. Prior to the replacement of the original joint, it is desirable to track the motion of the bones connected by the joint. For example, in a knee replacement procedure, the surgeon will want to know the relative position and range of motion of the below the knee tibia to the above the knee femur. During the actual joint replacement process, this information helps the surgeon fit the replacement joint to the bone so that, post procedure the patient's bones are properly aligned relative to each other and the bones have the appropriate range of motion.

In other surgical procedures, it is useful to know the position of the patient's tissue in order to assist in the placement and/or control of a surgical instrument at or near the surgical site. In this type of procedure, the system tracks the location of the patient's tissue and the surgical instrument. Based on these data, the processor generates a map that indicates the position of the surgical instrument relative to the tissue or an adjacent surgical site. The surgeon, by reference to this map, properly positions the instrument to accomplish the desired surgical task. Some surgical navigation systems are integrated with the units that regulate the actuation of the surgical instrument. Some versions of these integrated systems are constructed so that, based on the map data indicating the position of the surgical instrument relative to the tissue, actuation of the instrument is regulated.

As mentioned above, the tracker-localizer pair of a surgical navigation system exchanges one of a specific form of energy. Many currently available surgical navigation systems are designed so that their trackers emit and localizers receive photonic energy such as infra red light. These systems often typically require trackers that are relatively large in size, surface areas of 4 cm$^2$ or more.

When a tracker is attached to tissue, it must firmly be attached to tissue site it is intended to track. This is because, if the tracker moves relative to the tissue, the system may not generate signals that accurately represent tissue position. Currently, in order to track the position of bone with an IR tracker, the following protocol is employed. A hole is drilled in the bone. A post is fitted into the hole so it is firmly attached to the bone. Often, to accomplish this latter intermediate goal, it is necessary to secure the post to the bone so it extends through the opposed sides of the bone. Once the post is firmly secured in place, the tracker is mounted to an exposed end of the post. Having to so mount the tracker to the bone appreciably adds to the trauma to which the patient is exposed when required to undergo a surgical procedure. This is especially true when, in order to prevent the post from moving, it is necessary to extend the post through the bone.

Moreover, in this type of arrangement, the post and tracker sub-assembly typically extend 10 cm or more above the patient. Given the rather large size of the tracker, this sub assembly, while serving as an important aid in surgery, also functions as an obstruction the surgical personnel have to take care to avoid.

To avoid the above discussed disadvantages of conventional IR surgical navigation systems, there has recently been proposed a system that relies on electromagnetic navigation. This system relies on relatively small fiducial markers designed to be implanted in the bone subcutaneously. Given the relatively small size of these markers, when fitted to the bone, there is no need fit them through the bone. Thus, use of these markers is expected to result in less trauma to the patient and reduced clutter adjacent the surgical site. These markers are intended to exchange EM signals with complementary localizers located adjacent the patient.

While the above proposed system offers some benefits, there are some limitations associated with its use. Specifically, the system introduces into the operating room localizers with relatively large antennas, coils. These structural members are used to both inductively transfer energy to and exchange signals with the components internal to the fiducial markers.

Moreover, the signals exchanged between the fiducial markers and the complementary coils are electromagnetic signals. Thus, the strength and direction of the signals are affected by the presence of ferromagnetic materials in the path between the coils and markers. To ensure a surgical navigation system of this variety generates data that accurately indicates the positions of the fiducial markers, and the bones to which they are attached, it is necessary to ensure that space between the coils and markers are free of ferromagnetic materials or other objects that can distort the transmission of the EM energy. This may mean, for example, that instruments formed with ferromagnetic materials should not be introduced into the space during the tracking process. Such instruments include, but are not limited to, powered surgical tools with energized stators. This requirement limits the utility of this system.

SUMMARY OF THE INVENTION

This invention is related to a new and useful hybrid surgical navigation system for tracking the position of body tissue. The system and method of this invention are designed to minimize trauma to the tissue it is used to track and can be used without appreciably limiting the introduction of ferromagnetic devices into the surgical field.

The hybrid surgical navigation system of this invention includes two independent navigation systems. A first navigation system includes a tracker head designed to be loosely fitted over the body adjacent the internal tissue the position of which is to be tracked. In one version of the invention, the tracker contains one or more transmitters that emit energy that can pass into the tissue without distortion. In one form of the invention, the transmitters emit EM or RF energy.

The first navigation system also includes a tissue marker positioned subcutaneously at the tissue to be tracked. The tissue marker is formed with a structural member(s) that hold(s) the marker to the tissue so the two move in unison. Internal to the tissue marker are transducers. The transducers are sensitive to the energy emitted by the tracker head transmitters. Also internal to the tissue marker is a transmitter that outputs signals representative of the strengths of the signals detected by the transducers.

The second navigation system of the hybrid system of this invention is located wholly outside of the patient. The second system includes a localizer. In one embodiment of the invention, the localizer contains transducers sensitive to IR light. The second navigation system also contains a number of IR transmitting LEDs. These LEDs are mounted to the tracker head.

The hybrid navigation system of this invention also includes a processor. The processor receives as input data representative of the signals measured by the tissue marker. Based on these data, the processor determines the location and orientation of the tissue marker relative to the tracker head. The processor also receives input data signals representative of the light sensed by the localizer. Based on these data, the processor determines the location and orientation of the tracker head relative to the localizer. Based on these intermediate-generated data, the processor using transformation algorithms, generates data indicating the position and orientation of the tissue marker and, therefore, the tissue, relative to the localizer. These data are then provided to the surgical personnel.

In the system of this invention, the tracker head and tissue marker are separated by distances of 15 cm or less. Therefore, the signals exchanged between the tracker head and tissue marker are of relatively low strength. This makes it possible to provide a tracker head that is small in size. Consequently, only a minimal incision is needed to fit the marker. Further, only low strength energy needs to be transmitted transcutaneously, through the body. These features collectively minimize the trauma to which the patient's body is exposed when the system and method of this invention is employed.

Still another feature of the low power requirement of this invention is that a battery is typically all that is required to power the tracker. Therefore, the need to introduce an addition power cord near the patient is eliminated Further there is only a relatively small space between the tissue marker and the tracker. This means a ferromagnetic object may be placed relatively close to the components of this system without adversely affecting the accuracy of the tracker position and orientation data generated by the system.

BRIEF DESCRIPTION OF THE DRAWINGS

This invention is pointed out with particularity in the claims. The above and further features and benefits of the system and method of this invention are better understood by reference to the following Detailed Description taken in conjunction with the accompanying drawings in which:

FIG. 19 is a plan view illustrating how EM sensors, such as magnetoresisitive sensors are mounted on a flex circuit according to this invention;

FIG. 20 is a perspective view illustrating how the distal end of the assembly of FIG. 19 is shaped so that the sensors are able to monitor the EM signals present along the three mutually orthogonal axes;

FIG. 28 is a block diagram representing the type of data stored in the memory integrally associated with the third bone marker;

DETAILED DESCRIPTION

I. Basic System

Figure 1:
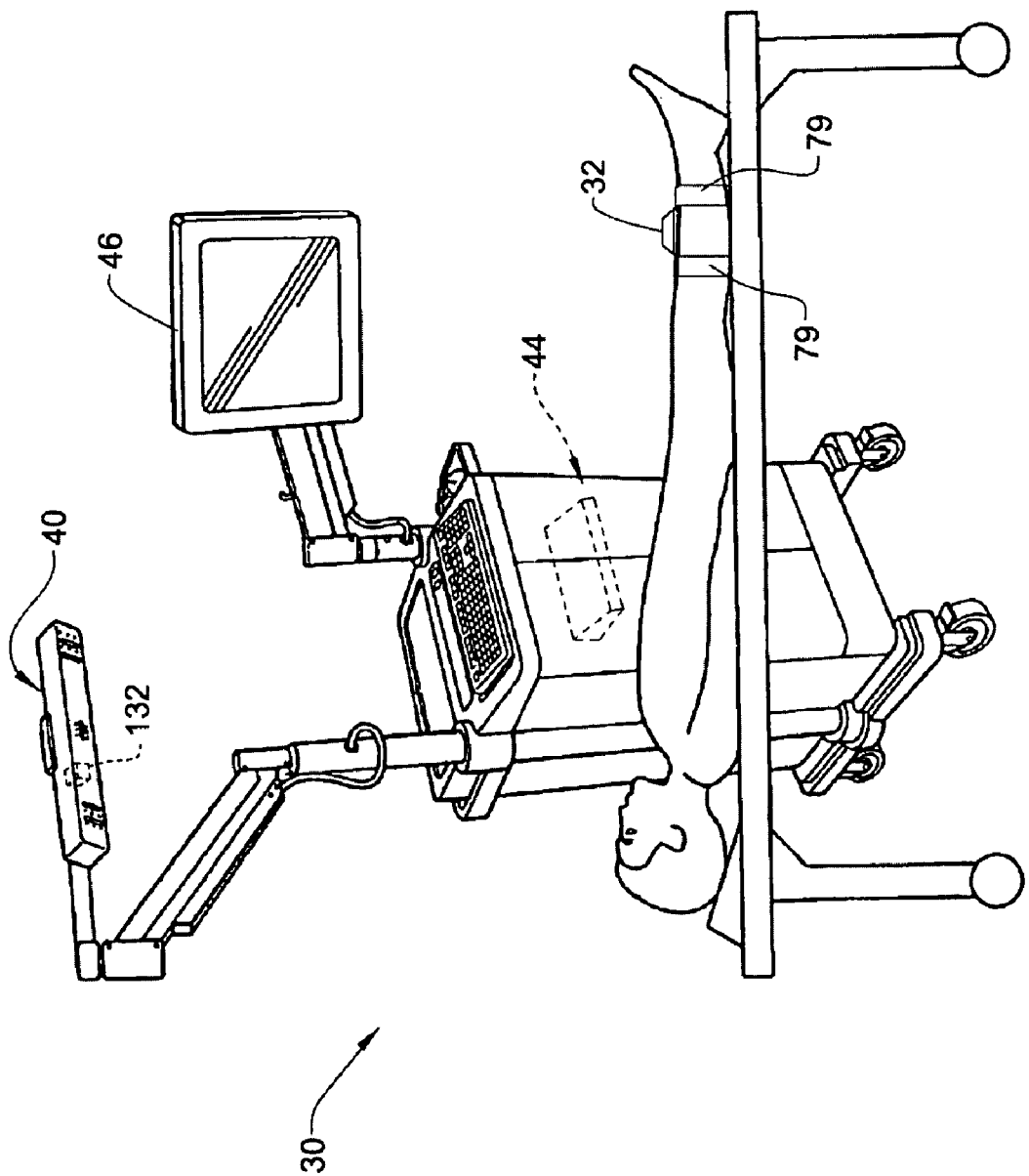
FIG. 1 depicts a hybrid surgical navigation system of this invention.
Figure 2:
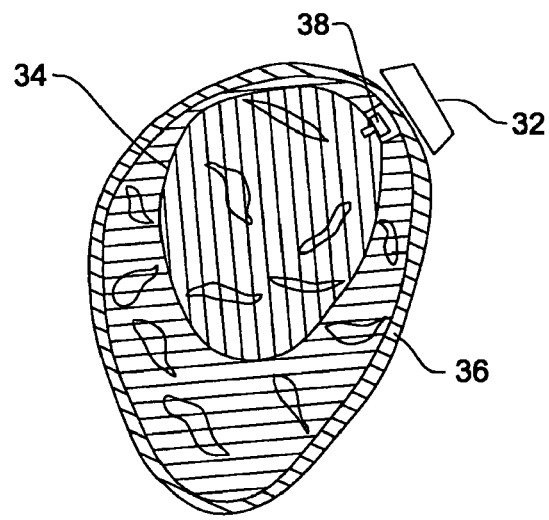
FIG. 2 is a cross sectional view of the relationship between tissue tracked by the system and the components of the system.

FIGS. 1 and 2 provide an overall view of the components of the surgical navigation system 30 of this invention. System 30 includes a tracker 32 that is loosely fitted over the tissue, here the tibia 34, the position of which is to be tracked. Attached to the tibia 34, below the skin 36, is a bone marker 38. Tracker 32 and bone marker 38 contain complementary components of a first navigation system that generate data indicating the position of the bone marker relative to the tracker. Generally, this process occurs by one of the tracker head 32 or bone marker 38 emitting energy; components internal to the other of the bone marker 38 or tracker 32 sense the strength of the emitted energy. Collectively, the tracker 32 and bone marker 34 and their complementary energy transmitting and sensing components comprise the first navigation system.

A localizer 40 often spaced 0.5 m or more and often 1 m or more from tracker head 32 is also part of the system 30. Internal to the tracker head 32 or localizer 40 are components the actively or passively broadcast energy to the other of the localizer or the tracker. Sensors internal to the localizer 40 or tracker 32 to which the energy is broadcast generate signals representative of the strength of the received energy. Generally, this sub-assembly is the second navigation system.

The sensor signals generated by both the first and second navigation systems are forwarded to a processor 44, (shown as phantom rectangle in FIG. 1,) also part of the hybrid system 30. Based on the sensor signals, processor 44 generates data indicating the position and orientation of the bone marker 38. By extension, these data indicate the position and orientation of the bone 34. Often these data are presented to the surgical personnel as an image on a display 46 also part of system 30.

Figure 3:
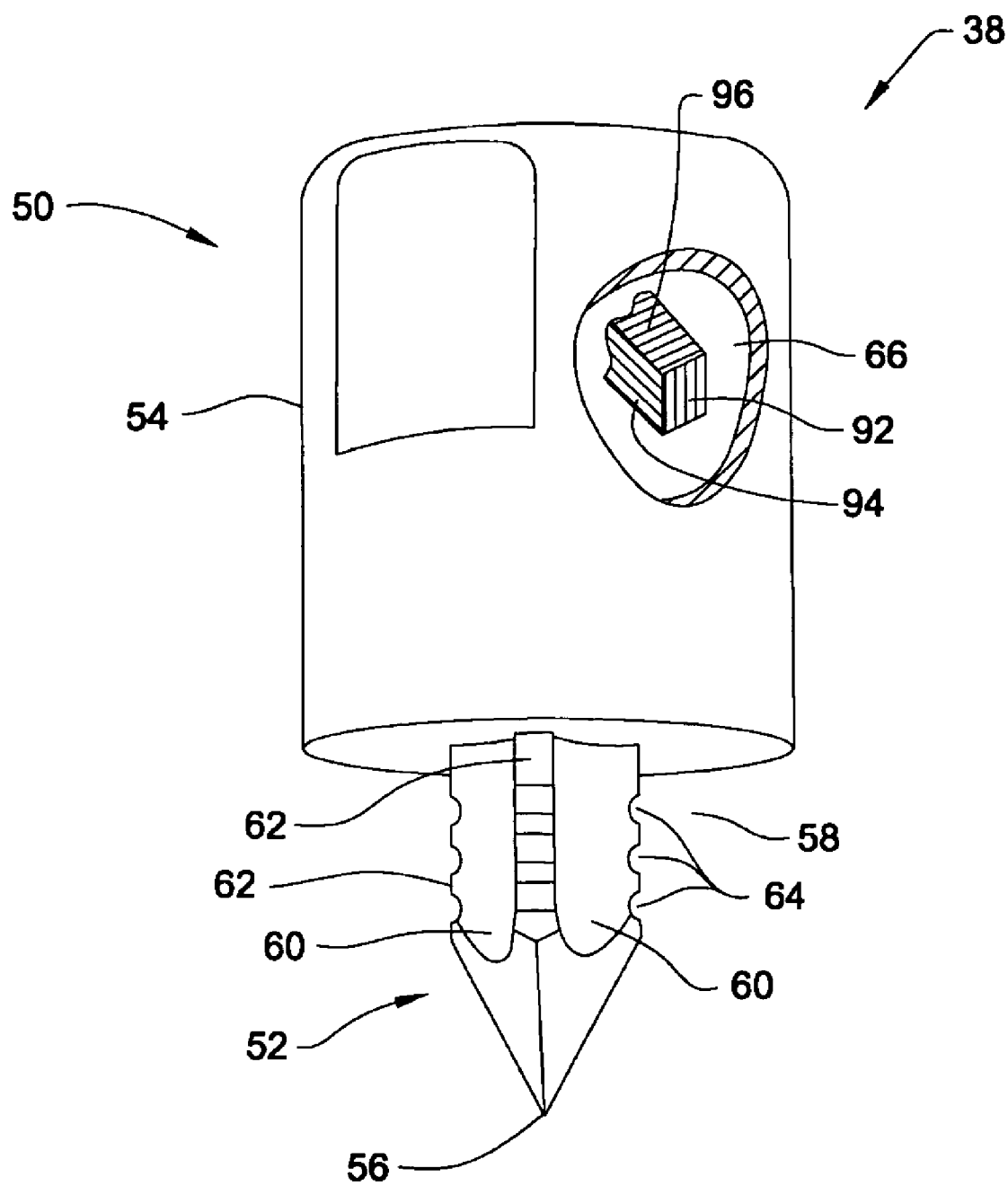
FIG. 3 is a perspective and partially broken away view of a bone marker of this invention.

As best in FIG. 3, bone marker 38 of this invention includes a head 50 from which a stem 52 extends. Head 50 generally has a circular cross sectional profile so as to give the head a generally cylindrical shape. The head is, however, further formed to have to have two diametrically opposed flats 54, (one flat shown). The flats 54 extend downwardly from the top of the head 50. In the illustrated version of the invention flats 54 project approximately 50% along the total length of the head 50. Flats 54 functions as insertion and removal features for the bone marker 38. When an insertion tool is employed to fit the marker 38 or a removal tool is employed to extract the marker, members integral with these tools press against the flats 54 to facilitate marker insertion/retraction, (tools not illustrated).

Stem 52 is shaped to hold the bone marker to the section of the bone to which the marker is fitted. The stem 52 is shaped to have distal end tip 56 that is generally in the shape of a four-sided pyramid. ("Distal" it should be understood means toward the surgical site/away from the surgeon. "Proximal" means away from the surgical site/towards the surgeon.) Between the marker head 50 and tip 56, stem 52 has a base 58. The base is formed to have four concave walls 60 (two walls 60 shown) each of which is aligned with one of the sides of the tip 56. Between each pair of inwardly curved walls 60 there is corner wall 62 (three corner walls 62 shown). Each corner wall 62 is generally flat. However, stem 52 is further shaped so that a number of spaced apart inwardly curved grooves 64 extend laterally across each corner wall 62.

Internal to bone marker head 50 is a transducer 66. Transducer 66 is part of the first tracker system. Transducer 66 is capable of emitting or sensing energy that can be transmitted through tissue without distortion. In some versions of the invention, transducer 66 is capable of either emitting or sensing electromagnetic energy or RF energy.

In some versions of the invention, marker 38 has an overall length from the top of the head 50 to the stem distal end tip 56 of 30 mm or less and, more preferably, 20 mm or less. Head 50 has a length 20 mm or less and, in more preferred versions of the invention, 15 mm or less. Head 50, the largest diameter portion of the marker, has a diameter of 14 mm or less and, more preferably, 7 mm or less.

Figure 4:
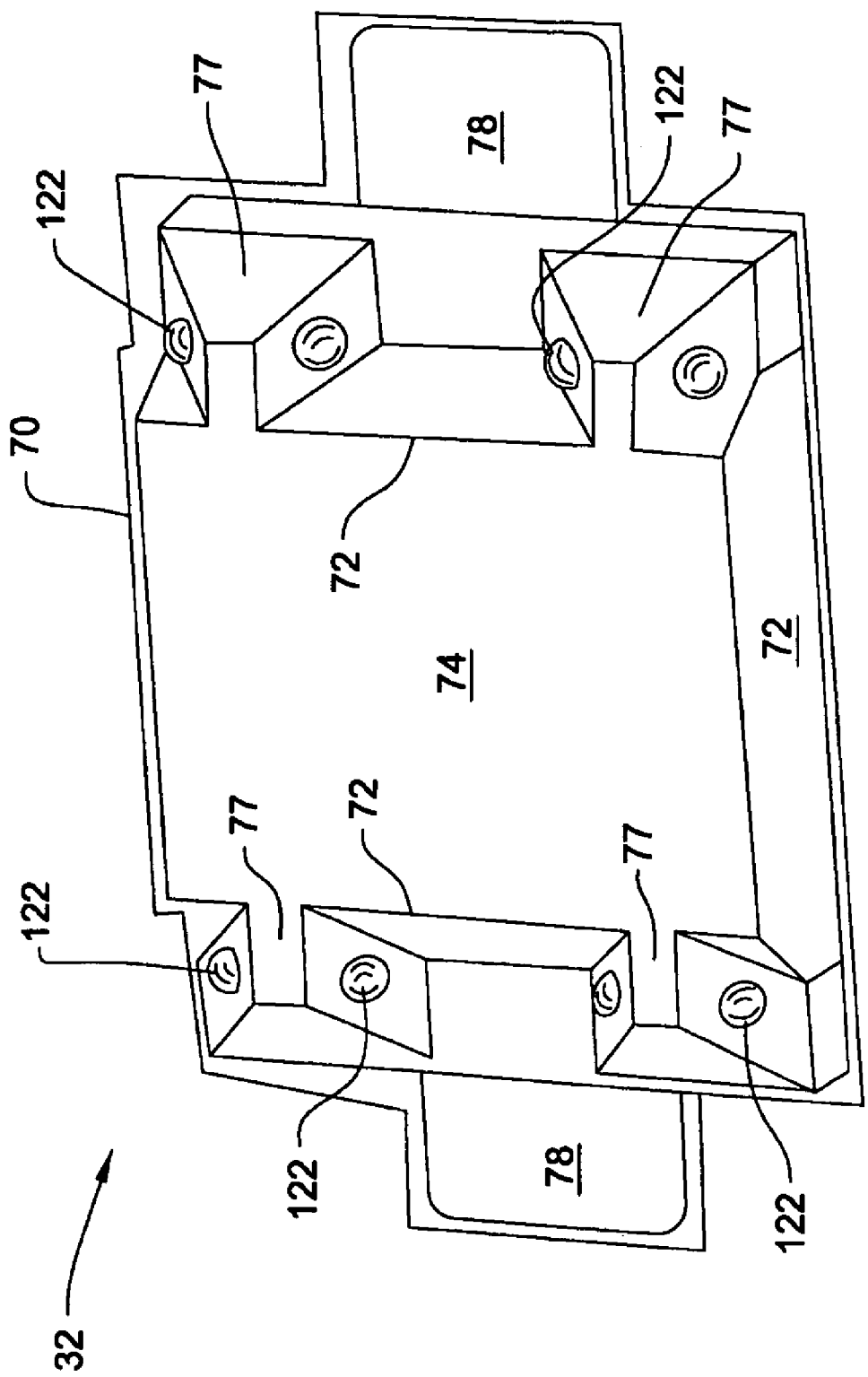
FIG. 4 is a perspective view of a tracker of this invention.

As seen in FIG. 4, tracker 32 includes a housing 70. In some versions of the invention, housing 70 is formed from non-magnetic material. Autoclave sterilizable, reusable versions of the housing are formed from metal. Potential metals are aluminum, titanium and 300 series stainless steel. In some versions of the invention, housing 70 is formed from plastic or ceramic. Housing 70 has a planar base 71, seen diagrammatically in FIG. 6. Four side walls 72 extend perpendicularly from the base 71 a top panel 74 is extends across the top of the side walls 72 so that housing 70 forms a sealed enclosure. Top panel 74 is generally planar.

Tracker 32 of FIG. 4 is further formed so that the side walls 72 on the left and right sides of the base 71. Two fingers 77, each with the cross sectional profile of a truncated triangle, project outwardly from each side wall 72 to the adjacent base edge. Each finger 77 is located at one end of the associated side wall 72. Each finger 77 thus extends the enclosed sealed space inside the tracker housing 70. A single LED 122 is mounted to each of the two inclined sections of each finger 77. LEDs 122, as discussed below, are part of the second navigation system that forms the hybrid system of this invention. Generally tracker housing 70 has a maximum length 20.0 cm or less, in more preferred versions, 10.0 cm or less and a width of 12 cm or less, in more preferred versions, 9.0 cm or less. This means that the housing has a surface area that is pressed against the skin of 240 cm$^2$ or less, an preferably 180 cm$^2$ or less, more preferably 120 cm$^2$ less and still more preferably 90$^2$ cm or less. Typically, the housing 70 has a depth of 8.0 cm or less and, in more preferred versions 4.0 cm or less.

The tracker 32 is further formed so that integral with base 71 are two opposed tabs 78. Each tab 78 extends outwardly from the base edge from which a pair of fingers 77 extends. When the tracker 32 is mounted to the patient two approximately parallel straps or bandages 79 (FIG. 6) are placed over the patient around the location at which the tracker is to be placed. The straps/bandages 79 are formed with pockets 80, for receiving the tracker tabs 78. The seating of the tabs 78 in strap/bandage pockets thus holds the tracker to the patient.

Figure 5:
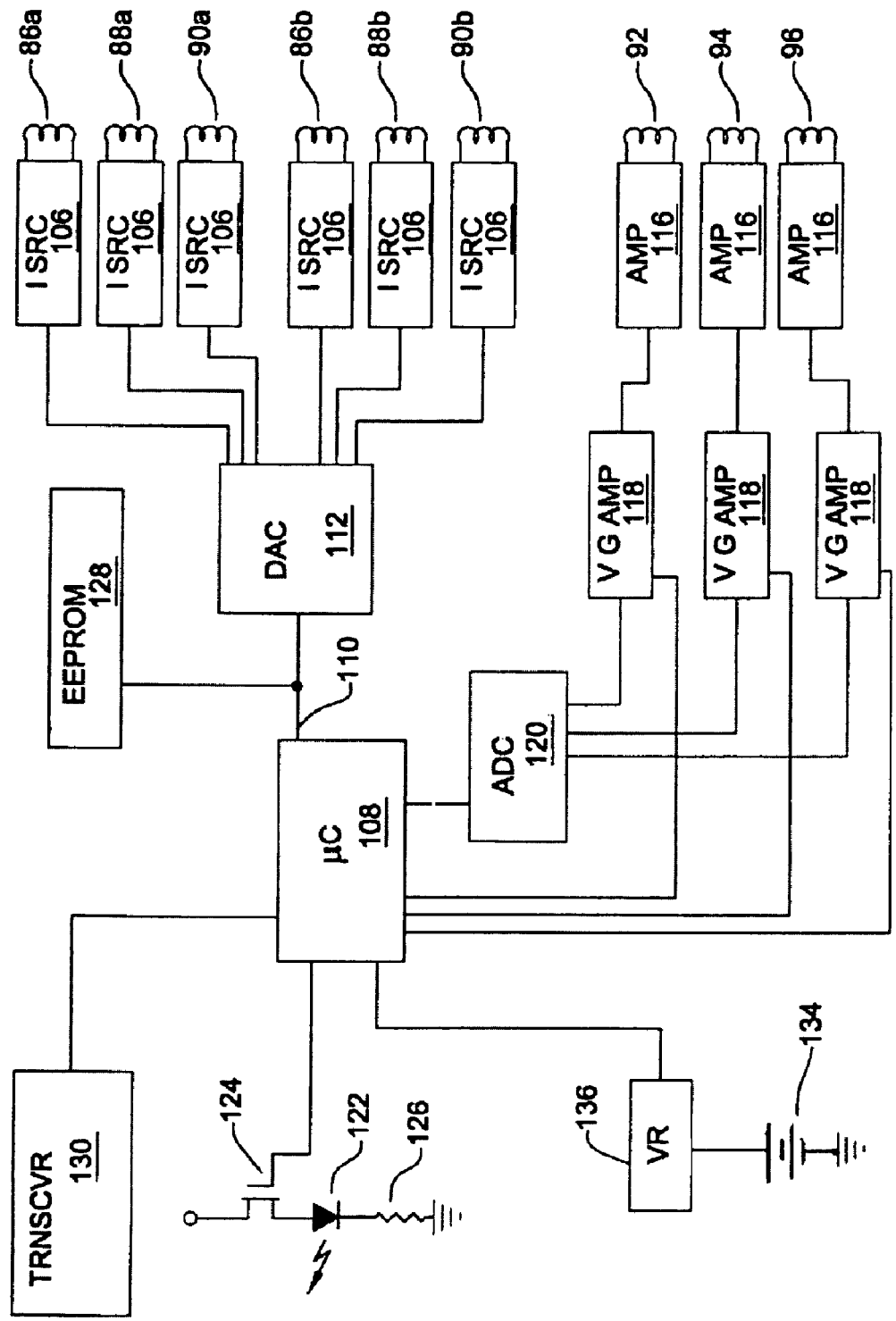
FIG. 5 is a block and schematic view of the components internal to the tracker.
Figure 6:
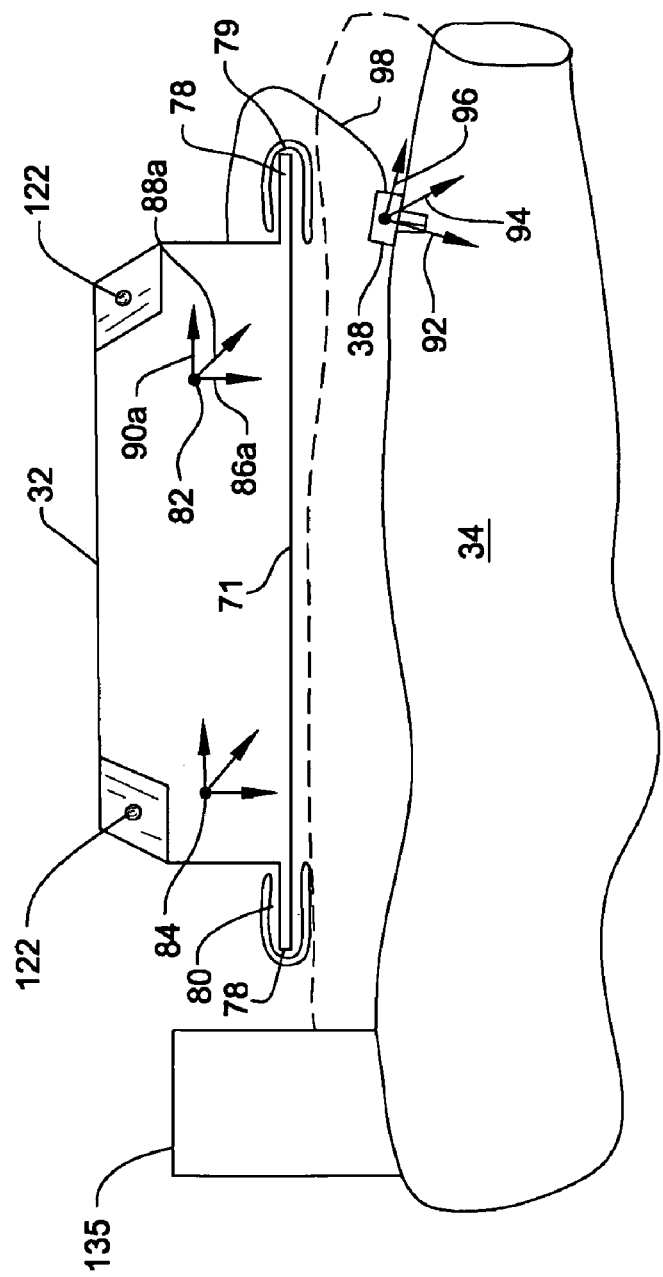
FIG. 6 is a diagrammatic view of how the bone marker and tracker of this invention of this invention are fitted to the body in order to track the position and orientation of the body.

FIGS. 5 and 6 illustrate the active components of tracker 32 and bone marker 38. Specifically, internal to the tracker 32 are two transmitter assemblies 82 and 84. The transmitter assemblies are positioned so that a first assembly, transmitter assembly 82, is located at one end of the housing and the second assembly, transmitter assembly 84, is located at the opposed end of the housing. Each transmitter assembly 82 and 84, includes a first coil capable of transmitting an EM signal in the X direction a second coil capable of transmitting an EM signal in the Y direction and a third coil capable of transmitting a signal in the Z direction. In FIG. 6, the individual X-, Y- and Z-coils of transmitter assembly 82 are represented by arrows 86a, 88a and 90a, respectively. In some preferred versions of the invention, the coils are mutually orthogonal and centered on a common point. In some versions of the invention it is contemplated the coils are wound around a common square block.

Precision, voltage-controlled, bi-polar variable current sources 106 disposed in the tracker 32 generate variable current signals that are applied to the transmitter coils. In FIG. 5, tracker 32 is shown as having six separate current sources 106. Three current sources 106 apply separate signals to the coils 86a, 88a and 90a of transmitter assembly 82. The remaining three current sources 106 each apply signals to the separate coils 86b, 88b and 90b of transmitter assembly 84.

While not illustrated, the individual current sources 106 each includes a feedback circuit to ensure that the DC current running through the associated coil is, as close as possible, zero. This DC current damping is needed to ensure the magnetic fields emitted by the coils are of as precisely controlled strengths as possible.

A microprocessor 108 asserts the signals that cause current sources 106 to independently output signals at different current levels. In some versions of the invention, microprocessor 108 is a digital signal processor. One such digital signal processor is the fixed point digital signal processor No. TM320VC5502 available from Texas Instruments of Dallas, Tex. Current source command signals are output by processor 108 as digital signals. These signals are output over a bus 110 to a digital to analog converter (DAC) 112 with six output ports. The DAC 112, based on data that comprise each command generated by the microprocessor 108, generates an AC level signal to the input pin of each current source 106.

Transducer 66 is the active component internal to the bone marker 38. The transducer consists of three coils 92, 94 and 96 sensitive to electromagnetic energy. Ideally, the transducer coils are mutually orthogonal and centered on a common point. Thus, like the transmitter assembly coils, coils 92, 94 and 96 may be wound around a common square block. A set of conductors connect coils 92, 94 and 96 to the inside of the tracker housing 70. In FIG. 6, the conductors are represented by a single cable 98. In some versions of the invention, there are three conductors; a common ground and a single conductor connected to each coil. In alternative versions of the invention there are six conductors; a pair of conductors connects each coil 92, 94 and 96 to the tracker 32.

As also seen in FIG. 5, the individual coils 92, 94 and 96 of the transducer assembly are attached to separate fixed gain amplifiers 116. The output signal from each fixed gain amplifier 116 is applied to a variable gain amplifier 118. The gain of each amplifier 118 is set by a control signal asserted by the microprocessor 108. Microprocessor 108, it should be understood, is able to set the individual gains of the amplifiers 118 independently from each other. In one version of the invention, fixed gain amplifiers 116 each have a gain of 10,000; each variable gain amplifier 118 can be set to have a gain of 1, 10 or 100. In an alternative version of the invention, the fixed gain amplifiers each have a gain of 1,000; each amplifier 118 can be set to have a gain of between 1 to 1,000 that is set in single step increments.

The output signals produced by the variable gain amplifiers 118 are applied to an analog to digital converter 120. The digitized representations of the amplified versions of the signals measured across the transducer coils 92, 94 and 96 are supplied from the ADC 120 to the microprocessor 108.

As mentioned above, tracker 32 also contains components of the second navigation system. In FIG. 5 this is represented by a single IR emitting LED 122. The application of a voltage across the LEDs 122 is controlled by a FET 124 tied to the LED cathode. A load resistor 126 is tied between the anode of LED 122 and ground. Microcontroller 108 asserts the gate signal to FET 124 to regulate the actuation of the LED 122.

In FIG. 5 an EEPROM 128 is also shown connected to microprocessor 108 over bus 110. The EEPROM 128 stores both the operating instructions executed by the microprocessor 108 as well as some of the intermediate data generated by the microprocessor.

Also integral with the tracker is a wireless transceiver 130. Transceiver 130 exchanges signals with system processor 44. Often the signals emitted by transceiver 130 are directed to a complementary transceiver in the localizer 40 (transceiver 132 shown as a phantom block in FIG. 1). In some versions of the invention, transceivers 130 and 132 exchange RF signals. In still other versions of the invention, transceivers 130 and 132 exchange visible, UV or IR signals. The exact type of signals exchanged by the transceiver 130 and the complementary external transceiver 132 are not relevant to the structure of this invention.

All the components internal to the tracker 32 are powered by a battery 134 also internal to the tracker. Battery 134 is shown connected to a voltage regulator 136. One constant voltage connection, the connection that supplies a current to energize the microcontroller 108 is shown. To minimize complexity of the drawings the remaining power supply connections are not shown.

II. Operation of the Basic System

Figure 7:
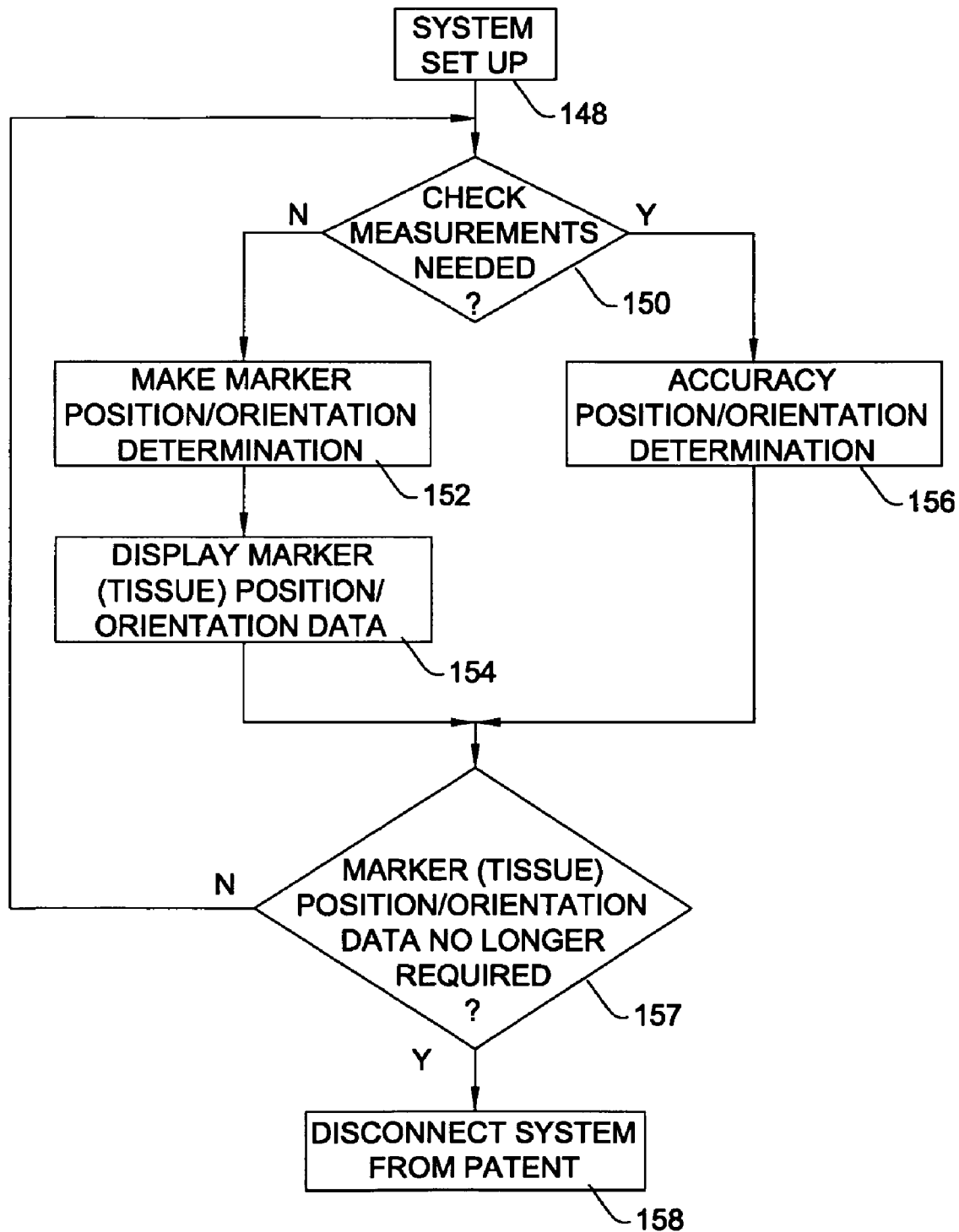
FIG. 7 is a flow chart of the overall, basic steps executed by the system of this invention to determine position and orientation of a section of patient tissue.

Operation of system 30 of this invention is now described by initial reference to the flow chart of FIG. 7. In a joint replacement procedure, the system is used to track the position and range of movement of bone prior to the procedure and during the procedure. In this type of procedure, a device known as a cutting guide 135 (shown as a block disposed above the leg of FIG. 6) is typically fitted to the bone adjacent to where the joint is to be replaced. Cutting guide 135 guides the cut of a saw that is employed to remove the joint to be replaced. The cutting guide 135 is used in this procedure to ensure that the bone left in place after the removal is properly shaped to receive the components forming the artificial joint.

Initially, as represented by step 148, system 30 is set-up for use. Once system 30 is set up for use, a measurement is made of the position and orientation of the marker 38 and, by extension, the tissue to which the marker is attached. Once the marker/tissue position and orientation information are generated, in a step 152, this information is presented to the surgeon, step 154. Typically, this information is presented on display 46. Steps 152 and 154 are repeatedly executed throughout the surgical procedure in order to provide real time information regarding the position and orientation of the tissue to which the marker 38 is attached.

Occasionally during the procedure, system 30, in a step 156, checks the accuracy of the position and orientation determination made in step 152. For example in some versions of the invention, steps 152 and 154 are typically performed at a frequency of between 10 to 100 Hz and, more often, between 25 to 75 Hz. Step 156 is performed at frequency of between 0.5 Hz to 5 Hz. Step 150 represents the decision made by either system processor 44 or tracker microcontroller 108 to determine which one of steps 152 or 156 is to be performed. Alternatively, in some versions of this invention, when the check of step 156 is performed, this step is performed essentially simultaneously with, instead of as a substitute for, the measurements of step 152.

Steps 150, 152, 154 and 156 are repetitively preformed throughout the time it is necessary for the surgical personnel to be provided with tissue position and orientation data. Eventually, there is point in the surgical procedure at which it is no longer necessary to monitor the position and orientation of the tissue, step 157 of FIG. 7. Once the procedure is at this point, in a step 158, system 30 is removed from the patient.

Figure 7A:
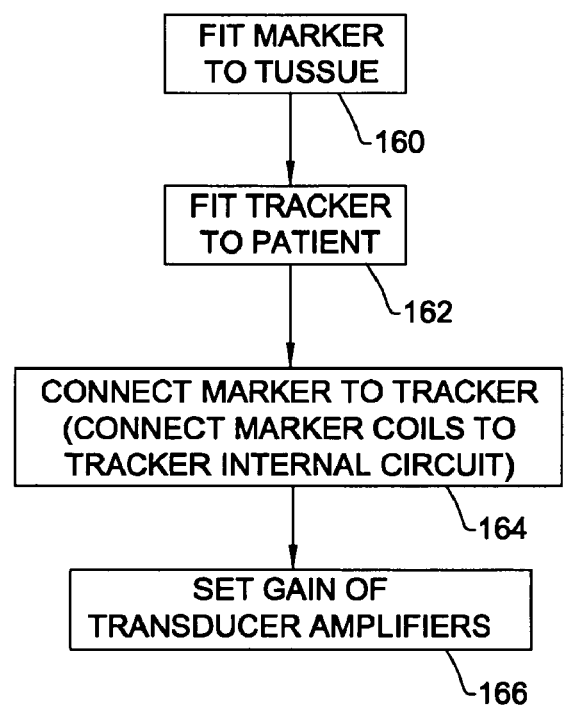
FIGS. 7A, 7B, 7C and 7D, are flow charts of the more detailed process step executed by the system when performing the overall process of FIG. 7.

The individual steps that comprise the system set up step 148 are now described by reference to FIG. 7A. In a step 160, an insertion tool is used to mount the bone marker 38 to the bone, tibia 32. Generally, the marker 38 is positioned a distance from the cutting guide 135 greater than the length of the tracker 34. In one method of fitting the bone marker 38, after the marker is positioned, the insertion tool applies an impacting force to the marker head 50. The force generated by the insertion tool drives the marker stem 52 into the underlying bone cortical layer.

During the actual insertion process, only the cortical material subtended by the marker stem 52 is driven away from the stem, towards the center of the bone. The adjacent cortical material, the material in the space outward of the concave walls 60, remains static. This bone material abuts the stem inwardly curved walls 60 to prevent the rotation of the stem 52. Immediately after the insertion, the material compressed outwardly away from the stem expands back towards its initial position. This material seats in stem grooves 64 to prevent longitudinal movement of the stem 52. Thus, collectively, the bone material that abuts stem walls 60 and that seats in grooves 64, block the stem 54 and, therefore the whole of the marker 38, from movement.

In a step 162, the tracker 32 is positioned between the bone marker 38 and the cutting guide 135. Bandages/straps 79 are fitted around tracker tabs 78 to hold the tracker 32 to the leg. For reasons that will be apparent below, this invention does not require the tracker 32 to be securely attached to the leg. In a step 164, wire cable 98 that extends from marker head 50 is passed through the soft tissue and skin and connected to the tracker housing 70. This physical attachment connects transducer coils 92, 94 and 96 to amplifiers 116.

Prior to the generation of EM energy by the tracker 32, in step 166, microcontroller 108 asserts the control signals to establish the gains of the individual amplifiers 118. The variables that affect the gain settings include: the distance between the tracker and the bone marker; drive current; number of signal transmitting and receiving elements (windings); and ambient noise; geometries and sensitive surface areas of both the transmitter and receiver.

Figure 7B:
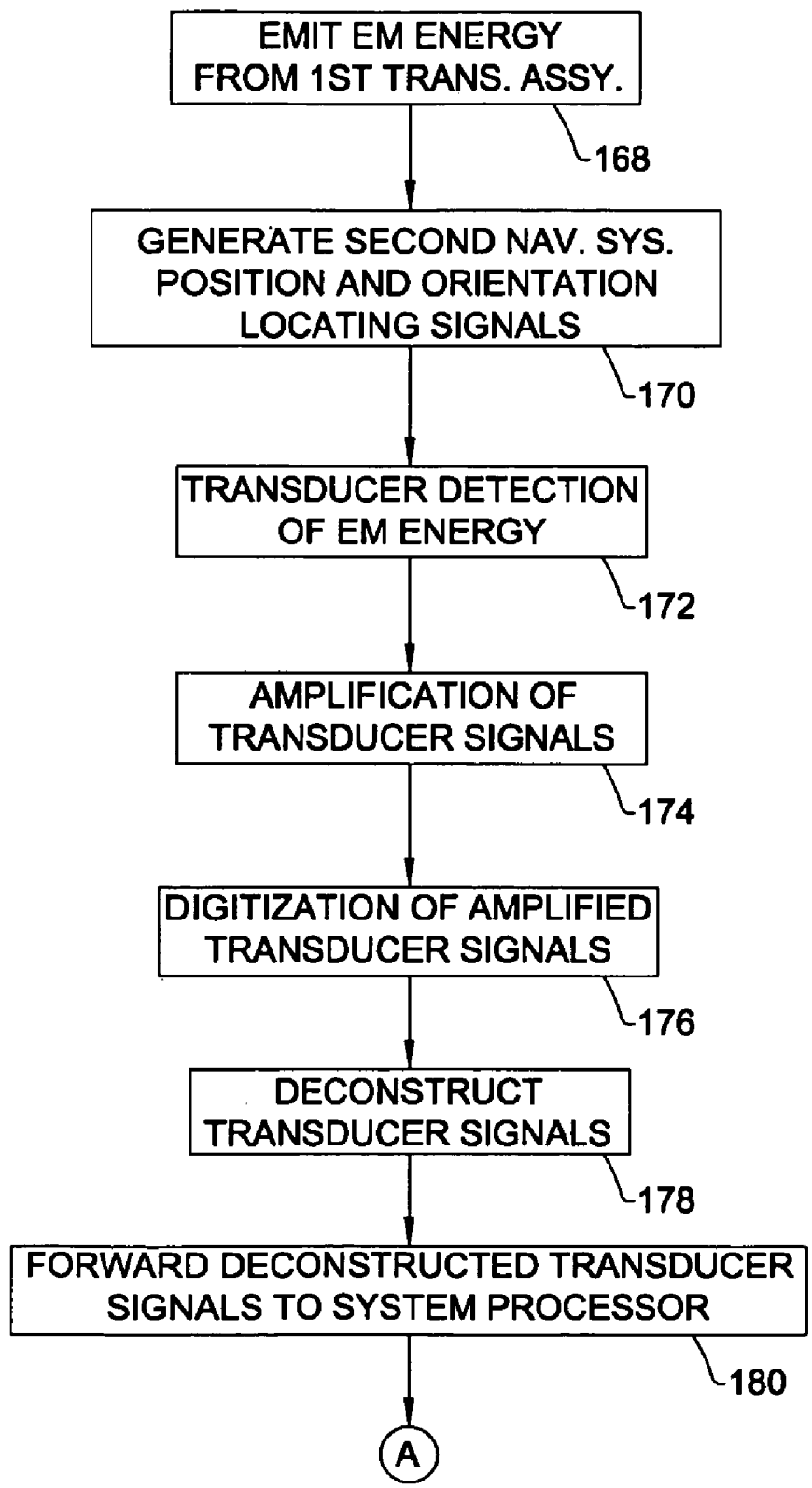
Figure 7C:
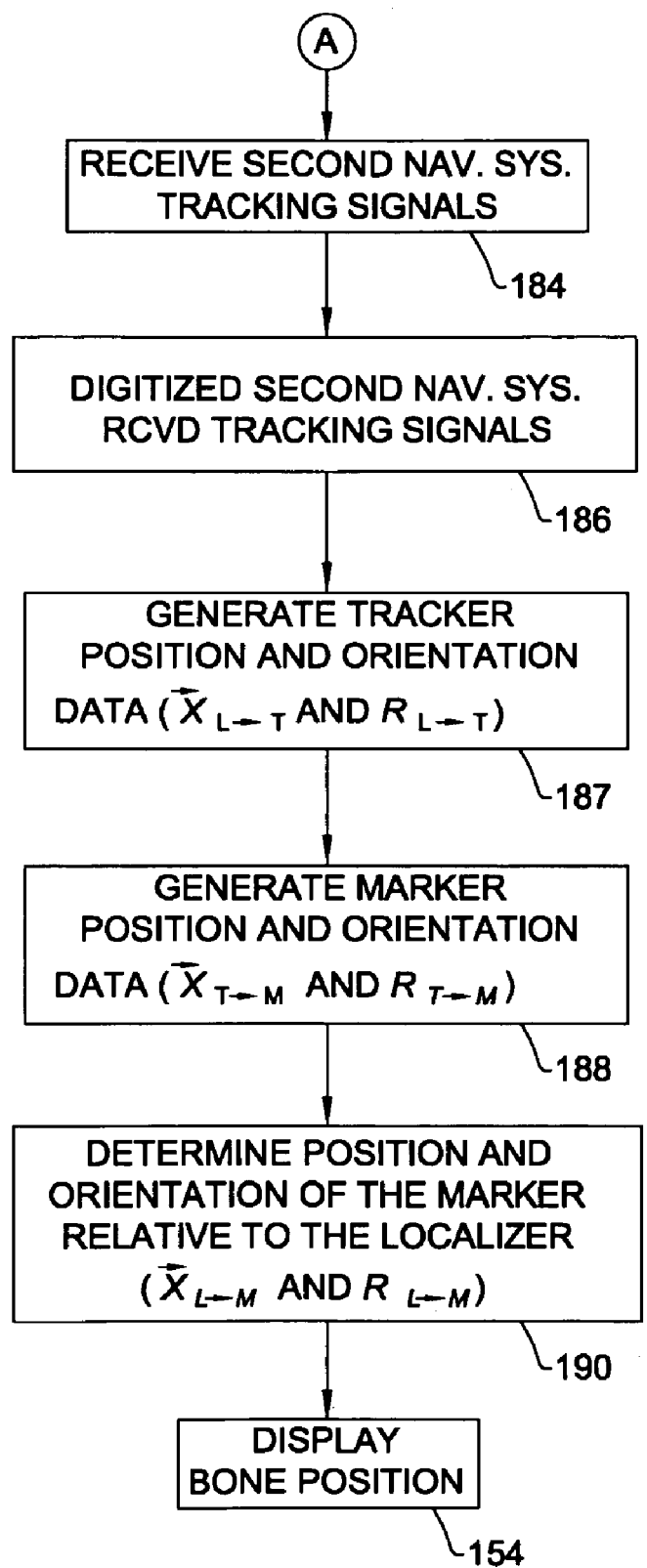

Once the system is configured for operation, step 148 is completed, steps 151, 152 and 154 can be executed. The sub-steps that form step 152 are now described by reference to FIGS. 7B and 7C. The actual generation of data to indicate tissue position and orientation begins, in step 168, with the simultaneous emission of EM signals by coils 86a, 88a, and 90a of transmitter assembly 82. Step 168 is executed by microprocessor 108 asserting signals through DAC 112 to the appropriate current sources 106 that cause AC currents to be applied to coils 86a, 88a, and 90a. In many versions of the invention, the signals have frequencies between 100 and 1,000 Hz. The signals applied to coils 86a, 88a, and 90a are at different frequencies. In some preferred versions of the invention, the signals are at a harmonics of a base frequency. In some versions of the invention, one of the frequencies may even be applied at the base frequency. The Applicants' Assignee's U.S. Patent Application System and Method for Electromagnetic Navigation in the Vicinity of a Metal Object, U.S. Pat. Pub. No. 2006/0264732 A1, the contents of which are now incorporated herein by reference, describe the reasons why it is desirable to apply signals having the above relationship to the coils 86a, 88a, and 90a. The signals applied simultaneously to the coils 86a, 88a, and 90a are at cumulative power level of 5 Watts or less and, in more preferred versions of the invention, 0.5 Watts or less. Thus, the signal applied to a single coil is generally at 1.67 Watts or less and more preferably 0.17 Watts or less.

As part of step 168, it should be understood the phases of the signals the current sources 106 apply to coils 86a, 88a and 90a are also regulated.

Simultaneously with, or as near as simultaneously as possible with step 168, in a step 170, microcontroller 108 also causes the LEDs 122 of the second navigation system to emit photonic energy detectable by localizer 40.

The current flow through transmitter coils 86a, 88a, and 90a result in the emission of EM waves by the coils. As a consequence of the emittance of the EM energy by transmitter assembly 82, potentials simultaneously develop across the three transducer coils 92, 94 and 96, step 172. As part of step 172, these signals are therefore forward through cable 98 to fixed gain amplifiers 116. Step 174 represents the amplification of these signals. Specifically these signals are first amplified by the fixed gain amplifiers 116. Then, also part of step 174, the output signals from amplifiers 116 are subjected to variable gain amplification by amplifiers 118. In a step 176 the amplified signals from the transducer coils 92 94 and 96 are digitized by ADC 120 and applied to microcontroller 108.

Then, in a step 178, microcontroller 108 deconstructs each of the signals produced by the transducer coils 92, 94 and 96. Specifically, the microprocessor 108 employs a Fast Fourier Transformation (FFT) to break down each coil signal into the components formed as a consequence of the simultaneous emission of three magnetic fields by transmitter assembly 82. Each signal is broken down into the amplitude and phase components for each of the three EM waves that contributed to the generation of the signal.

In a step 180, microcontroller 108, through transceiver 130, transmits packets to system processor 44 that contain data defining the components of the transducer assembly signals.

The IR light emitted by LEDs 122 in step 170 is detected by the receivers internal to the localizer 40, step 184. Digitized signals representative of the direction and strength of the received light are, in a step 186 applied to system processor 44.

Based on the digitized data from the localizer receivers received in step 187, system processor 44 generates data that describes the position and orientation of the tracker 34 relative to the localizer 40. These data include a translation vector $\vec{x}_{L \rightarrow T}$ that represents the position of the tracker 34 relative to the localizer. A rotational matrix $R_{L \rightarrow T}$ that represents the rotation of x-, y- and z-axes of the tracker 34 relative to the x-, y- and z-axes of the localizer is also generated.

In a step 188, based on the deconstructed transducer assembly data, system processor generates data that describes the position and orientation of the bone marker 38 relative to the tracker 32. These data include a translation vector $\vec{x}_{T \rightarrow M}$ representative of the position of the bone marker 38 relative to the tracker 32. These data also include rotational matrix $R_{T \rightarrow M}$ which represents the rotation of the x-, y- and z-axes of the bone marker 38 relative to the x-, y- and z-axes of the tracker 32.

Based on the data generated in steps 187 and 188, system processor, in step 190 generates data representative the position and orientation of the bone marker 38 relative to the localizer. These data are vector $\vec{x}_{L \rightarrow M}$, which represents the position of the bone marker relative to the tracker and rotational matrix $R_{L \rightarrow M}$, the rotation of the x-, y- and z-axes of the bone marker 38 relative to the x-, y- and z-axes of the localizer 40. In step 190, these data are calculated according to the following formulas:

$$\vec{x}_{L \rightarrow M} = \vec{x}_{L \rightarrow T} + R_{L \rightarrow T} \cdot \vec{x}_{T \rightarrow M} \quad (1)$$

and $$R_{L \rightarrow M} = R_{L \rightarrow T} \cdot R_{T \rightarrow M} \quad (2)$$

The above equations assume the transmitter assembly 82 is located exactly at the center location of the tracker, at the position and with the orientation specified $\vec{x}_T$ and $R_T$. In actuality, there are offsets between the locations and orientations of the tracker assemblies 82 and 84 and the position and orientation of the tracker as determined in step 186. These offsets are determined at time of manufacture. Therefore, step 190 includes the execution of intermediate processing steps employing variations of Equations 1 and 2 above to account for these offsets. In these steps, the translational vector and translation rotation matrix data are determined based on the data regarding tracker position at time of manufacture.

Once step 190 is executed, processor 44 contains data that indicates the position of the bone marker 38 relative to the localizer 40. Processor 44 is therefore able to, in step 154, present an image on the display 44 that indicates the position of the bone marker 38 and by extension, the section of bone in which the marker is mounted.

In a knee replacement procedure, while not illustrated, it should be understood another bone marker is used to track the position of the femur. At the start of the procedure, the bone marker position and orientation data from both markers is used to determine the positions of the two bones relative to each other and the range of motion of the two bones. These data are then used by the surgeon to ensure that the components forming the implant are properly positioned so that, post-procedure, the bones will be in the proper positions and the patient has the appropriate range of movement.

It should further be appreciated that, while the steps 168-190 are shown as occurring sequentially, this is for simplicity of illustration only. In practice some of these steps are preformed simultaneously. For example in some versions of the invention, while tracker microcontroller 108 is performing the deconstruction of the signals from coils 92, 94 and 96, step 178, system processor 44 can simultaneously be determining the position and orientation of the tracker, step 187.

Step 156 of FIG. 7 is performed to verify that the marker/tissue position and orientation data provided by the system 30 is accurate. One reason these data may be inaccurate is that, if a ferromagnetic object is in very close proximity to the components of the system, the object can adversely affecting the accuracy of the measurements made by the system. A ferromagnetic object can have such an affect because, owing to the nature of the object it diverts the magnetic fields emitted by the transmitter assemblies 82 and 84. This, in turn, causes transducer assembly 66 to output signals that cannot be used to properly determine position and orientation of the bone marker 38. As discussed below, another source of interference can be EM signals generated by other equipment used to perform the surgical procedure.

Figure 7D:
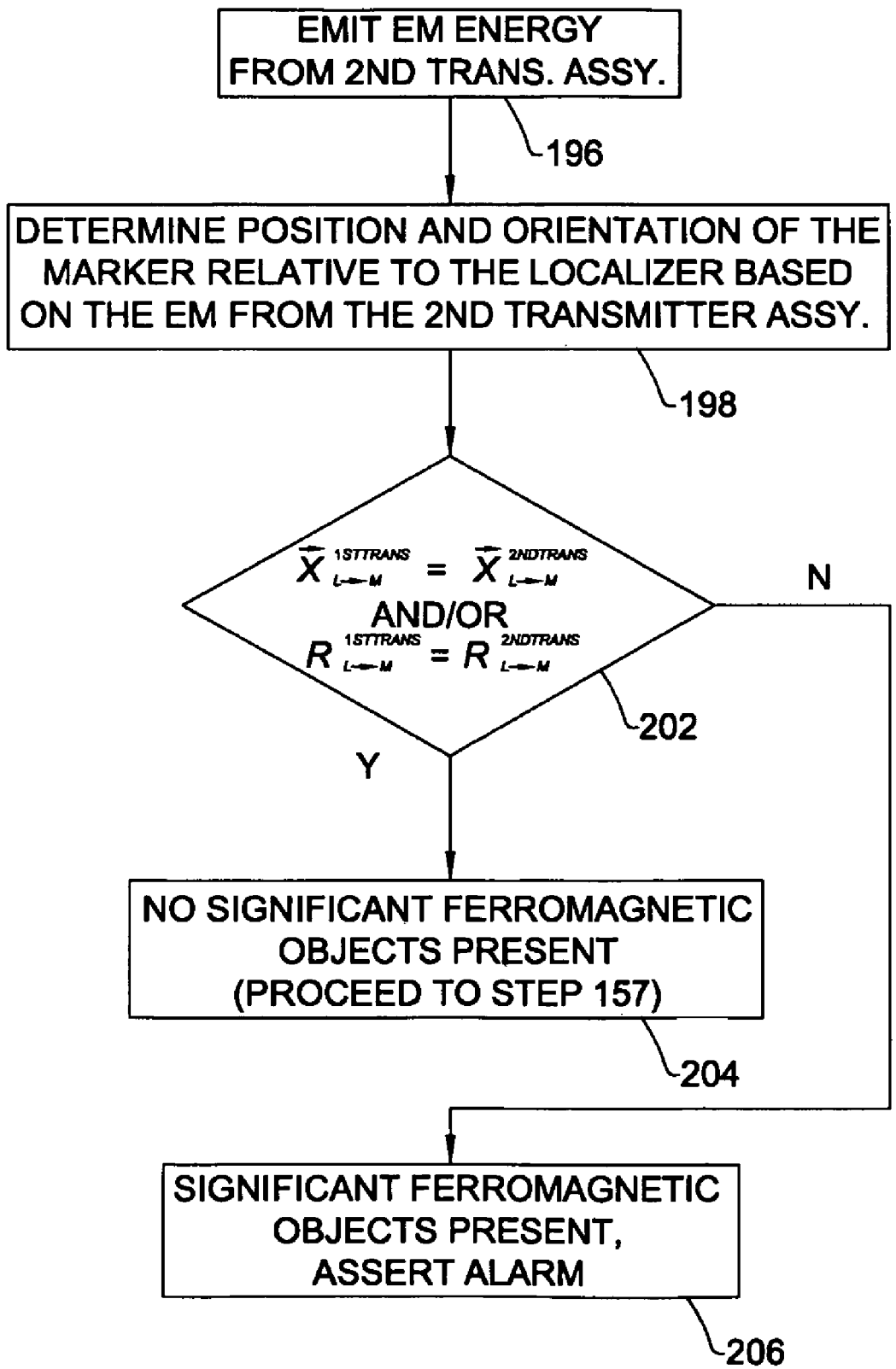

FIG. 7D illustrates the sub steps that form step 156. Thus, step 156 starts with a step 196 in which microcontroller 108 asserts control signals that cause the current sources 106 to which transmitter assembly 84 coils 86b, 88b and 90b are connected to output drive signals. Again, it should be understood that step 196 may be performed as an alternative to step 168. In versions of the invention, when steps 152 and 156 are preformed simultaneously, steps 168 and 196 are therefore preformed simultaneously.

After the execution of step 196, processing steps similar to steps 170, 172, 174, 176, 178, 180, 184, 186, 188 and 190 are performed with regard to the EM waves emitted by transmitter assembly 84 and measured by transducer assembly 66. Collectively, these steps are represented as step 198, the generation of translation vector $\vec{x}_{L \rightarrow M}^{2NDTRANS}$ of the distance from the localizer to the bone marker and $R_{L \rightarrow M}^{2NDTRANS}$, the rotational matrix that represents the rotation of the bone marker relative to the localizer as based on the signals emitted by transmitter assembly 84.

Thus, after the execution of step 190 and the near simultaneous execution of step 198, system processor 44 contains the following data, vector $\vec{x}_{L \rightarrow M}^{1STTRANS}$ of the distance from the localizer to the bone marker and $R_{L \rightarrow M}^{1STTRANS}$, the rotational matrix that represents the rotation of the bone marker relative to the localizer as based on the signals emitted by transmitter assembly 82 and $\vec{x}_{L \rightarrow M}^{2NDTRANS}$ and $R_{L \rightarrow M}^{2NDTRANS}$. Then in a step 202 processor 44 determines if the two translation vectors are substantially equal and/or if the two rotational matrixes are substantially equal.

If the evaluation (s) test(s) true of step 202 tests true, than system processor 44 recognizes the environment in one in which no significant ferromagnetic devices or objects are present, step 204. Steps 157, 150, 152 and 154 are then repetitively reexcuted until the next time step 156 is reexcuted.

Alternatively, in step 202 it may be determined that vectors $\vec{x}_{L \rightarrow M}^{1STTRANS}$ and $\vec{x}_{L \rightarrow M}^{2NDTRANS}$ are not equal and/or rotational matrixes $R_{L \rightarrow M}^{1STTRANS}$ and $R_{L \rightarrow M}^{2NDTRANS}$ are not equal. One or both of these conditioning existing is interpreted by system processor 44 as an indication that a ferromagnetic object is adversely affecting the magnetic waves that are being sensed by the transducer assembly 66. Therefore, in a step 206, system processor 44 asserts an alarm regarding this environmental state. The assertion of this alarm provides notice to operating room personnel that a ferromagnetic object has been introduced into the environment at a location that is adversely affecting the ability of system 30 to track the bone marker 38. The steps necessary to remove the ferromagnetic object can be taken. Alternatively, as discussed below with respect to FIGS. 13A and 13B, system 30 undergoes a frequency shifting process to find frequencies which the transmitter assemblies 82 and 84 can emit EM waves that are not adversely affected by the ambient EM signals.

Returning to FIG. 7, it is understood that eventually there is a point in the surgical procedure at which, in step 157 it is no longer necessary to monitor marker/tissue position and orientation. At this time step 158 is performed in order to disconnect the system from the patient. First, the tracker 32 is removed. Then, also as part of step 158, the bone marker 38 is removed. This task is accomplished by initially rotating the marker 38. The rotation of the marker 38 results in the bone material seated adjacent the marker stem wall 60 rotating with the marker. This material thus breaks free of the surrounding bone. Simultaneously, the rotation of the marker results in the stem 54 rotating to the position where the stem is free of the material seated in grooves 64. Thus, once the marker 38 is so rotated, the removal is completed by the relatively easy task of the simply longitudinal pulling of the marker away from the bore in which the stem 54 is seated.

System 30 of this invention used to track tissue location using a relative small bone marker 38. Consequently, only a relatively small incision is required to mount this marker. Thus, system 30 of this invention provides a means to track tissue without requiring the mounting of a large structural member to the tissue. Thus, this invention eliminates the trauma to the tissue associated with the mounting of such a device.

The system 30 is further designed so that tracker 32 is mounted to the patient immediately above the skin. Given that the tracker 34 is of relatively small size, the tracker does not function as a large obstacle around which the surgical personnel need to maneuver.

Still another feature of system 30 is that the transmitter assemblies 82 and 84 are typically spaced less than 25 cm from the transducer 66 and more often 15 cm or less. One benefit of this arrangement is that only relatively low powered EM waves need to be transmitted from the transmitters 82 and 84 to the transducer 66. The lower power of these waves essentially eliminates the possibility they will damage the tissue through which they are transmitted. It will further be appreciated that this separation between the marker and the tracker is less than the distance separating the tracker from the localizer 40.

A further feature of this invention is that relatively small amounts of power are required to energize the components internal to both the tracker 32 and the marker 38. Often these components collectively require an instantaneous power of 10 Watts or less of power and, in more preferred versions of the invention 2 Watts or less. Thus, the power required to supply these components can be provided by a batter attached to the tracker 32. This eliminates the need to introduce a power cord into the surgical field in order to monitor the position and orientation of the tissue.

Another advantage of the proximity of the transmitter assemblies to the transducer assembly of system 30 is that it results in there being a relatively small space around the transmitter and transducer assemblies in which the presence ferromagnetic object can adversely affect the measurement of the EM waves. Thus, ferromagnetic surgical instruments can be placed relatively close to the tracker, within a distance as close as 10 cm and sometimes a distance as close as 5 cm, without adversely affecting the operation of system 30.

The above utility of system 30 is further understood by reference to FIG. 6. Here it can be seen that the bone marker 38 is spaced a distance from the area where the surgical procedure is to be performed by a distance greater than the length of the tracker 32. This distance, the tracker length, defines the space in which the introduction of the ferromagnetic objects could affect the measurements made by the transducer assembly 66. The tracker 38 thus acts a guide block representative of the minimum distance ferromagnetic surgical devices and objects should be placed away from the bone marker 38 in order to ensure system 30 properly tracks the marker.

During periods of time the transmitted EM waves are adversely affected by either other objects or other EM waves, for example, those emitted by a powered surgical tool, system 30 determines if such interference is present. Thus, system 30 of this invention is further designed to provide an indication if the ambient conditions inhibit the accurate generation of tissue tracking data.

Tracker 32 is designed so that the transmitting LEDs 122 of the second navigation system are located on opposed sides of the fingers 77. Thus, in substantially most orientations of the tracker 32 relative to the localizer, sufficient photonic energy will be emitted by the tracker LEDs 122 that will be received by the localizer to ensure processor 44 has sufficient data to determine the position and orientation of the tracker 32 relative to the localizer 40.

Still another feature of system 30 of this invention is that bone marker 38 is designed so that, upon insertion into the bone, it remains locked in position. Then, when it is time to remove the marker, once the marker is rotated from the locked position, minimal force is required to complete the removal process.

The foregoing is directed to one specific version of system 30 of this invention and one specific procedure in which the system is used. Variations in both the constructions of the invention and its method and methods of use are possible.

For example, the system 30 can be further be used to assist in the tracking of the location of a surgical instrument relative to a surgical site. In these uses of the system 30, prior to the actual procedure, the tissue at the surgical site is mapped. Data describing the map are loaded into system processor 30. At the start of the procedure, bone marker 30 is positioned at a precisely known mapped body position.

During the procedure, the system monitors the position and orientation of the bone marker 38 so as to, by extension, determine the position and orientation of the surgical site. Simultaneously, localizer 40 is used to monitor the position and orientation of a surgical instrument. Based on these data, system processor 44 is able to generate data indicating the position and orientation of the instrument relative to the surgical site.

III. First Alternative Tracker

Figure 8:
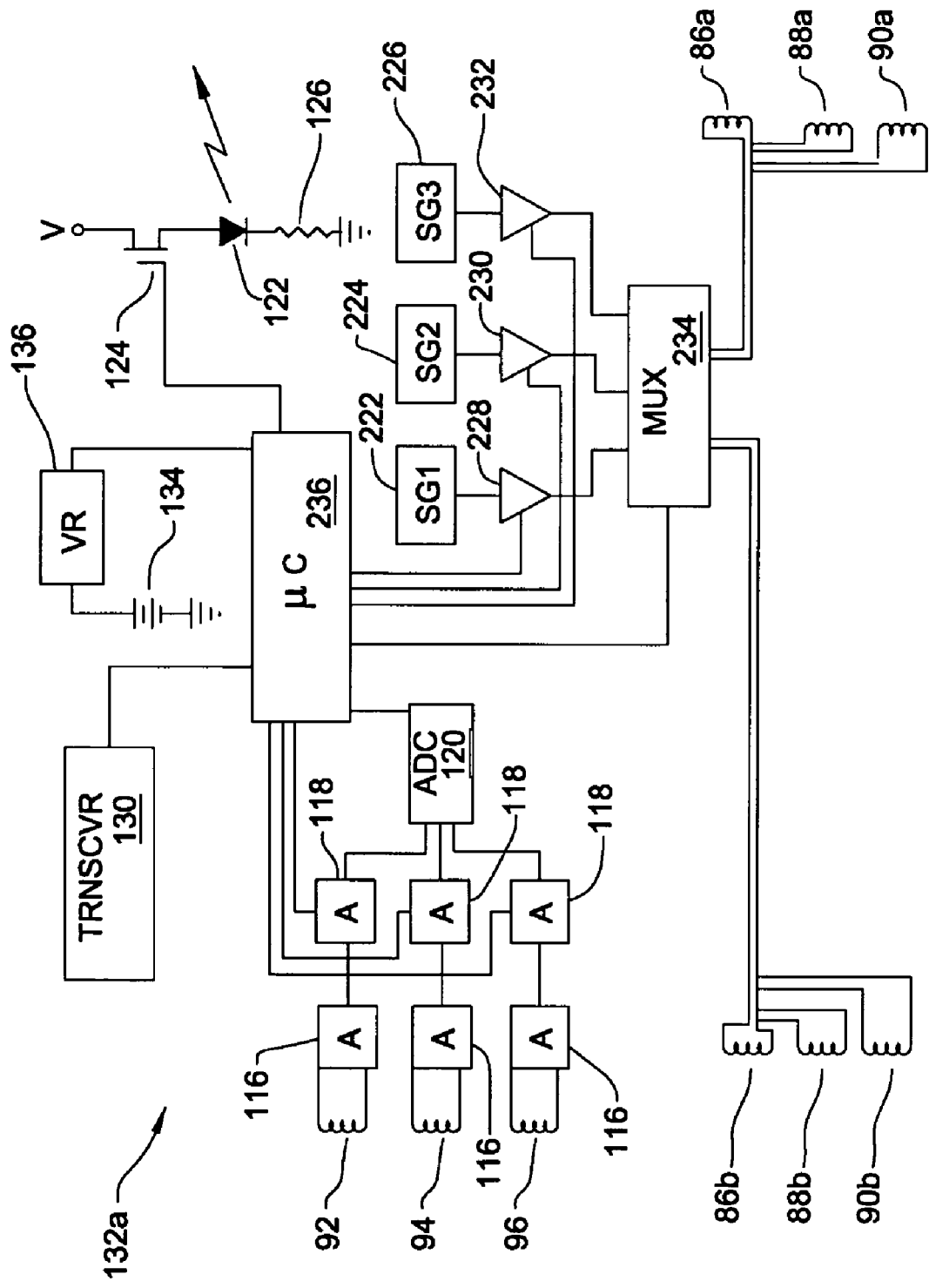
FIG. 8 is a block and schematic diagram of the components disposed in an alternative tracker of this invention.

Further, constructions of the system may vary from what is described above. FIG. 8 illustrates in block diagram of an alternative components that may be provided in a tracker 32a. In this version of the invention, tracker 32 has three signal generators 222, 224 and 226 internal also internal to tracker 32 energize the coils of transmitter assemblies 82 and 84. The signal generators 222-226 are configured to be energized simultaneously. Each signal generator 222-226 emits a signal at a constant frequency. Collectively, the signals emitted by signal generators 222-226 are emitted at different frequencies.

The signals output by the individual signal generators 222, 224 and 226 are amplified by separate amplifiers 228, 230 and 232, respectively. The output signals from amplifiers 228, 230 and 232 are applied to three input ports of a 2:1 multiplexer 234. A first set of output ports of the multiplexer 234 are tied to the three coils 86*a*, 88*a* and 90*a* of transmitter assembly 82. The second set of three output ports of multiplexer 234 are tied to the three coils 86*b*, 88*b* and 90*b* of transmitter assembly 84.

A microcontroller 236, again internal to the tracker 32, both controls the emission of energy from the transmitter assemblies 82 and 84 and is the component that initially monitors the energy detected by bone marker transducer 66.

Specifically, microcontroller 236 asserts a control signal to multiplexer 234 to tie the signals from the signal from the generator-amplifier pairs to either transmitter assembly 82 or transmitter assembly 84. Microcontroller 236 also asserts individual control signals to amplifiers 118. Thus, microcontroller 236 regulates the gain of the individual signals applied to the transmitter assembly coils.

Microcontroller 236 receives as input signals the signals emitted by transducer assembly coils 92, 94 and 96. Prior to being input to the microcontroller 236 these signals are individually amplified by amplifiers 116 and 118 and digitized by ADC 120.

The alternative tracker of FIG. 8 also contains the previously described LEDs 122, transceiver 130 battery 134 and related components.

In this version of the invention, when it is time to execute step 168, the emission of EM energy from the transmitter assembly 82, microcontroller 236 first asserts a control signal to the multiplexer 234 to tie the multiplexer inputs to the individual coils 86*a*, 88*a* and 90*a*. The gains of the individual amplifiers 228, 230 and 232 are set individually. Thus, coils 86*a*, 88*b* and 90*a* emit EM waves of appropriate strength.

When the check procedure of steps 196 and 198 are to be performed, microcontroller 236 asserts a control signal to multiplexer to cause the output drive signals to be applied to coils 86*b*, 88*b* and 90*b* of transmitter assembly 84.

Figure 9:
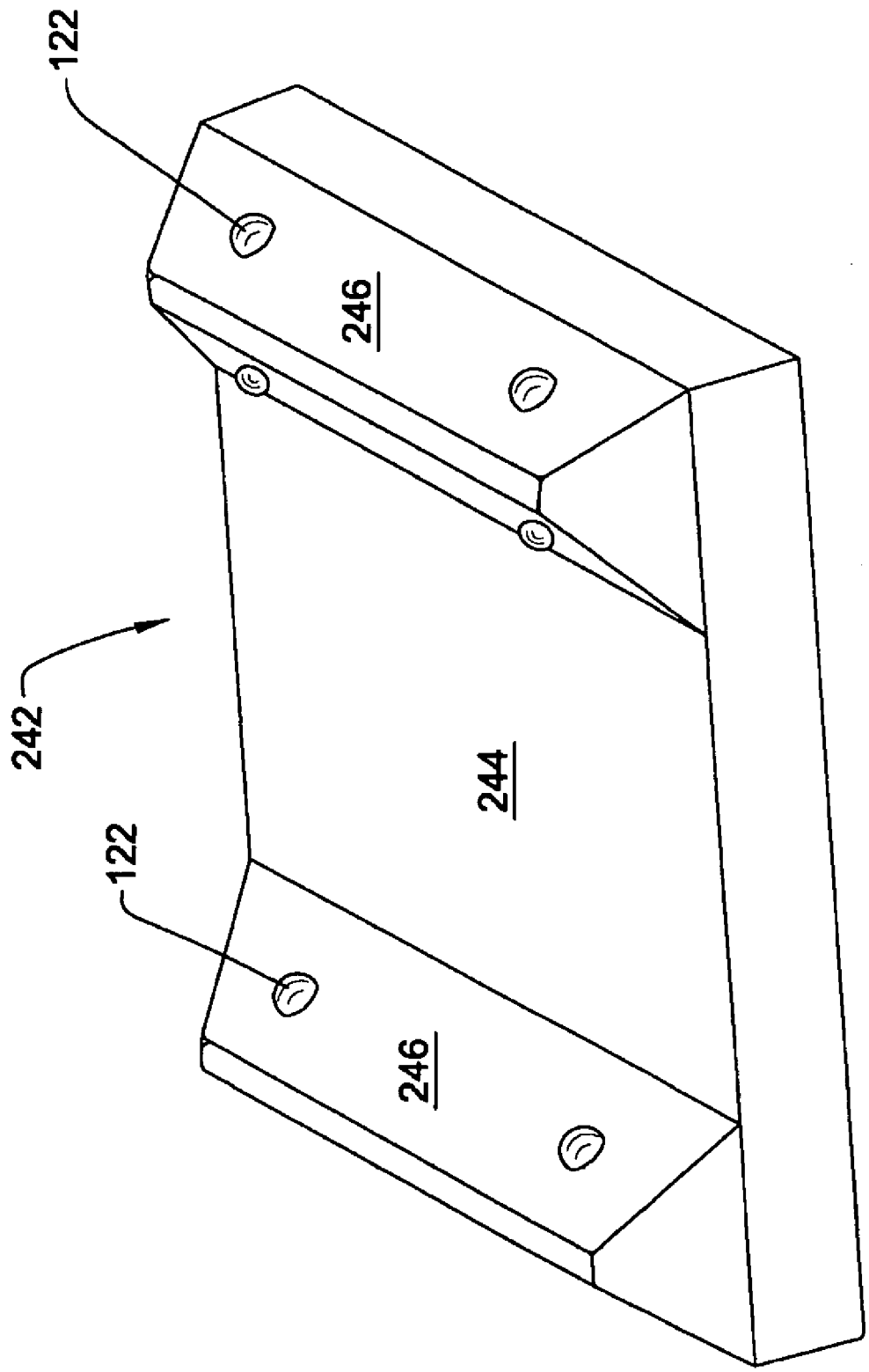
FIG. 9 is a perspective view of the structure of an alternative tracker of this invention.

FIG. 9 is a perspective view of an alternative tracker 242 of this invention. Tracker 242 has a body 244 that is generally rectangular. Tracker body 244 is further formed to have along the top surface thereof two ribs 246 that have a generally triangular cross sectional profile. Each rib 246 extends laterally across one end of the tracker. The LEDs 122 are mounted to ribs 246 such that there are two LEDs on the side of each rib.

Figure 10:
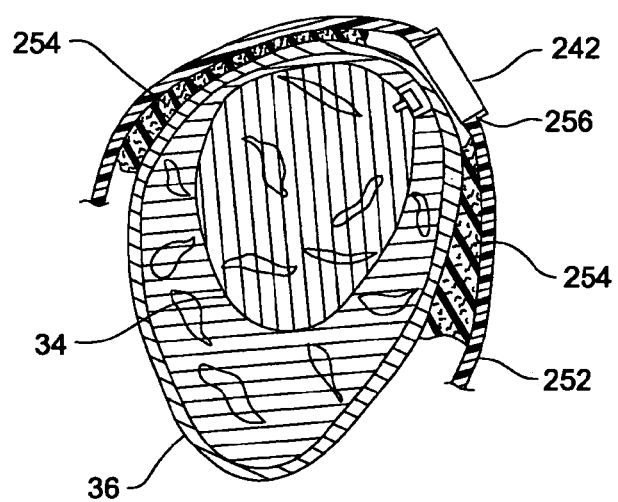
FIG. 10 is a partial cross sectional view depicting how the tracker of FIG. 9 may be fitted to the body.

Tracker 242 is held to the body portion adjacent the underling bone marker 38 by a shaped strap 252 seen in FIG. 10. Strap 252 is formed from a plastic and is C-shaped so that it can be compression fitted around the body portion. Foam padding 254 around the inner surface of strap 252 provides a cushion between the strap and underlying skin 36. The outer surface of the strap is formed with a rectangular shaped outwardly extending web 256. Web 256 defines an opening (not identified) in which the tracker 242 is seated.

It should likewise be appreciated that in alternative versions of the invention, transducer assembly may have transducer elements other than coils. In some versions of the invention, the EM sensitive devices may be Hall sensors or magneto-resistive sensors.

Further, the locations of the components may vary from what has been described. In some versions of the invention, it may be desirable to place a transmitter assembly in the bone marker 38 and one or more sensor assemblies in the tracker.

Likewise, in other versions of the invention, the amount of processing of the EM sensor signals performed in the tracker may vary from what has been described. In some versions of the invention, there may be essentially no processing of the sensor signals in the tracker except what is needed to transmit them to the system processor 44. In still other versions of the invention, these signals may be completely processed by the processing unit internal to the tracker. Thus, step 188 is performed entirely by the tracker processor. Upon completion of this step, vector $\vec{x}_{T \to M}$ and rotational matrix $R_{T \to M}$ are transmitted by the tracker to the receiver internal to the localizer 40.

IV. Second Alternative Tracker

Figure 11:
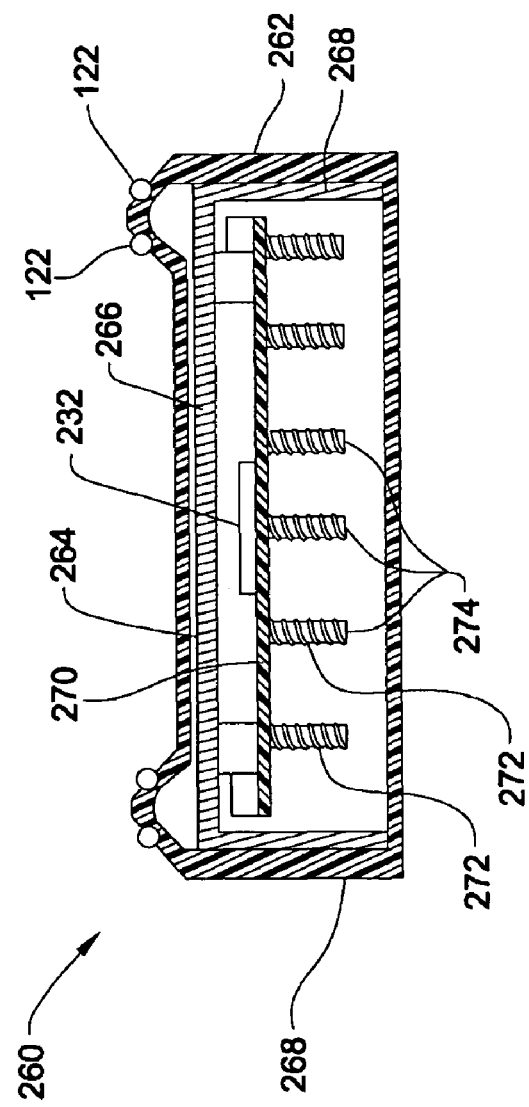
FIG. 11 is a cross sectional view of a second alternative tracker of this invention.

FIG. 11 illustrates still another tracker 260 of this invention. Tracker 250 is formed to have a housing 262. Internal to housing 262 is a shell 264 formed from a thin layer of ferromagnetic material. Shell 264 is formed to have base 266 immediately below the top of housing 262. The shell 264 also has side walls 268 (two shown) that are formed integrally with the base 256 and extend downwardly from the perimeter of the base. Shell 264 thus defines a void space that is directed toward the surface of the body section in which the bone marker 38 is mounted.

Internal to the shell void space is a substrate 270. Either the transmitting assembly or sensor assembly of the EM navigation system is suspended from the void space. In FIG. 11 an array of downwardly directed coils 272 represent the transmitter assembly or sensor assembly internal to the tracker. Each of the coils is wrapped around a post 274 that extends downwardly from the substrate 270

In the above described tracker of this invention, shell 264 functions as shield that prevents ambient electromagnetic waves from entering the space between the tracker 260 and bone marker 38. This construction makes it possible to place ferromagnetic devices relatively close to the tracker 250 without the concern that such devices could interfere with the accuracy of the EM based measurements of the position and orientation of the bone marker.

FIG. 11 illustrates another alternative feature of this invention. There is no requirement that the transmitter (sensor) array comprises a set of emitters (transducers) arranged in three dimensions. In some versions of the invention the transmitter (sensor) array can include a plurality of emitters (transducers) that are arranged in a common dimension. Such construction may also be incorporated into the emitters (transducers) internal to the marker.

V. First Alternative Marker

Figure 12:
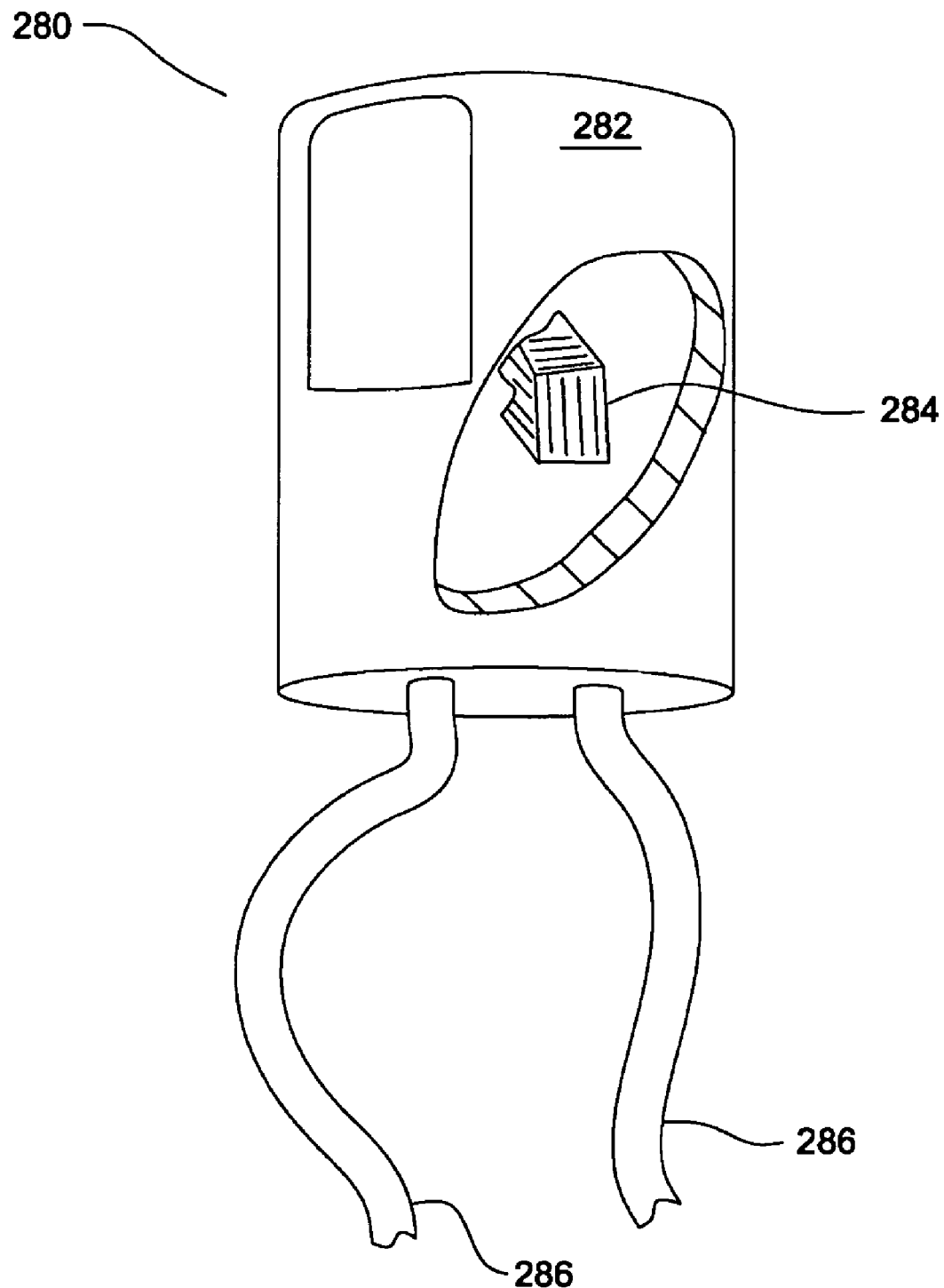
FIG. 12 is a perspective view of an alternative marker of this invention.

It should likewise be understood that the navigation system of this invention is not limited to systems used to tracker hard tissue, bone. In alternative versions of the invention, the tissue marker is provided with features that allow it to be secured to soft tissues, such as muscles, ligaments, tendons and the diaphragm. FIG. 12 illustrates one such marker 280. Here marker 280 has a head 282. Internal to the head is the transmitting assembly or sensor assembly. In FIG. 12, coil block 284 represents the transmitter or sensor assembly.

Two legs 286 formed of bendable metal or plastic extend downwardly from marker head 282. Marker 280 is fitted to the soft tissue by inserting legs around the tissue adjacent the marker. Legs 286 are pressed together so that the legs clamped around the tissue to hold the marker in position.

Thus in procedures other than orthopedic surgical procedures, the system of this invention can be used to track the position and orientation of body tissue while only requiring the minimal invasion of the body and the minimal transmission of energy through the body.

VI. EM-Based Navigation Frequency Hopping

Figure 13A:
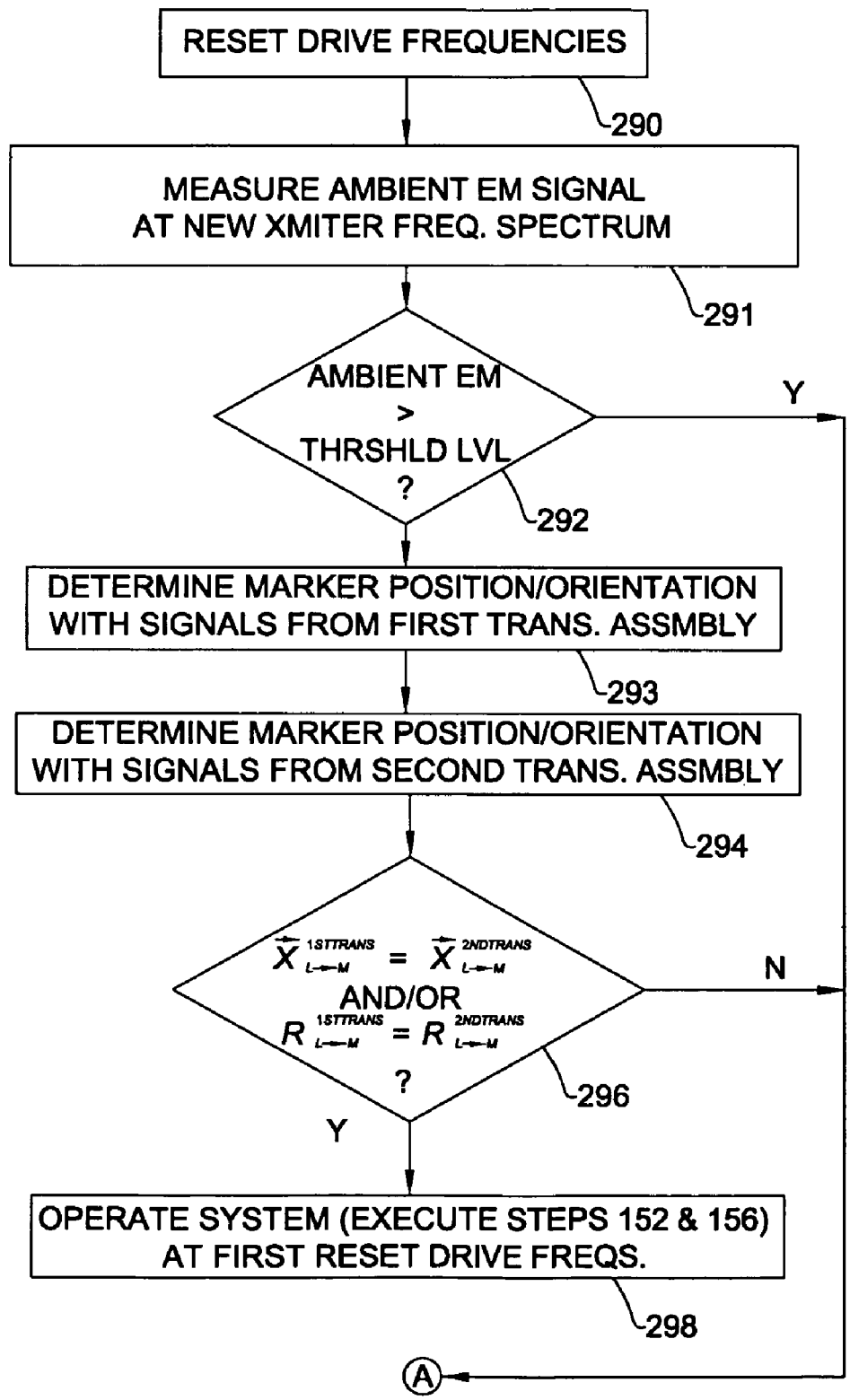
FIGS. 13A and 13B, when assembled together, form a flow chart of the frequency shifting process performed by the system of this invention in order to operate when spurious electromagnetic waves are present.
Figure 13B:
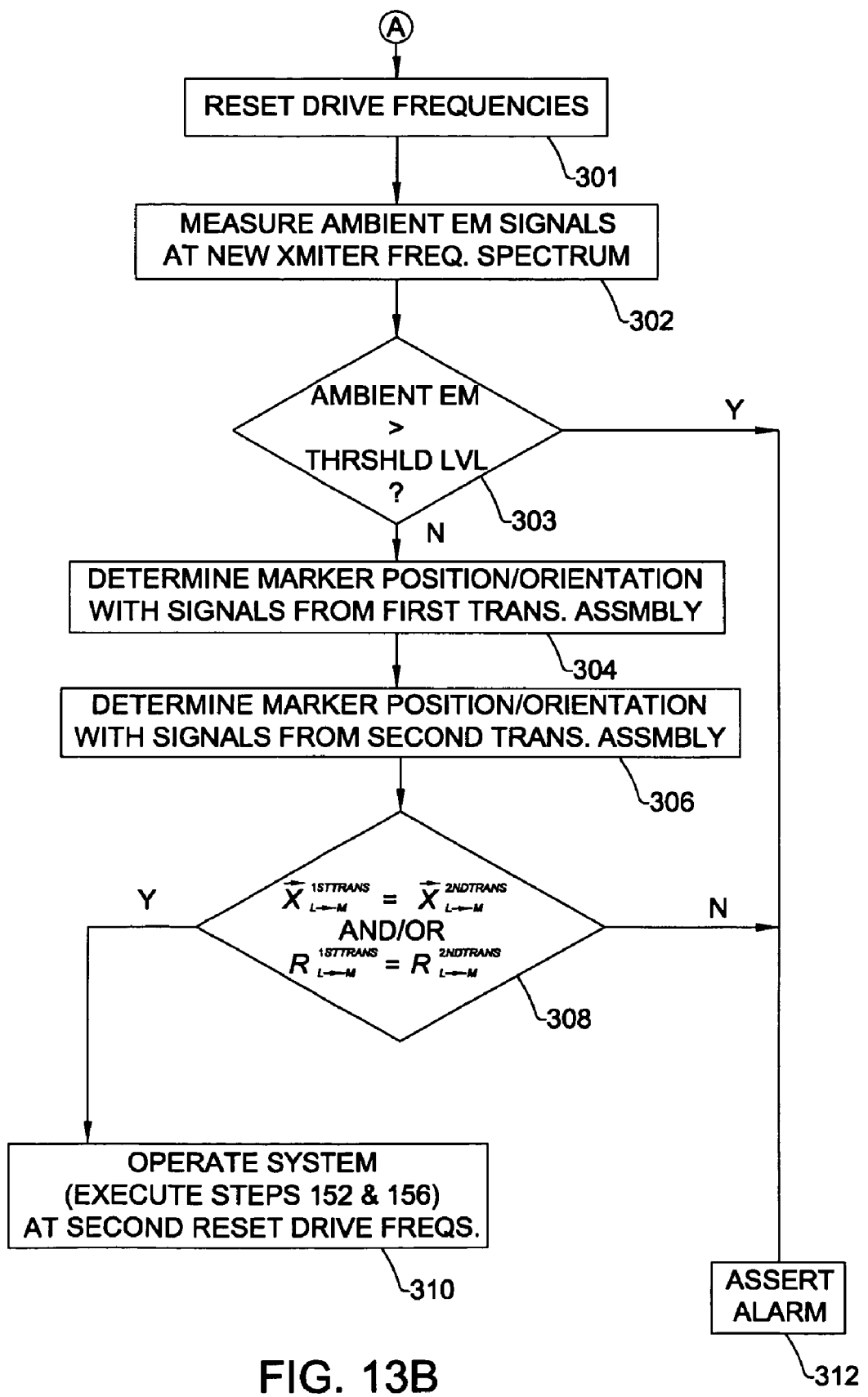

Further, as now described by reference to FIGS. 13A and 13B, system 30 of this invention is also configured to operate in a certain situations when ambient EM signals would otherwise adversely affect the accuracy of the marker/tissue position and orientation determinations. As discussed above with respect to step 156 (FIG. 7) and steps 196-204 (FIG. 7D), system 30 determines whether or not the position and orientation data generated are accurate by comparing the determinations made based on signals generated by the separate transmitter assemblies 82 and 84.

In some situations, the position and orientation data are inaccurate because a nearby medical device, such as a power drill or other instrument with a motor, emits EM signals. Generally, the frequency at which this other device functions as an EM signal generator varies with its operating rate. Therefore, there is no exact way to automatically compensate for the presence of the EM signals emitted by the device.

Accordingly, once, in step 202 (FIG. 7D), it is determined that the position and orientation data generated by the system 30 are inaccurate, system 30 attempts to find a set of frequencies at which it can operate at which the ambient EM signals will not adversely affect the position and orientation determination. As seen by FIG. 13A, this process starts, in step 290, with the resetting of the drive frequencies at which the transmitter assembly coils 86a-90a and 86b-90b are driven. The actual reset command it should be appreciated originates with the system processor 44 and is transmitted through the transceiver 130 the tracker microcontroller 108. For example, in one version of the invention, three coils of transmitter assembly 82 or 84 are, for example, are normally driven at frequencies of 570 Hz, 630 Hz and 690 Hz. In step 290, these frequencies are reset to, respectively 870 Hz, 930 Hz and 990 Hz. Each frequency is adjusted by a constant offset.

Then in steps 291 and 292 system performs an ambient EM noise check. This sub-process starts with the system, in step 291, measuring the strength of the ambient EM energy detected by sensors (coils) 92, 94 and 96. More particularly, the system measures the ambient EM energy present in the frequency spectrum in which transmitters 82 and 84 are set to operate. These measurements are performed by monitoring the voltage across each coil 92, 94 and 96 during a period in which the complementary tracker transmitters 82 and 84 are both switched off.

In step 292, processor 44 compares the strength of the ambient EM energy to a threshold energy level. This threshold level depends on the sensitivity and noise properties of the sensors and the strength of the magnetic field generated by the transmitters. Generally, the transmitted signal to noise ratio needs to be at least 100:1 and, more preferably, 300:1 or more. In one system, with a 45 milliamp driving current through one coil of a 0.5 cubic inch transmitter, at 4 inches away from the transmitter assembly 82 or 84, the magnetic field is as low as 6 milliGauss. In this environment, the threshold value is a maximum of 60 microGauss and, more preferably, 20 microGauss or less.

If the comparison of step 292 indicates the ambient EM energy level at the reset output frequency spectrum for the transmitters is less than the threshold level, the environment is considered to be one in which the ambient EM signals would most likely not affect the operation of the system 30. Accordingly the system proceeds to perform a second sub-process to further ensure the subsequently generated tracker position/orientation data will be accurate. This sub-process starts with the below described step 293. However, in step 292 it may be determined that the ambient EM signals at the new transmitter frequency spectrum are above the threshold level. This means the ambient EM signals could adversely affect the generation of accurate position and orientation data. In this event, system 30 performs a second frequency hop, frequency resetting, described below with respect to step 301.

In step 293, the system determines the position and orientation of the marker based on the detection of drive signals applied to the coils 86a-90a of the first transmitter assembly 82. In a step 294, the system determines marker position and orientation of the marker based on the detection of drive signals applied to coils 86b-90b of the second transmitter assembly 84. Again, in some versions of the invention, steps 292 and 294 are performed simultaneously.

Once steps 292 and 294 are executed, the marker position and orientation determinations based on the signals from the two different transmitter assemblies 82 and 84 are compared, step 296. Thus, step 296 is similar to the determination of step 202. If the position and orientation data are identical, then the EM signals interfering with EM signals generated by system 30 within the frequency range is not interfering with the system's EM signals emitted at the second frequency range. Accordingly, as represented by step 298, the system continues to operate, steps 152, 154 and 156 are again cyclically executed. However, at this time the tracker drives the transmitter assembly coils at the frequencies of the reset frequency range.

Alternatively, from the evaluation of step 296, it may be determined that system is still not accurately tracking the position and orientation of the marker 38. In this situation, the system proceeds to the second resetting of the range of the drive signals applied to the transducers, step 301. In the present example, the range of frequencies is downshifted by an amount two that they were up-shifted. Thus, the drive signals are applied to the individual transmitter coils at frequencies of 270 Hz, 330 Hz and 390 Hz.

Once step 301 is executed a measurement of ambient EM signal strength at the new frequency spectrum is made as represented by step 302. In a step 303 the measured ambient EM signal strength is compared to the threshold value. Steps 302 and 303 are thus similar to, respectively, steps 291 and 292. If, as a result of the execution of step 303, it is determined that significant EM signals are present at this second reset frequency spectrum, an alarm may be asserted, step 312.

However, in step 303 if it is determined that strong EM signals that could potentially affect the position and orientation determinations are not present in the ambient environment, the system proceeds to execute a sub-process to determine if the EM signals transmitted within the new spectrum can be used to provide accurate position and orientation data. This sub-process starts with step 304.

In step 304, the position and orientation of the marker 38 is determined based on the second set or reset drive signals applied to coils 86a-90a of the first transmitter assembly 82. In a step 306, system 30 determines marker position and orientation of the marker based on the detection of drive signals applied to coils 86b-90b of the second transmitter assembly 84. Again, steps 304 and 306 may be performed simultaneously.

A step 308 is then executed to compare the two marker position and orientation determinations. Thus, step 308 is, like step 296, similar to step 202. If the determinations are identical, then the system is generating transmitter assembly drive signals within a frequency range at which the ambient EM signals are not adversely affecting the measurements made by transducer 66. In this situation, as represented by step 310, the system returns to normal operation. At this time though, the microcontroller 108 causes the transmitter assembly coils to be driven at frequencies within the second reset frequency range.

However, the determination of step 308 may test false. Thus, collectively as a result of the tests of steps 202, 296 and 308 it is apparent that the ambient EM signals are within a very wide frequency range. In this situation, it may not be possible for the system to continue to accurately generate marker/tissue position data. Therefore, system 30, in a step 312, asserts an alarm indicating that the ambient EM signals have such characteristics that they system cannot operate at its transmitter assemblies at any frequencies in order to ensure the accurate generation of position and orientation data.

It should be appreciated that the foregoing is only one potential frequency shifting protocol of this invention. In some versions of the invention, system 30 may only make a single frequency shift to find a range of operating frequencies at which it can operate free from ambient EM signal interference. In other versions of the invention, system 30 makes three or more shifts before determining the ambient EM signals are of such strength and/or within such a range that the system cannot provide accurate market and position and orientation data. The 300 Hz shift up and down from the base frequency range should understood to be exemplary, not limiting.

Figure 14:
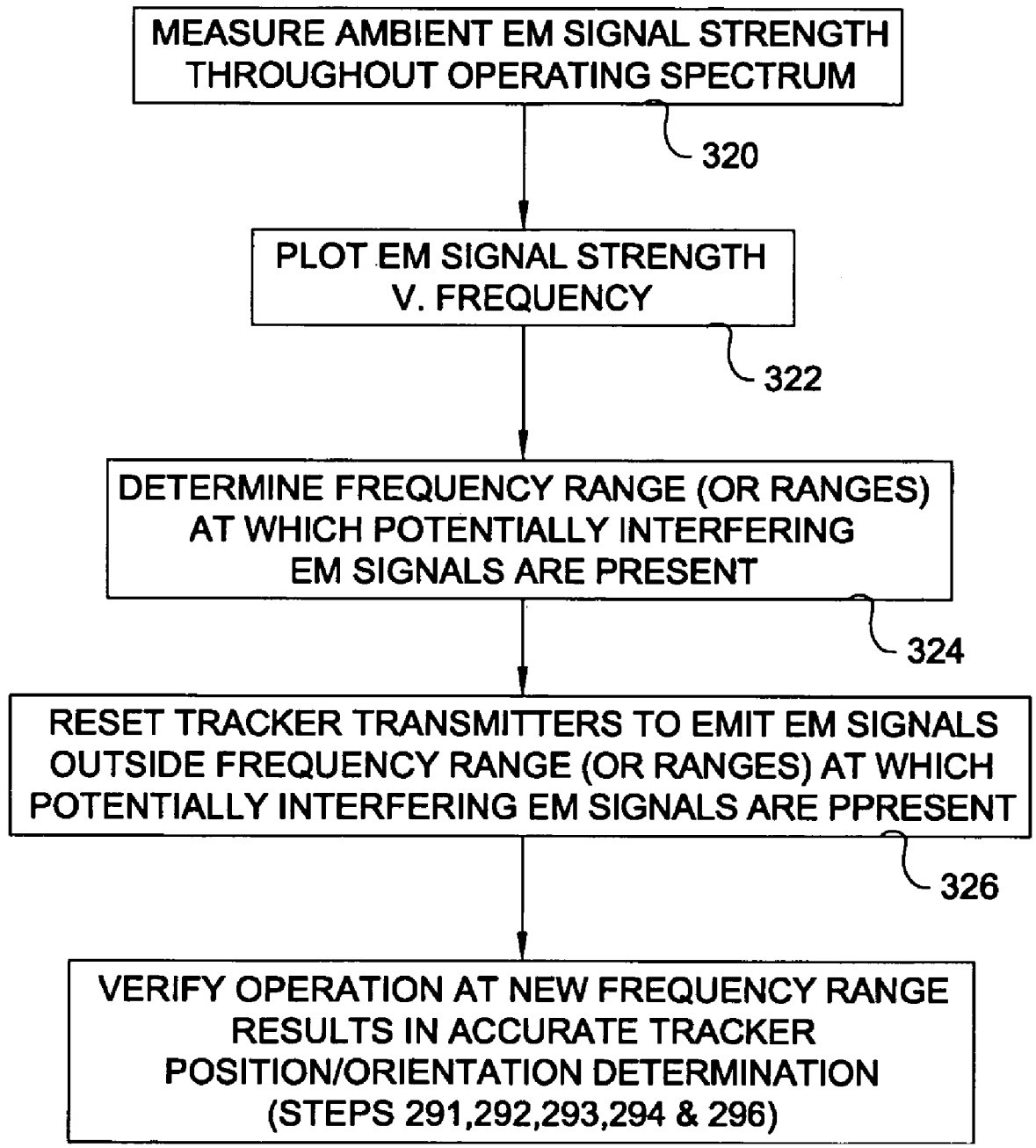
FIG. 14 is a flow chart of the process steps executed by the system of this invention to determine at which range of frequencies the electromagnetic signals should be emitted in order to determine the position and orientation of the tracked bone marker.

FIG. 14 illustrates an alternative process by which system 30 of this invention by which system processor 44 resets the frequencies at which tracker transmitters emit EM signals if there are significant ambient EM signals within the first operating spectrum. In a step 320, system 30, through the marker sensors (coils) 92, 94 and 96 measures the ambient EM signals throughout the complete frequency spectrum in which transmitters 82 and 84 emit EM energy. This process may be accomplished by Fast Fourier Transformation or any other spectral analysis technique for determining the frequency of the emitted signals.

Figure 15:
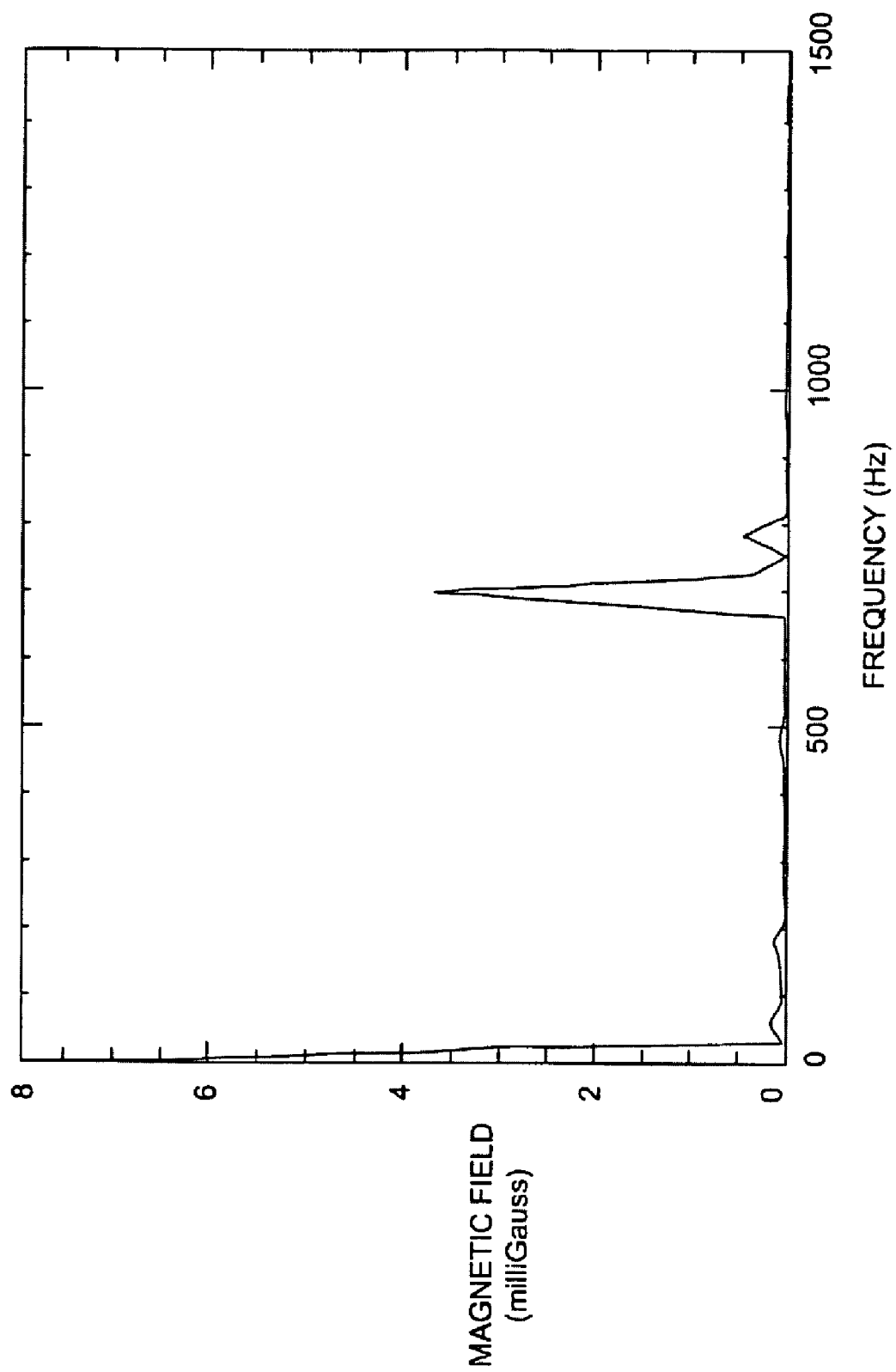
FIG. 15 is a plot of the levels of the ambient EM signals that may be measured in the process of FIG. 14.

As a consequence of step 320, system processor 44 generates an internal plot of the strength of the ambient EM signals throughout the spectrum, step 322. FIG. 15 is a graphic representation of this plot. Here, the relative strengths of the ambient above noise level EM signals range from 0 to approximately 3.5 milliGauss. In this particular case, the noise generator is a surgical saw. Often, an EM signal generator adjacent the surgical site at which the system 30 is used emits EM signals within a defined frequency range or ranges. In FIG. 15 this is represented by the fact that the ambient EM signals are above nominal noise levels at frequencies below 200 Hz and between approximately 650 and 850 Hz.

Consequently, based on the data plot generated in step 322, in a step 324, system processor 44 determines the frequency range (or ranges) at which potentially interfering ambient EM signals are present.

Then, in a step 326, system processor 44 generates commands to cause the frequencies at which the transmitter assemblies 82 and 84 emit signals to be reset to a range outside those at which the interfering EM signals are present. This step may be considered similar to step 290 (FIG. 13A). The system may then perform steps similar to those described in FIGS. 13A and 13B to ensure that the transmission and complementary sensing of the signals within the reset frequency range will cause accurate tracker position and orientation data to be generated.

VII. Integrated EM Navigation and Device Operation

Figure 16:
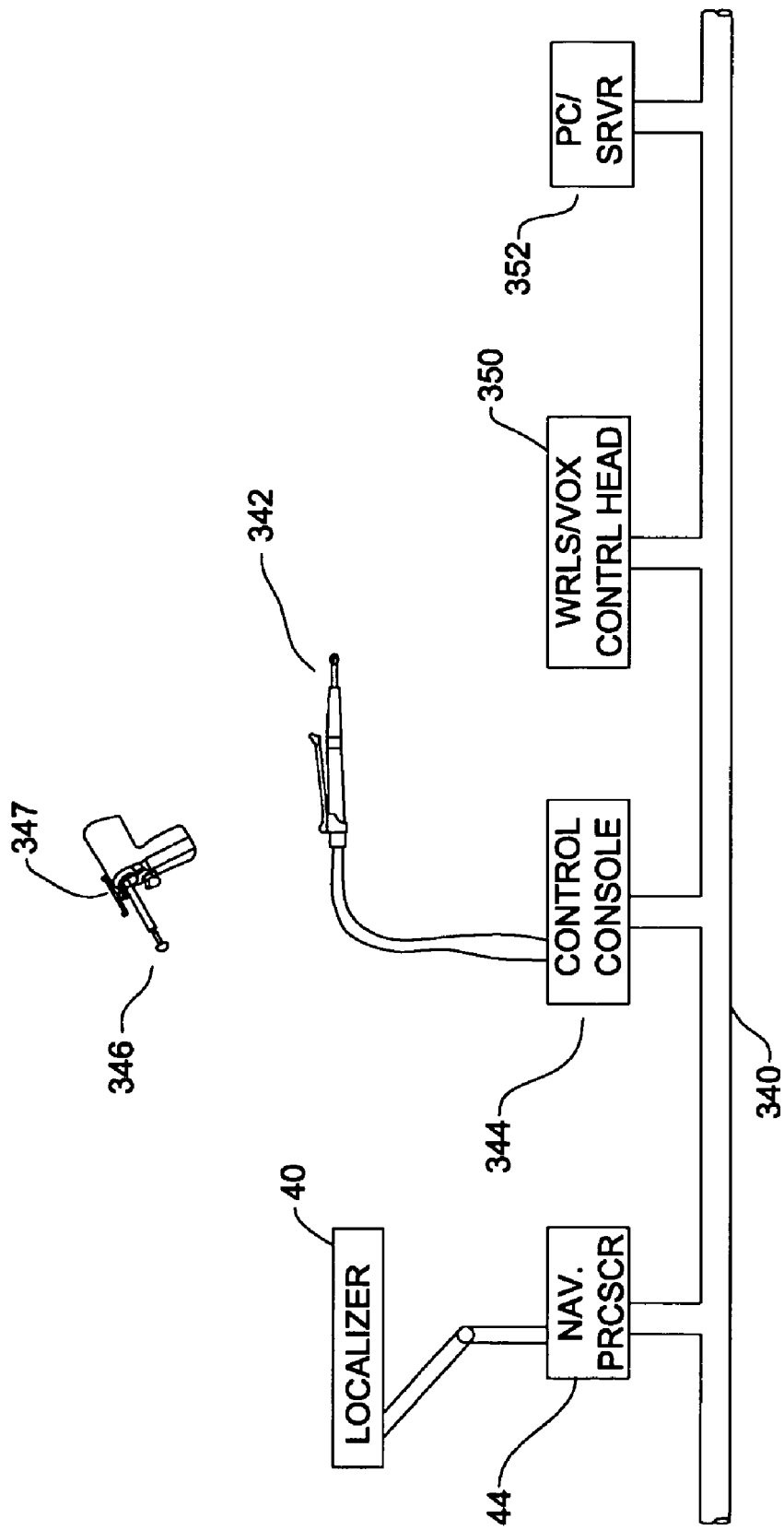
FIG. 16 is a block diagram of how the navigation system of this invention is networked to other devices in the operating room in which the system is used, including both corded and cordless power tools.

As illustrated by FIG. 16, it is further possible to integrate system 30 of this invention with the other devices employed in the operating room. More particularly, system 30 is integrated to operate in unison with the devices, such as the power tools that can emit potentially interfering EM signals. In FIG. 16 system processor 44 of this invention is connected to a bus 340 to which other devices are connected. These devices include a control console 344. Console 344 generates energization signals to corded powered tools such as handpiece 342. Such control consoles are discloses in the Applicants' Assignee's U.S. Pat. No. 6,017,354, INTEGRATED SYSTEM FOR POWERED SURGICAL TOOLS, issued Jan. 25, 2000 and its U.S. patent application Ser. No. 10/955,381, INTEGRATED SYSTEM FOR CONTROLLING PLURAL SURGICAL TOOLS, filed Sep. 30, 2004, U.S. Pat. Pub. No. US 2006/0074405 A1, the contents of both documents now incorporated herein by reference. Still another device that may be connected to bus 340 is a wireless/voice control head 350. This type of device is capable of receiving spoken commands and/or commands entered through a wireless control pendant. Control head 350, upon receipt of the command, converts it into a processor-executable instruction that can be processed by control console 344. In this manner, head 350 allows the surgeon to enter spoken or touch command in order to regulate the operation of handpiece 342. One such control head 350 is sold by the Applicants' Assignee under the trademark SIDNEE.

Another processing unit that can be attached to bus 340 is a personal computer or a server 352. Either unit can perform the data processing, including the data process described below with respect to the process of FIG. 17. Providing this additional processing unit minimizes the data processing other units such as navigation processor 44 or the processor internal to control console 344 are required to perform.

Bus 340 is any suitable bus over which data and commands can be exchanged between multiple processing units. The bus may be any bus such as an IEEE-1394 Firewire bus or LAN.

Cordless power tools are also connected to system 30. One such power tool, a cordless driver 346 is depicted in FIG. 16. The Applicants' Assignee's U.S. Patent Application No. 60/694,592, POWERED SURGICAL TOOL WITH SEALED CONTROL MODULE, filed Jun. 28, 2005, refilled as U.S. patent application Ser. No. 11/472,012, POWERED SURGICAL TOLL WITH CONTROL MODULE THAT CONTAINS A SENSOR FOR REMOTELY MONITORING THE TOOL POWER GENERATING UNIT, U.S. Pat. Pub. No. 20070085496, now U.S. Pat. No. 7,638,958, the contents of which are incorporated herein by reference, discloses how a cordless tool can, through a tracker 347 attached to the tool and the localizer 40 transmit real time operating data to navigation processor 44.

Figure 17A:
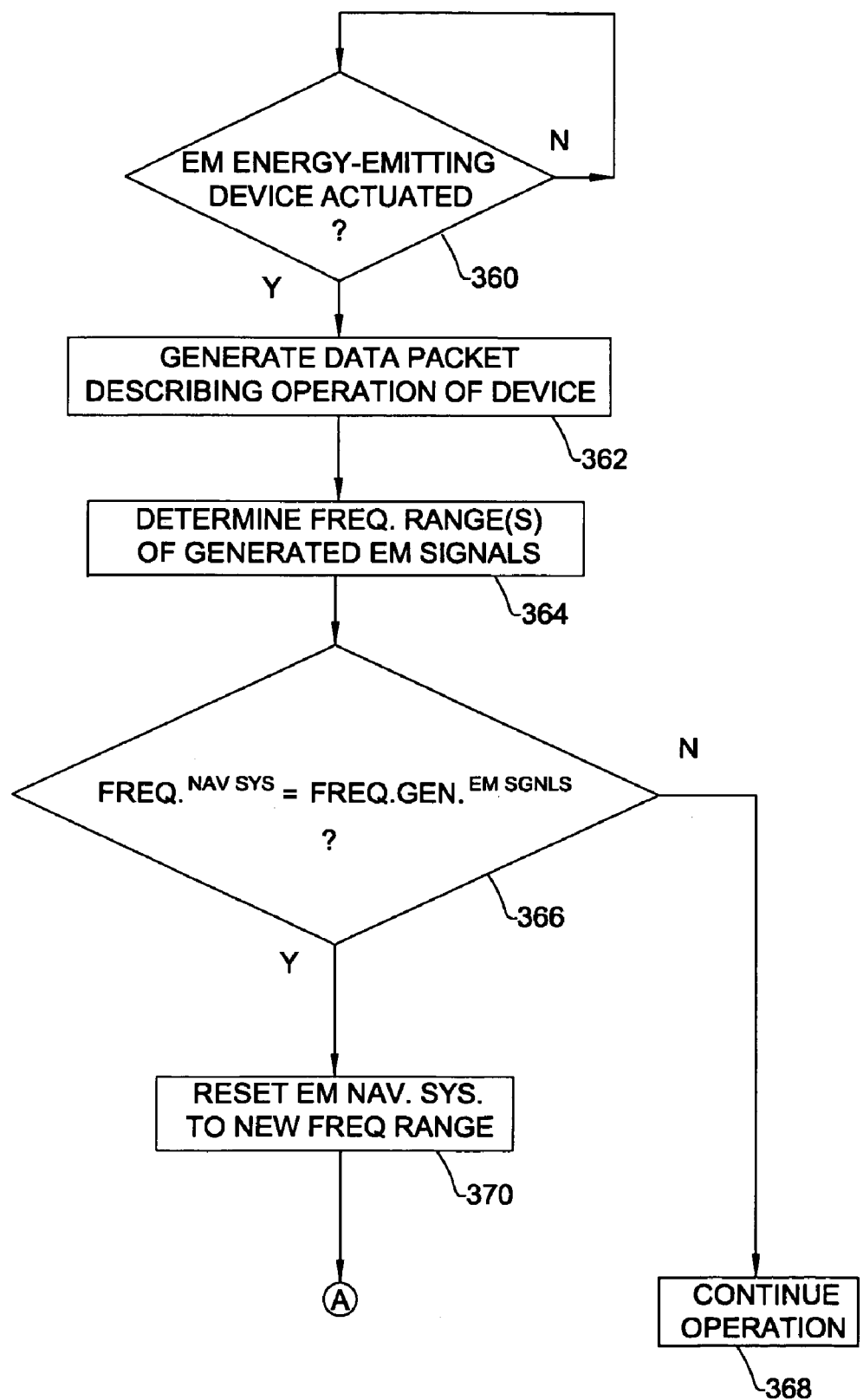
FIGS. 17A and 17B collectively form a flow chart of the process steps executed by the EM navigation system of this invention to adjust for the presence of device-generated EM signals in the ambient environment.
Figure 17B:
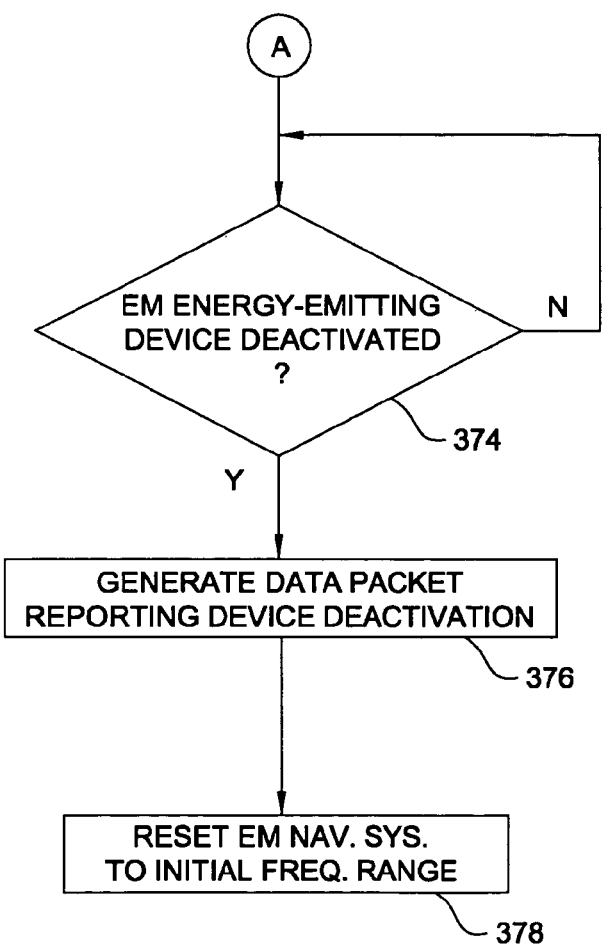

FIGS. 17A and 17B form a flow chart of the process steps executed by the integrated system of this invention. Step 360 represents the initial step of waiting to see if device that generates EM signals is actuated. Such device could be the motor internal to corded handpiece 342 or the motor internal to the cordless driver 346. Again, it is recognized by those skilled art that other surgical power tools not just motorized tools can be the source of EM signals. Such tools include, and are not limited to, RF ablation tools, laser and other light emitting tools, and devices that emit sonic or ultrasonic energy. Accordingly, the type of EM signal-emitting surgical device is not limited to one specific type of device.

When in step 360, the EM energy emitting device is actuated, a data packet describing the operation of the device is generated, step 362. This data packet, in addition to containing data indicating that the device is actuated, describes the characteristics of the operation of the device. For example, if the device is a motorized power tool, the data packet describes the speed of the motor. The unit of the integrated system that generates this data packet is a function of the specific type of device. For example, if the device is a corded tool, control console 344 generates this data packet and places the packet on bus 340. If the device is cordless, a processor internal to the device generates the packet and transmits the packet to the complementary transceiver 132 (FIG. 1) internal to localizer 40.

Based on the describing the operation of the device, in a step 364, the frequency range of EM signals generated by the device is determined. For example, for a motorized tool, there is generally a proportional relationship between motor shaft RPM and the frequency at which EM signals are emitted. The exact relationship can be determined by empirical analysis. Step 364, depending on the configuration of the system, it should be understood, can be performed by either the navigation system processor 44 or the network (operating room) computer/server 352.

Then, in a step 366 a determination is made whether or not the frequency range at which the navigation system 30 is emitting EM signals approximates the range at which the device is generating EM signals. In some versions of the invention, the processor that executes step 364 also executes step 366 and the below described steps 370, 376 and 378. If, in step 366, it is determined that the device is generating EM signals within a frequency range whole different from the range at which system 30 is generating EM navigation signals, operation of the navigation system continues as before, step 368.

Alternatively, in step 366 it may be determined that the present EM frequency range at which the navigation system 30 is operating is at least partially overlaps or is relatively close to the frequency at which the powered device is emitting EM signals. If this condition exists, in step 370 the navigation system 30 resets the frequency range at which the transmitter assemblies emit EM signals to the marker 38. Again, the instructions to reset the operating range of the transmitter assemblies may be generated by any suitable processor such as the navigation system processor 44 or the operating room computer/server 352.

Navigation system 30 continues to operate at the reset range of frequencies. Eventually, the EM generating device is deactivated, step 374. When this happens the processor associated with the device, in step 376 outputs a data packet reporting the device deactuation. In response to the receipt of this packet, the device responsible for establishing the operating frequencies of the navigation system, in step 378, resets the navigation system so that it operates at its initial frequency range.

Thus, the integrated system of this invention is constructed so that, as soon as the device starts to generate potentially interfering EM signals, the frequency of these signals is determined. If, in fact, the device-generated EM signals could adversely affect the operating of the navigation system 30, the operation of the navigation system is reset so it outputs EM signals at a different frequency. This substantially reduces the possibility that the generation of EM signals by a surgical device in the vicinity of the navigation system 30 could result in the system 30 generating potentially inaccurate marker position and orientation data.

VIII. Second Alternative Marker

Figure 18:
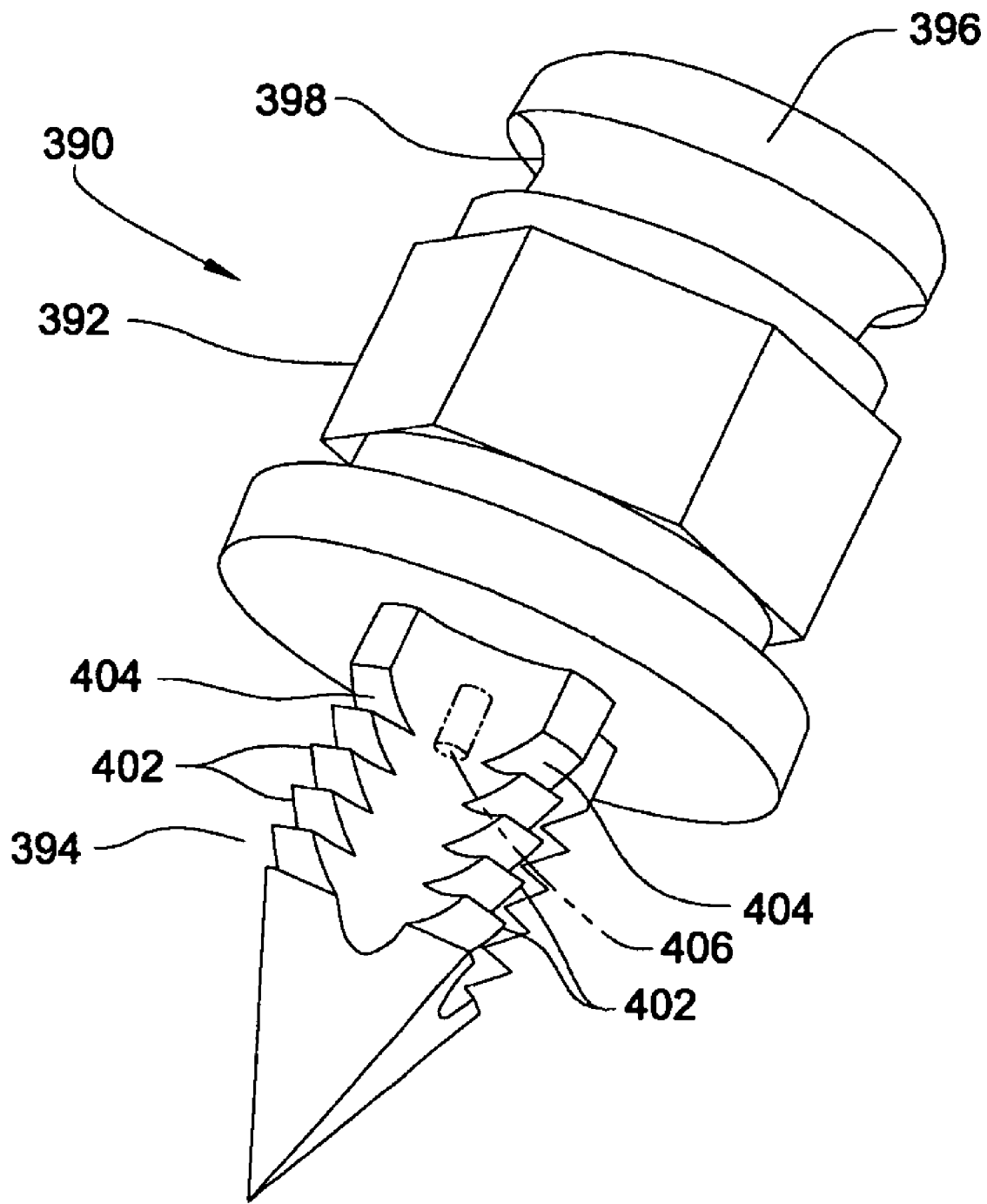
FIG. 18 is a perspective view of another alternative marker of this invention.

FIG. 18 illustrates still another marker 390 of this invention. Marker 390 has a head 392 from which a stem 394 extends. Head 392 contains the previously described transducer 66 (FIG. 3). Head 392 is formed to define a topmost crown 396. Crown 396 has a surface that, from the top of the head curves outwardly toward the side of the head. Below crown 396, the head is formed to define a groove 398 that extends inwardly relative to the outer perimeter of the crown. Both the crown 396 and the groove 398 extend circumferentially around marker head 392.

The above geometry is provided to facilitate the fitting of a removal tool to the marker 390. Specifically it should be understood, that once marker 390 is fitted to the bone, it may not be possible to visually detect the marker. Making a larger incision to facilitate marker removal reduces one of the advantages of this invention, that the marker can be fitted without exposing the patient's tissue to appreciable trauma. The removal tool is therefore often attached to the marker by feel. The tool itself typically has a number of legs that are configured to be biased together around the marker head 392. When the removal tool is, by tactile probing, fit over the marker head 392, the legs when extending over the crown 396. Further insertion of the legs over the head result in the legs snapping into groove 398. This movement provides the surgeon with tactile and audible feedback that the removal tool is properly position over the marker head 392.

Stem 394 of marker 390 is formed to have a number of barbs 402. More particularly, there are four longitudinal rows of barbs 402. The barb rows, (two shown) are equangularly spaced apart. Upon insertion of the marker stem 394 into the bone, barbs 402 dig into the bone to hold the marker 390 in position.

Stem 394 is further constructed so that immediately above the proximal most barbs 402 there are indentations 404 that extend substantially inward of the barbs. Indentations 404 thus define adjacent the proximal end of the stem 394 a separation zone along axis of the stem represented in FIG. 18 by a phantom cylinder 406. Structurally, the separation zone has, in comparison to the rest of the barb, a low tensile strength. For example, in some versions of the invention, the material forming the separation zone may separate if the stem 394 is exposed to tensile force, a pulling force, of 50 pounds or more. In still other versions of the invention, the stem separates when exposed to a force of 80 pounds or more or 100 pounds or more. In practice, markers with stems with a separation zones that separate upon the application of different amounts are force are provided. At the start of the procedure, step 160 (FIG. 7A) a marker with a stem separation zone that separates upon the application of a specific force is then fitted to the patient as a function of such variables as bone density, bone age and bone size.

At the completion of the procedure in which system 30 is used, marker 390 is removed. More particularly, the removal tool is attached to the marker head 392. Force is then used to remove the marker 390. This force may exceed the tensile strength of the separation zone of the stem 394. In this situation, the material forming the separation zone separates. Thus, in this procedure, the marker head 392 and proximal end of the stem 394 are removed from the surgical site; the portion of the stem 394 distal to the separation zone remains embedded in the bone.

An advantage of the foregoing marker construction is that the removal of the marker 390 does not expose the hard tissue, bone, surrounding the marker to appreciable trauma. Since the stem 394 is formed from biocompatible material, leaving of the stem distal end section in the patient does not have any adverse affects.

IX. Alternative Marker Sensors

It should likewise be appreciated that the transducer elements used to measure the signals transmitted through the body may vary from what has been described.

For example, as an alternative to the coils, magnetoresistive devices may be used to measure the strength of EM signals. It is believed that these transducer elements are less affected by noise induced from such sources as thermal noise.

As seen in FIG. 19, in this version of the invention two magnetoresistive sensors 410 and 412 are mounted on a common flex circuit 416. Flex circuit 416 has a generally elongated shape to, as discussed below, facilitate the seating of sensors 410 and 412 in the marker. Conductors 415 that provide energization signals to sensors 410 and 412 and that supply the signals from the sensors are also disposed on the flex circuit 416. Sensors 410 and 412 are located near the distal end of the flex circuit 416 and are equidistantly spaced apart from the longitudinal axis of the flex circuit. It is further observed that the flex circuit 416 is formed to have a slot 418 that extends rearwardly from the distal end of the circuit. Slot 418 is located along the longitudinal axis of the flex circuit so that the individual sensors 410 and 412 are on opposed sides of the slot.

When the marker in which sensor 410 and 412 are employed is assembled, the distal end of the flex circuit 416 is folded around slot 418 so that the two opposed sections are, as seen in FIG. 20, at 90° to each other. Each sensor 410 and 412 includes two sensing assemblies (not illustrated) that are themselves at 90° to each other. Thus as result of the bending of the substrate supporting the sensors 410 and 412, there is at least one sensor assembly for measuring EM field signals along each of the x-, y- and z-axes. This is seen in FIG. 20 where arrow 420 through sensor 410 represents that internal to that sensor there is a sensor assembly capable of measuring EM signals along the x-axis; to the left and right in the drawing sheet. Arrow 422, also through sensor 410, represents that the second sensing assembly of sensor 410 is capable of measuring EM signals along the z-axis; up and down in the drawing sheet. Arrow 424, through sensor 412, represents that, due to sensor 412 being at a 90° angle to sensor 410, sensor 412 has a sensing assembly sensitive to EM signals in the y-axis; in and out of the drawing sheet. A potting compound, a fixture close tolerances and/or angled brackets can be used to hold the distal end sections of the flex circuit 416 to ensure that the sensor maintain the proper orientation relative to each other.

An alternative version of this invention includes a single sensor assembly. A specific sensor assembly that includes three mutual orthogonal magnetoresistive sensors is the HMC1053 Three Axis Magnetic Sensor available from Honeywell of Plymouth, Minn., USA.

X. Integrated Tracker and Marker

Figure 21:
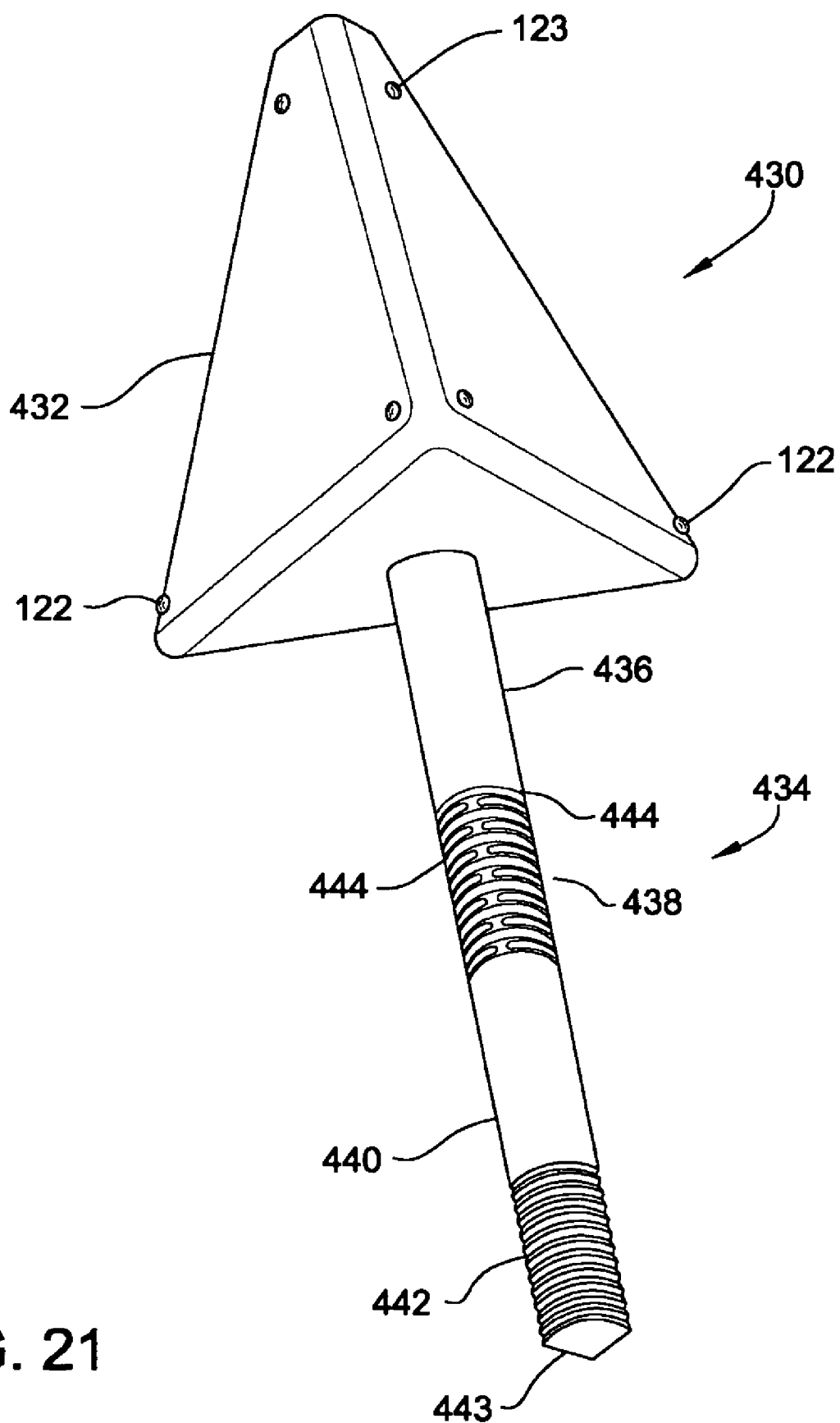
FIG. 21 is a perspective view of an alternative tracker and marker assembly of this invention.

FIG. 21 depicts a tracker and marker unit 430 in which the sensor assembly of FIGS. 15 and 16 may be fitted. It should be recognized that unit 430 may house other EM sensitive transducers. Unit 430 has a pyramidal-shaped head 432. LEDs 122 used for tracking the head 432 are mounted to the outer surface of the head. Additional LEDs 123, that are part of the transceiver unit 130 (FIG. 5) are also mounted to the surface of the head 432.

A stem 434 projects below the flat distal end base of unit 430. Stem 434 includes a leg 436 that is immediately located below and is rigidly attached to the unit head 432. A rigid foot 440 forms the most distal portion of stem 434. Foot 440 is connected to leg 436 by a flexible ankle 438. Threading 442 is disposed around the distal end of the foot 440. Threading 442 allows both the screw securement and screw removal of the foot 440 from the bone to which unit 430 is mounted.

Ankle 438 is shaped to allow foot 440 to bend relative to the leg 436 and also to transmit rotational force, torque, from the leg to the foot. In some versions of the invention, the stem 434 is formed from a single tube-shaped piece of metal. The wall sections of the stem material forming the leg 436 and foot 440 are solid. The wall sections of the stem material forming the ankle are formed with slots 444. The slots 444 provide the ankle 438 with its flexibility relative to the longitudinal axis of the leg 436 while ensuring that the ankle is able to transfer torque to the foot 440. It is believed that the stem 434 can be formed out of a nickel titanium allow such as the alloy marketed as NITINOL.

A flexible sleeve, not illustrated, disposed in the sleeve provides insulation around the active components in the unit. These components include the magnetoresistive sensors 410 and 412, (FIG. 16). In addition, or alternatively, a biocompatible coating is disposed over the flex circuit 416 and sensors 410 and 412. Also in this version of the invention, the transmitter assemblies that emit the EM signals may be disposed in the leg 436 of the unit stem 434. Thus, in most versions of this embodiment of the invention, the EM transmitters are 3.0 cm or less from the complementary receiving units and in, more preferred versions of the invention, this distance is 2.0 cm or less.

Unit 430 is used by screw securing the stem foot 440 into the bone at the position and orientation of which is to be monitored. The pointed distal end tip 443 of the foot 70, as well as the threading 442, facilitates this securement. In this version of the invention, the complementary EM signal transmitters and receiver are very close proximity. Consequently only relatively small strength signals, need to be transmitted between the transmitters and the receivers. In some versions of the invention the cumulative strength of the signals emitted simultaneously by the plural transmitters is 1.0 Watts or less (0.34 Watts or less from each transmitter) and more preferably, cumulatively, less than 0.5 Watts or less (0.17 Watts or less per transmitter.). Further the space in which these signals are transmitted is relatively small, the distance between these components. This means that there is only a relatively small space around unit 430 in which neither ferromagnetic objects nor interfering EM signals should be restricted to ensure the accurate tracking of tissue position and orientation.

In this version of the invention, the overall length of the unit 430 from the distal end foot 440 to the proximal end of head 432 is typically 15 cm or less and in more preferred versions of the invention 12 cm or less. Thus because of its size and the fact that there is no need to maintain the unit head 432 stable relative to the foot 440 means that the presence of unit 430 does not serve as a significant physical obstacle adjacent the surgical site.

Figure 22:
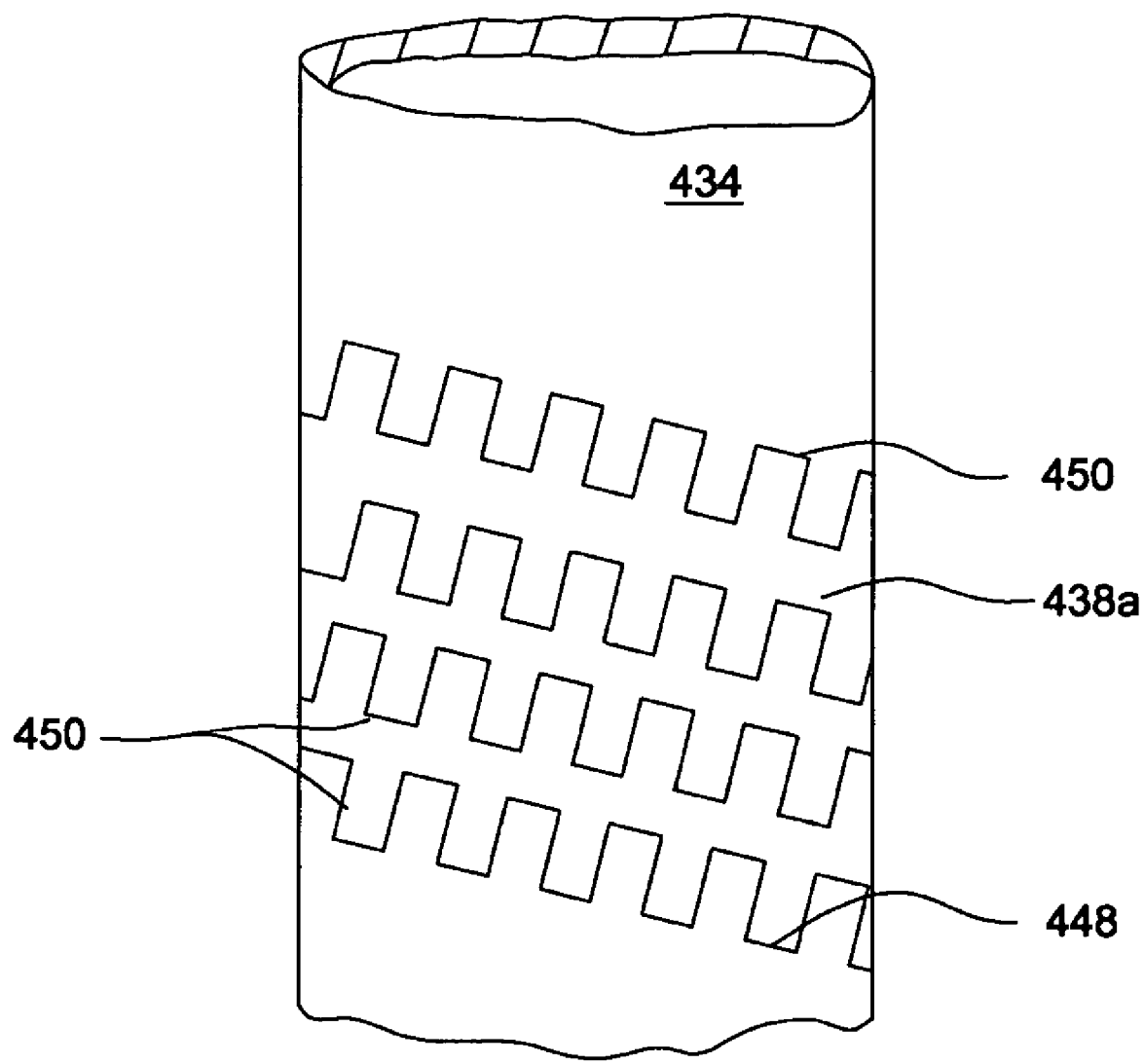
FIG. 22 is a plan view of alternative ankle for the tracker and marker of FIG. 21.

It should be appreciated that the physical features of unitary tracker and marker assembly may vary from what has been described with respect to FIG. 21. FIG. 22, for example, illustrates an alternative flexible ankle 438a of stem 434. Here, ankle 438a is formed in the stem by providing a helical cut 448 around the ankle-forming section of the stem. Cut 448 also is formed to define interlocking castellations 450. The castellations 450 function as the torque transmitting members of the ankle 438a.

XI. Alternative Integrated Tracker and Marker

Figure 23:
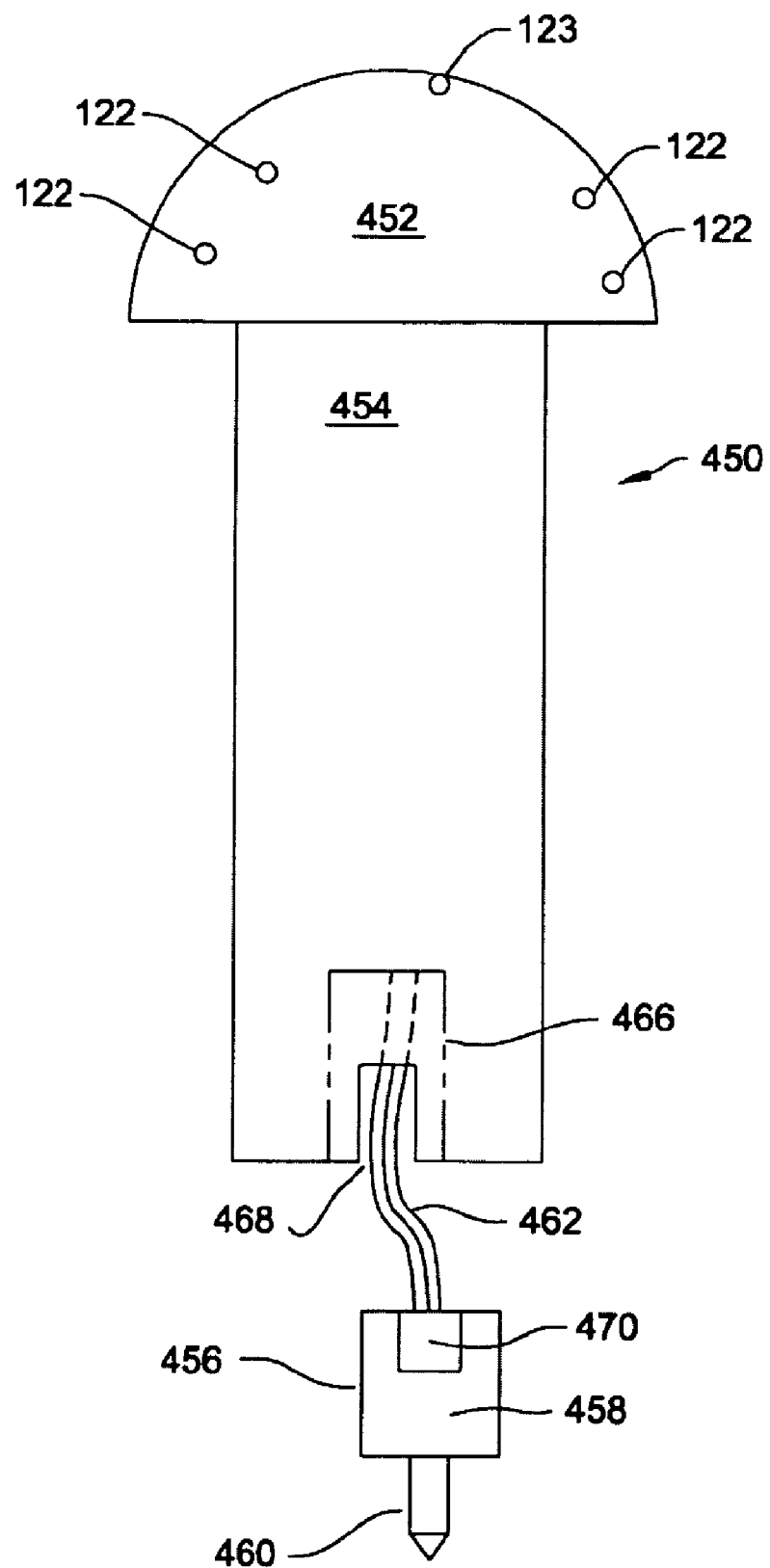
FIG. 23 depicts another alternative tracker and marker assembly of this invention.

An additional alternative tracker and marker unit 450 of this invention is now described by reference to FIG. 23. Unit 450 has a cylindrical head 452. LEDs 122 and 123 used to for, respectively, tracking and data/command signal exchange are mounted to the outer surface of the head 452. An elongate rigid shaft 454 extends downwardly from the base of the head 452.

A marker 456 is located below the distal end of shaft 454. Marker 456 has a head 458 in which the EM sensitive transducer 66 or sensors 410 and 412 are located. A pointed stem 460 is integral with and extends below the marker head 458. Stem 460 is formed with the geometric features needed to releasably secure the marker to the tissue to be tracked. In the illustrated version of the invention, the nail like structure of stem 460 facilitates the driving of the stem into bone.

A cable 462 flexibly connects the marker head 458 to shaft 454. While not illustrated it should be understood that disposed within cable 462 are the conductors used to for signal exchange with the marker transducer assembly. Cable 462 extends from a location inside shaft 454. More particularly, shaft 454 is formed with a distal end bore 466 (shown in phantom) dimensioned to accommodate marker head 458. Internal to shaft 454 and proximal to the base of the bore 466 there is a void space, not illustrated. This void space accommodates the slack portion of cable 462 when the marker head 458 is seated in bore 466.

Shaft 454 is further formed so that at the distal end thereof there are two diametrically opposed slots 468, (one shown). Each slot 468 extends rearwardly from the distal end of the shaft 454 and opens into bore 466. Marker head 458 is formed with two diametrically opposed, outwardly extending ears 470. Marker ears 470 are dimensioned to slip fit into shaft slots 468.

Unit 450 is fitted to the patient by positioning the marker 456 so that the head 458 is in shaft bore 466 and ears 470 are seated in shaft slots 468. Force is then applied through head 452 to drive the marker stem 460 into the bone. Once marker 456 is secured in place, the shaft can be extended away from the marker head 458. The head and shaft subassembly can then move relative to the marker 456. As in the above described versions of the invention, the measurement of EM signals transmitted from the head and shaft to the marker 456 make it possible to continuously monitor the position of the marker relative to the head 452.

When it is time to remove unit 450, the head and shaft are repositioned so that marker head 458 seats in shaft bore 466 and marker ears 470 reseat in slots 468. Torque needed to remove the marker stem 460 from the bone is applied from the shaft 454 to the marker through ears 470. Thus, this version of the invention reduces the effort required after the tracking process to recapture marker so it can be removed. Moreover, unit 450 functions as its own marker insertion and removal tool.

It should be appreciated that in versions of the invention that use magnetoresistive sensors, the output signals of these transducers are affected by their thermal state, temperature shifts. To reduce signal changes caused by these temperature shifts, it is believed best to apply a constant current to them. Moreover, the voltage across each sensor assembly, which is in the form of a Wheatstone bridge, should be monitored. The change in this voltage is a function of the temperature-shift induced changes in the sensitivity of the assembly. Based on the change in the voltage level across an individual sensor assembly, the gain in the output signals from the sensor assembly is adjusted. This gain adjustment compensates for the temperature-induced changes in the sensitivity of the assembly.

XII. Third Alternative Marker

Figure 24:
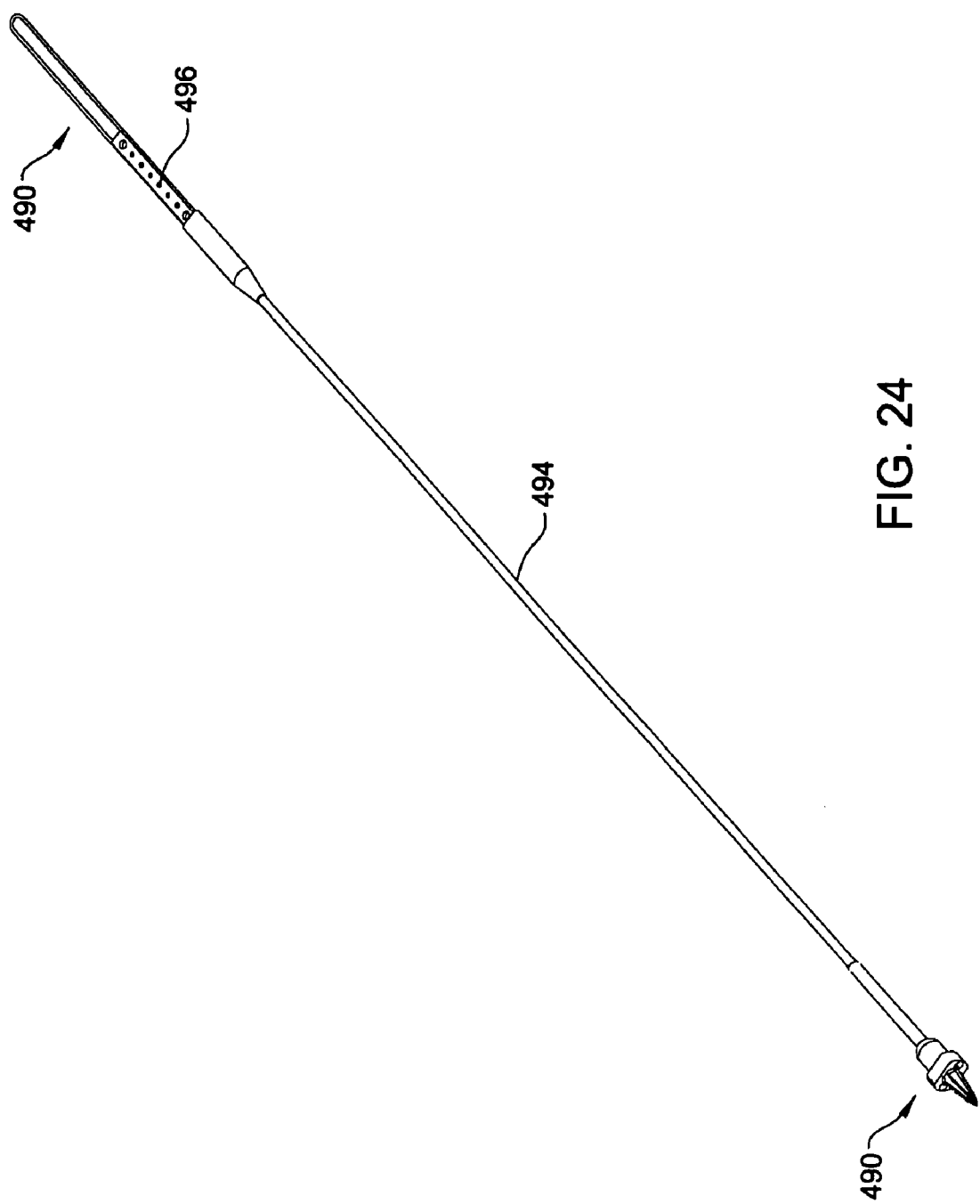
FIG. 24 is a perspective view of a third alternative bone marker of this invention, this marker including a tether.

FIG. 24 illustrates still another alternative marker 490 of this invention. A tether 492 extends proximally from the marker 490. The tether 492 is partially encased in sheath 494 that also extends from the marker 490. Also disposed in and extending proximally outwardly from sheath 494 is a printed circuit board 496. Printed circuit board 496 includes conductive elements that facilitate the connection of the marker sensing elements to a tracker. Printed circuit board 496 also includes memory 498 (FIG. 27) that contains data used for analyzing the signals generated by the marker sensing elements.

Figure 25:
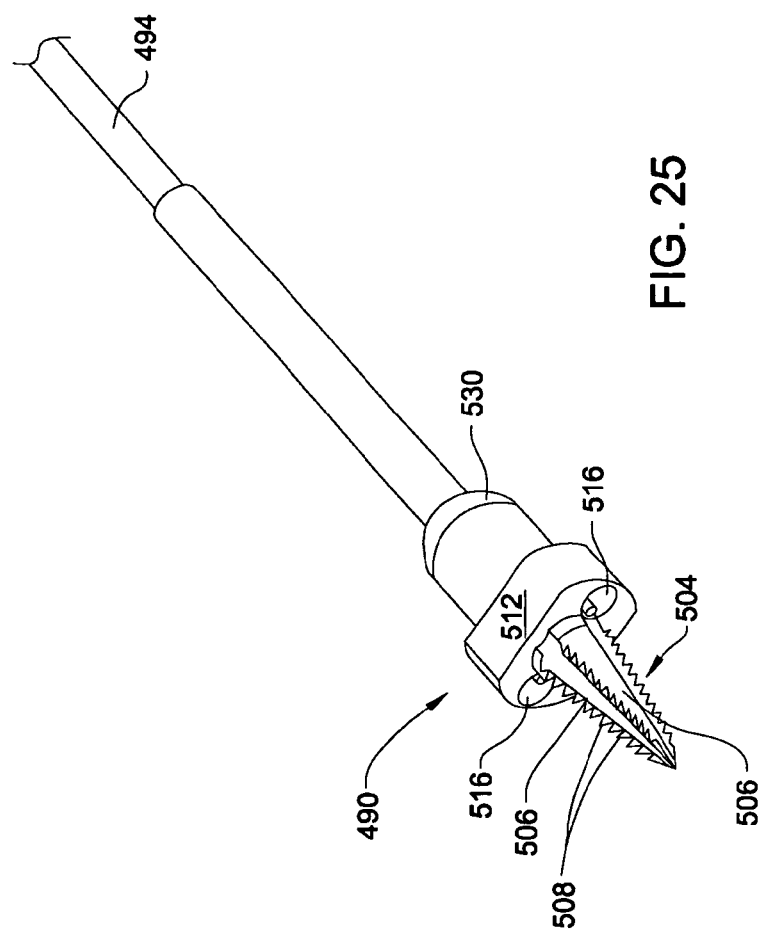
FIG. 25 is perspective view of the third bone marker and the distal end of the sheath connected to the marker.
Figure 26:
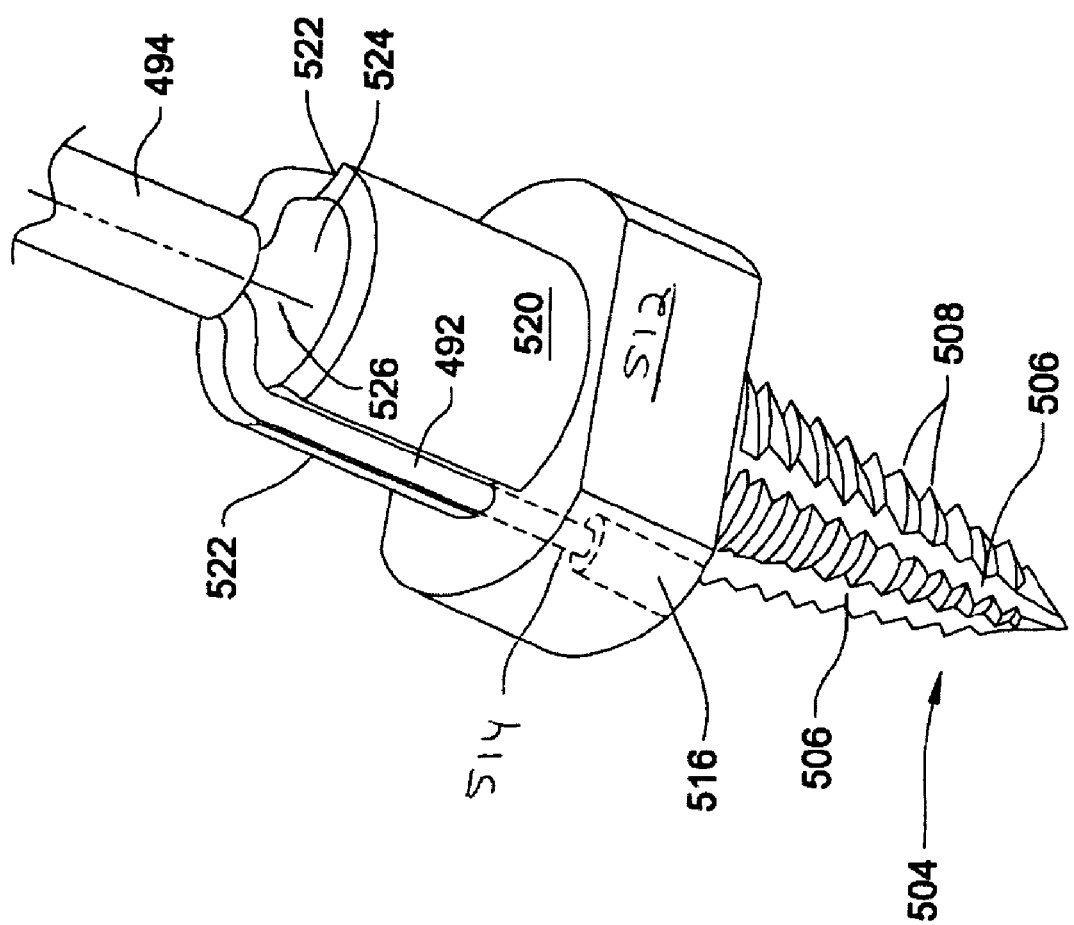
FIG. 26 is a perspective view of the third bone marker, with the boot removed.

Marker 490, now described in detail by reference to FIGS. 25 and 26, is formed from a single piece of non-ferromagnetic biocompatible material. In one version of the invention, the marker 490 is formed from stainless steel. The most distal section of the mark is a spike 504 that functions as the bone interface. In the illustrated version of the invention, spike 504 generally has a conic shape such that the most distal end of the spike, the distal end of the marker, terminates at a point. Spike 504 is formed to have a set of concave, arcuately spaced apart recesses 506 (two shown) that extend inwardly from the outer perimeter of the spike. In some versions of the invention, the marker 490 is formed to have two diametrically opposed recesses 506. In other versions of the invention there are three recesses 506 spaced 120° apart. Bone markers 490 of this invention with four or more recesses are also possible. It should further be understood that the spike is formed so that recesses 506 are centered along longitudinal axes that are angularly offset from the longitudinal axis of the marker. Thus the recesses 506 taper outwardly away from the distal end point of the spike 504.

The marker spike 504 is also formed with a set of barbs 508. Barbs 508 project outwardly from the outer perimeter surfaces of the spike 504 between the recesses.

Above the spike 504, marker 490 is formed to have neck 512. The neck 512 has an oval shape. The opposed flat outer surfaces of the neck 512 (surfaces not identified) are dimensioned to receive a wrench like tool (not illustrated). When in the course of the procedure it is necessary to remove the marker, the tool is used to rotate the marker. This movement separates the bone holding marker, the bone lodged in the spike recesses 506.

The marker neck 512 is formed with two bores 514 (one shown in phantom, FIG. 26). The bores 514, which open from the proximally facing top surface of the neck 512, are located on the axis that extends between the opposed curved ends of the neck. Each bore 514 opens into a wide diameter counterbore 516 (one shown in phantom in FIG. 26) that is concentric with the bore 514. Each counterbore 516 opens into the distally directed bottom surface of the neck 512. It should be appreciated be appreciated that bore-counterbore pairs 514 and 516 are further positioned so that the counterbores 516 open into the surface of the neck, not the spike 504.

Above the neck 512, marker 490 is formed to have a head 520. Marker head 520 has a generally cylindrically outer profile. The head 520 is centered along the longitudinal axis of the spike 504. The head 520 is further formed so as to have within the outer surface two diametrically opposed concave channels 522. Each channel 522 is aligned with and opens into a separate one of the neck bores 514.

The marker head 520 is formed with a closed end bore 524. Bore 524 opens into the head 520 from the proximally face top of the head. Bore 524 is the void space internal to the marker wherein the EM sensitive transducers or EM energy emitters of the system of this invention are housed.

Extending proximally outwardly from the marker head bore 524 are the insulated conductors 526 (one shown) over which signals are exchanged with the EM transducers (emitters). While only one conductor 526 is shown for simplicity, often there will be six conductors 526; two for each EM transducer (emitter).

The conductors 526 are contained in sheath 494. The sheath 494 extends to but not over the marker head 520. A flexible boot 530 disposed over the distal end of the sheath 494 and the marker head 520 holds the sheath to the marker 490. Boot 530 is formed of heat shrink material, that when shrunk, seals tightly against both the sheath 494 and the marker head 520.

Figure 27:
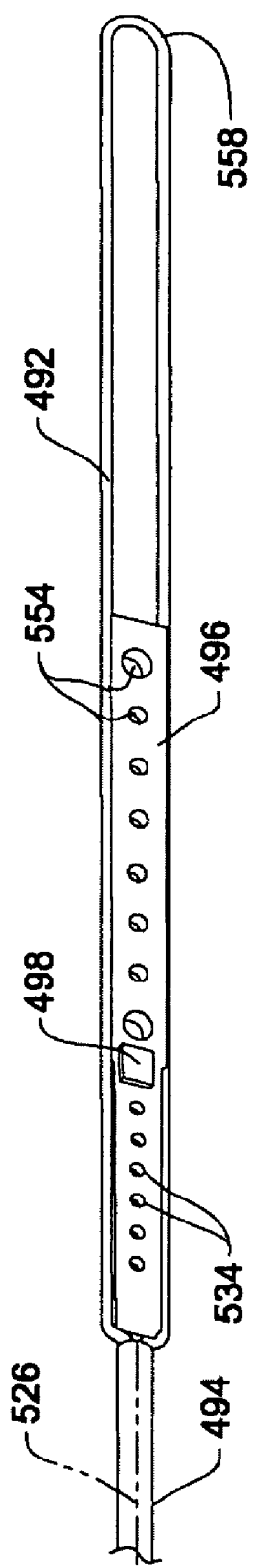
FIG. 27 is a perspective view of the printed circuit board and tether attached to the third bone marker, wherein the protective glove is removed to show the whole of the printed circuit board.
Figure 29:
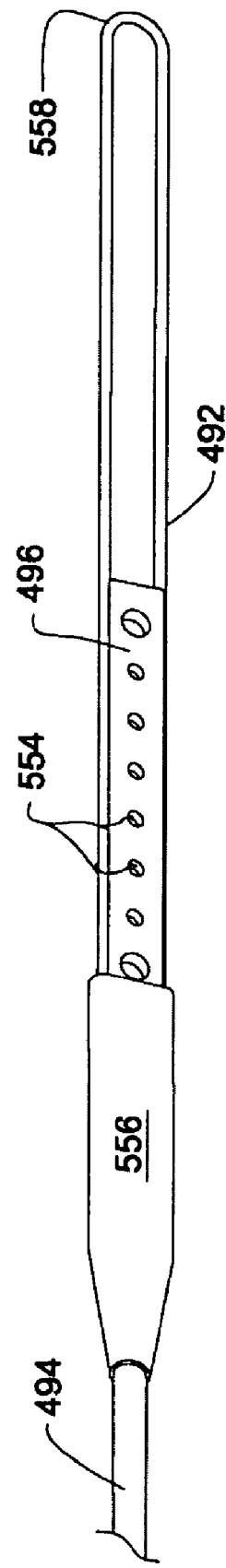
FIG. 29 is a perspective view illustrating how the protective glove is disposed over the proximal end of the sheath and the adjacent portion of the printed circuit board associated with the third bone marker.

The conductors 526 extend to printed circuit board 496, now initially described by reference to FIG. 27. The printed circuit board 496 is an elongated structure. Bond pads 534, shown as holes, are provided on the distal end of the printed circuit board 526. The bond pads 534 are the circuit board components to which conductors 526 are attached. Also mounted to the printed circuit board 496 is memory 498. In one version of the invention, printed circuit board 496 is formed with a small recess located proximally forward of the bonding pads to which conductors 526 are attached (recess not illustrated). The memory 498 is seated and secured in this recess. In some versions of the invention memory 498 is a read only NOVRAM. In other versions of the invention, memory 498 is a EEPROM to which, post manufacture of the marker it is possible to write data to and read data from multiple times. In one version of the invention data are read from (and potentially written to) memory 534 over a one-wire communications link. One EEPROM that can function as memory 498 is the DS2431 1024-Bit, 1-Wire EEPROM available from Maxim-Dallas Semiconductor of Dallas, Tex., USA.

FIG. 28 is a block diagram illustrating the contents of memory 498. A marker identification field 540 contains data used to identify the characteristics of marker 490. These data include data describing the physical characteristics of the marker. The data in field 540 may also indicate the type of tracker with which the marker can be used. A marker authorization field 542 includes data used to determine if the marker can be used with the system 30. Thus field 542 may contain a proprietary authorization code or key. An appropriate code or key must be present in order for the other components in the stem to forward signals to or receive signals from the marker.

In versions of the invention wherein, during a procedure, data can be written to memory 534, the memory also contains a use history field 544. Use history field 544 contains data indicating whether or not the marker has been previously used. In some versions of the system of this invention, it is anticipated that marker 490 is a single use component. In these versions of the invention, field 544 is single bit field. The bit in this field is a flag bit that is set depending on whether or not the marker was previously used. If, upon initialization of the system and the reading of the contents of the use history field 544, it is determined the marker 490 was not previously used, the system allows the marker to be used. The system also resets the bit of field 544 to indicate that the marker was used.

If upon the reading of the bit forming the use history field 544 the system determines that the marker was previously used, the system, at a minimum provides the surgical personnel with notification of this fact. In some versions of this invention, the system also prohibits use of the previously used marker.

Marker memory 498 also contains three fields 546, 548 and 550 in which transducer efficiency coefficients are stored. Towards the end of the process of manufacturing the marker, the sensitivity of the three coils or other transducers (or EM emitters) integral with the marker are measured. Generally, each transducer has an efficiency with which it generates signals as a function of received EM energy. Similarly, each EM emitter, based on the input energy signal, has an efficiency with which it emits EM energy. Often these efficiency values vary with frequency. The efficiency coefficients are for the specific axis along which the transducer is sensitive to EM energy (the axis along which the EM emitter emits energy). Thus, for each transducer, the associated field 546, 548 or 550 contains data that describes efficiency. These data may define different efficiency over the range of frequencies of signals the transducer may potentially monitor. If the marker includes a set of EM emitters, the efficiency data describes the strengths of the output signals over the range of frequencies over which the signals could potentially be emitted.

When the marker 490 is attached to the associated tracker, the data in memory 498 are forwarded to processor 44. Processor 44, adjusts the measurements of EM strength made by the marker transducers based on the efficiency data. These adjusted measurement of signal strength are then what is used in step 188 (FIG. 7C) to determine marker position and orientation.

Printed circuit board 496 also includes a set of terminals 554. In the illustrated version of the invention there are eight terminals 554; six terminals for the transducer (emitter) conductors 526 and two terminals for the one-wire connection to memory 534. Each terminal 554 of illustrated printed circuit board 496 consists of a hole formed in the proximal section of the board forward of memory 534 and plating around the hole. (hole not identified; plating not illustrated.) Terminals 554 are linearly aligned. The most proximal and distal of the two terminals 554 have holes that are larger in diameter than those of the six intermediate terminals.

The printed circuit board 496 is located immediately forward of the proximal end of sheath 494. A flexible glove 556 holds the printed circuit board 496 to sheath 494. Glove 556 extends over the proximal end of the sheath and over the distal end of the printed circuit board 496. More particularly, the glove 556 extends over bond pads 534 and memory 498. The glove does not extend over terminals 554. In one version of the invention, the glove 556 is formed from the heat shrink material similar or identical to the material from which boot 530 is formed.

The tether 492 is a line able to transmit 10 to 50 pounds or more of force. In one version of the invention, tether is formed from an aramid (nylon) type fiber sold under the trademark KEVLAR by the DuPont Company. The tether 492 is open end line. The opposed ends of tether are seated in separate ones of the marker counterbores 516. A knot (not illustrated) in the end of the tether 492 holds the tether in the counterbore 516. Alternatively, a ball welded or otherwise secured to the end of the tether 492 holds the tether in the counterbore 516. From the marker counterbore 516, each end of the tether 492 extends through the associated hole 514 formed in the marker neck 512. Upon exiting the hole 514, the tether is seated in the adjacent channel 522 formed in the marker head 520. From the marker 490, the ends of the tether 492, like the conductors 526 extend through boot 530 and sheath 494.

The opposed ends of the tether 492 extend out of the proximal end of glove 556. The ends of the tether come together at a loop 558 located proximally forward of the printed circuit board 496. In one version of the invention forward of the loop 558, towards the marker 490, the opposed sides of the tether are tied to the printed circuit board. In one version of the invention, the opposed sides of the tether forward of loop 558 are secured to the sides of the printed circuit board 496.

Distal from the printed circuit board, the conductors 526 have some slack relative to the adjacent sections of the tether 496. This slack minimizes the extent to which the force the tether places on the marker stress the conductors 526 and their connections to the transducers (EM emitters) and the printed circuit board.

Figure 30:
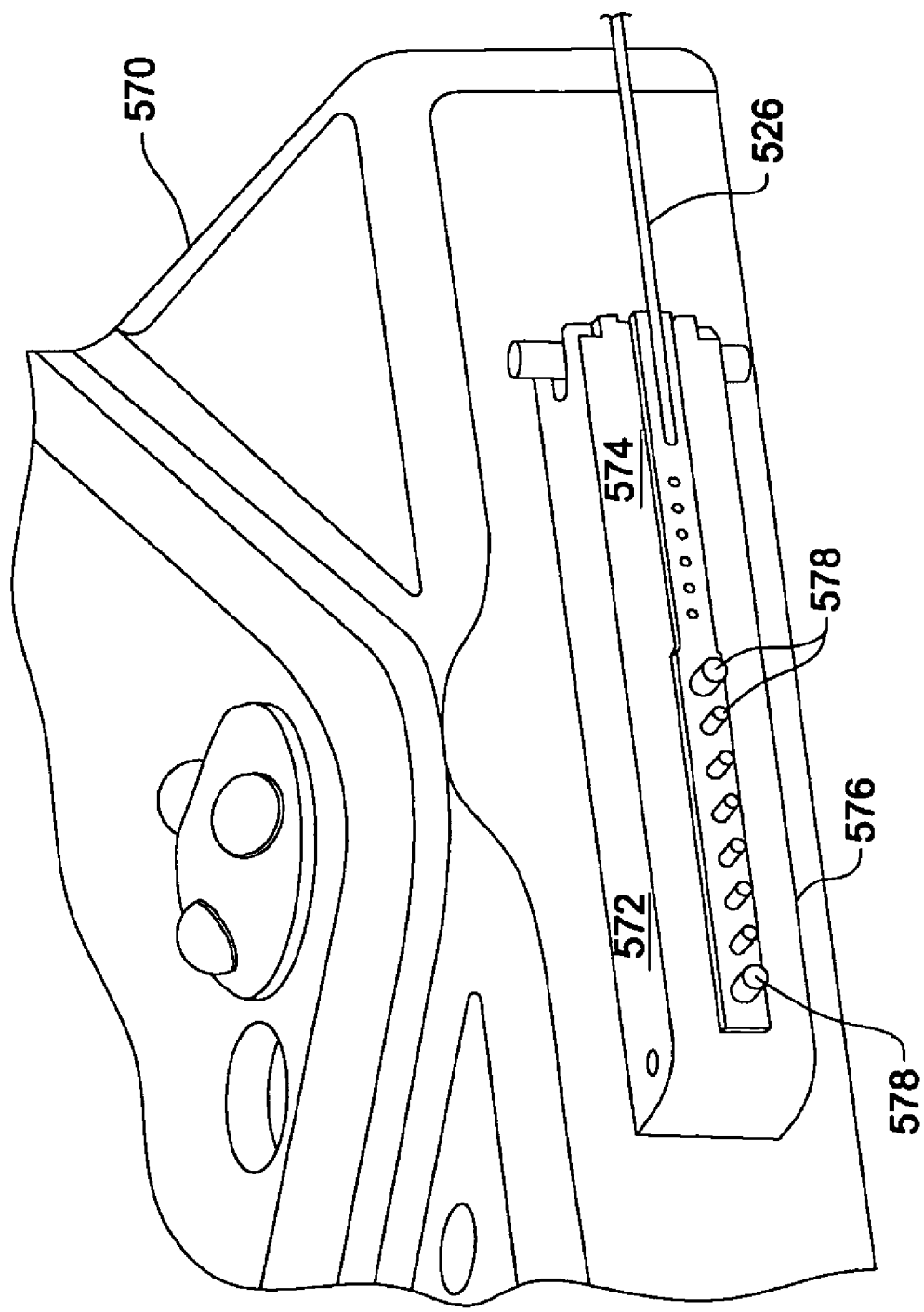
FIG. 30 illustrates how the third bone marker is attached to a complementary tracker.

FIG. 30 illustrates a portion of a tracker 570 with a bar 572 to which marker 490 is releasably attached. Bar 572 is mounted to an outer side wall of the tracker housing. Bar 572 has an outer surface 574 with an elongated recess 576. Recess 576 is shaped to closely received the proximal end of sheath 494 and the end of the printed circuit board 496 that extends beyond the sheath.

Bar 572 is further formed with a set of linearly aligned spaced apart conductive posts 578. Posts 578 extend upwardly from the base of recess 576. Marker 490 is mounted to tracker 570 by seating sheath 494 and printed circuit board 496 so conductive posts 578 extend through the circuit board terminal holes. Upon this positioning of the tether and printed circuit board 496, the posts 578 contact the conductive elements of the terminals 574.

Figure 31:
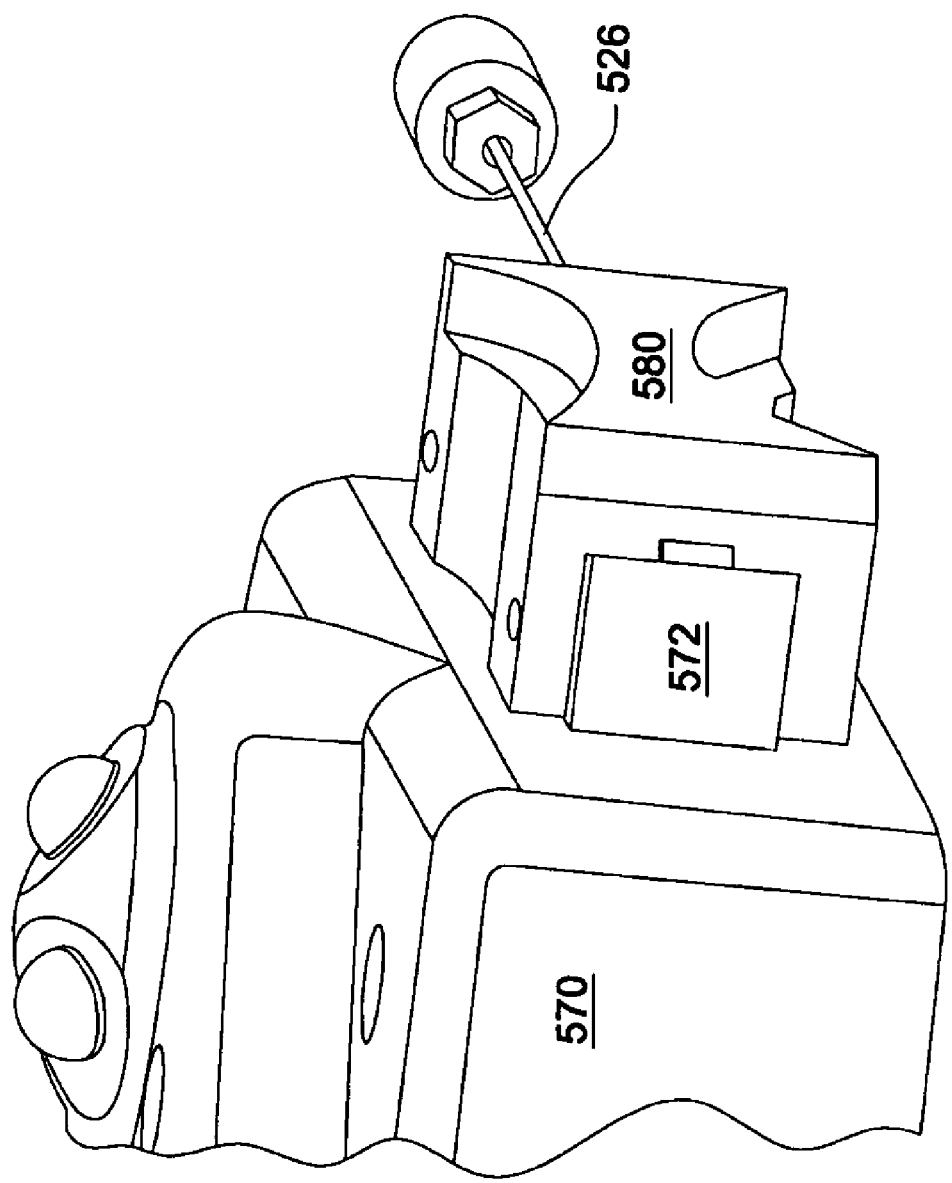
FIG. 31 illustrates the removably cap that holds the third bone marker to the associated tracker.

A cap 580, seen in FIG. 31, snaps fits over bar 572. The cap 580 holds the printed circuit board 496 to the bar 572 to, by extension, hold the marker 490 to the tracker 570. It should be understood that since the tracker 570 is loosely positioned on the body of the patient, there should be minimal mechanical strain on the conductors 526 and their connections to the transducers (emitters) and printed circuit board bond pads. Also, while not illustrated, it should likewise be appreciated that tether loop 558 extends out of the gap between the tracker bar 572 and cap 580.

Marker 490 of this version of the invention is secured into a section of the bone by pressing the spike 504 into the bone. The barbs 508 extend into the bone so as to hold the spike 504 in place. Also, the bone seats in the spike recesses 506 to inhibit rotation of the marker 490. Once the marker 490 is so secured a tension can be placed on it by pulling on the tether 494. More specifically, by applying a force on the tether 494, the force, a pull force, is transmitted through the tether and applied to the marker. A strain gauge can be used to ensure that a specific minimal amount of force is applied to the marker 490. If the marked 490 remains fixed when this force is applied, the surgical personnel know that the marker is firmly attached to the bone.

As described above, when it is time to remove the marker 490, a tool is used to rotate the marker so as to break the bone disposed in the recesses 506 and that is pressed against the barbs 508. Once the marker 490 is so rotated, pulling on the tether 494 pulls the marker out of the bone and away from the patient.

Thus, the above construction of the marker of this invention provides an easy means to both ensure the marker is firmly secured to the bone and, when it is time to extract the marker, to remove the marker. Moreover, the tether 492 pivots relative to the bone marker 490. Thus, when the tether 492 is pulled on, should the force include a torque component, this fraction of the force is not transferred to the bone marker 490. Thus if the tether is so rotated during the process of verifying that the marker is firmly attached, the rotational force is not be transferred to the marker wherein it could possible cause the marker to rotate free of the bone.

Still another feature of marker 490 of this versions of the invention is that the memory 498 contains data describing the efficiencies of the transducers (or emitters) integral with the marker. Processor 44 uses these data to correct the output signals generated during the navigation process in which these components in order provide improved accuracy regarding the position and orientation of the marker 490. The data in memory 498 are also useful for determining whether or not marker 490 can be used and can be used with the tracker to which the marker is attached.

Still another feature of marker 490 is that circuit board 496 and complementary tracker bar 572 provide an easy means for releasably connecting the marker to and disengaging the marker from tracker 570.

XIII. Third Alternative Tracker

Figure 32:
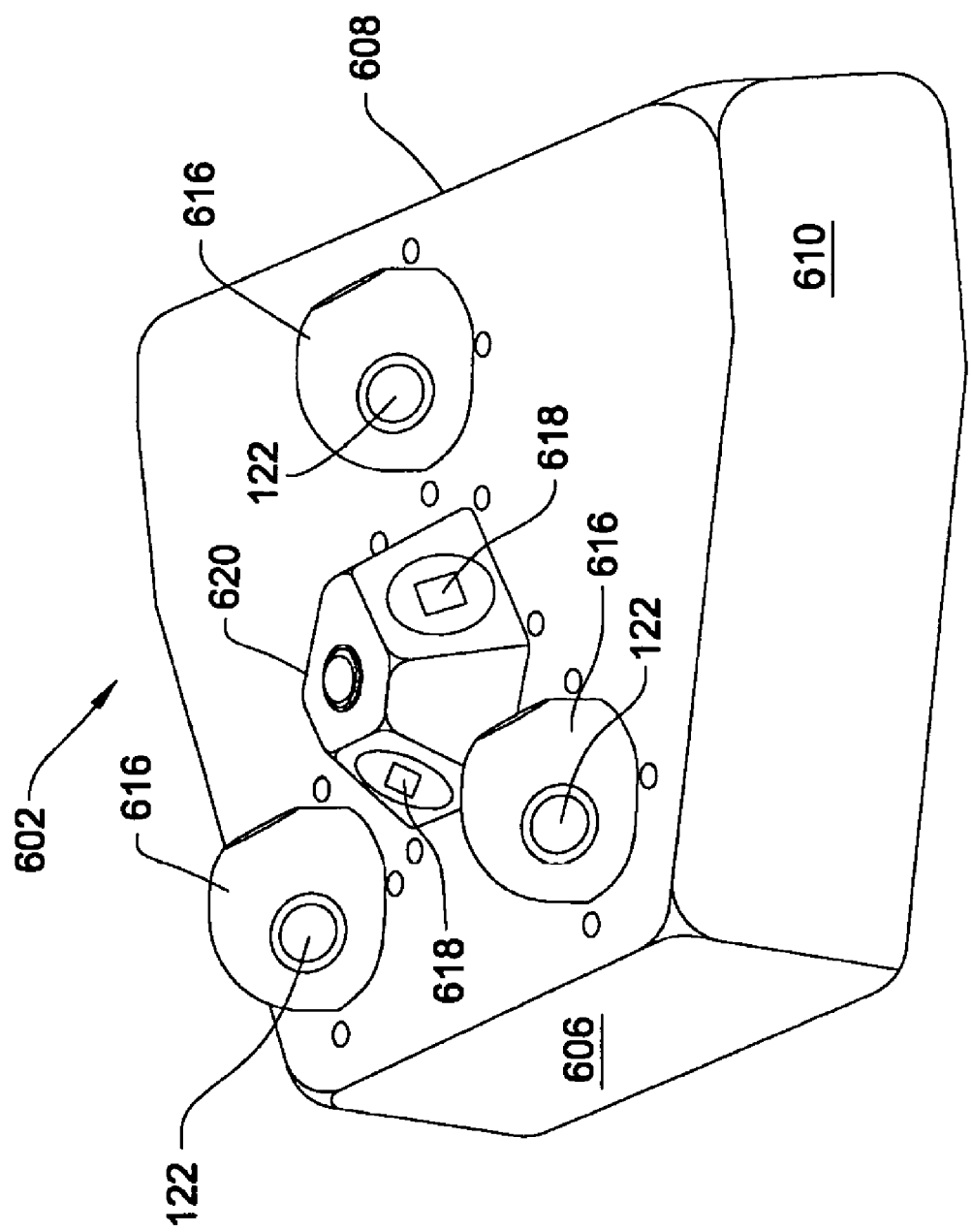
FIG. 32 is a perspective view of another alternative tracker of this invention.
Figure 33:
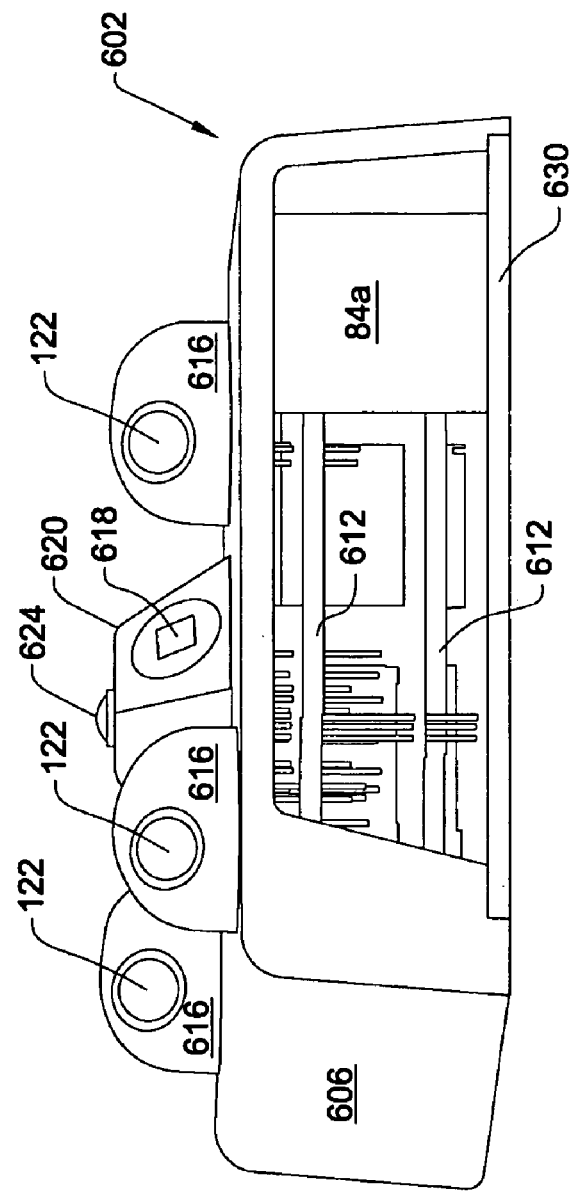
FIG. 33 is a perspective view of the tracker of FIG. 32 wherein a portion of the shell is partially removed so the interior of the tracker can be viewed.
Figure 34:
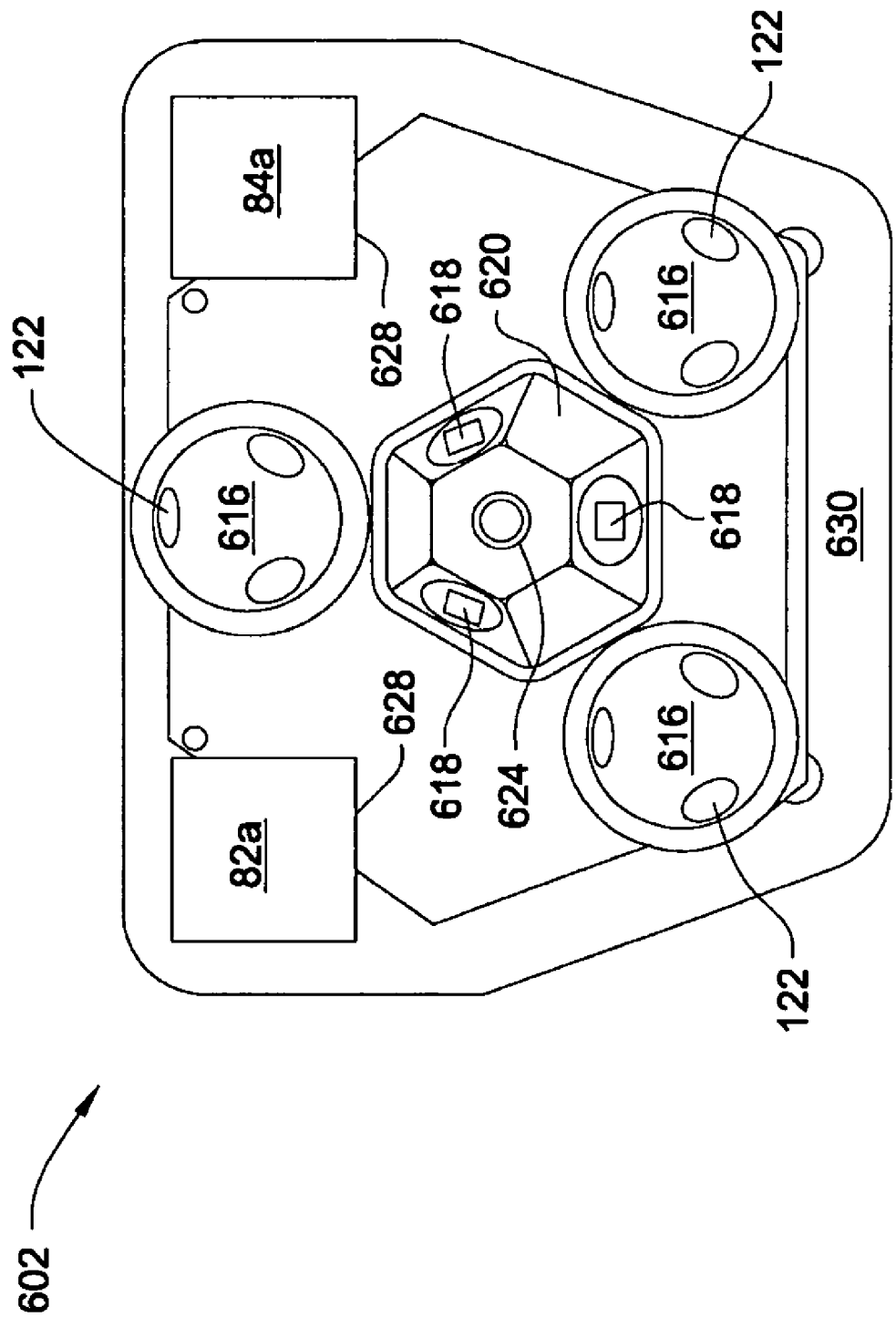
FIG. 34 is a top view of the tracker of FIG. 32 wherein the shell is removed.

FIGS. 32-34 illustrate another alternative tracker 602 of this invention. Tracker 602 has an outer shell 604 with opposed front and rear faces 606 and 608, respectively. In the illustrated version of the invention, the profile of the tracker 600 is such that front face 606 is shorter than rear face 608. Opposed outer shell side faces 610 (one shown) extend between the front and rear faces 606 and 608, respectively. Outer shell 604 is further formed so that each side face 610 extends perpendicularly away from the adjacent edge of the rear face 608. Each side face 610 then angles inwardly toward the front face 606.

Disposed inside shell 604 are two parallel, horizontally aligned printed circuit boards 612 and 614. The upper of the two circuit boards, circuit board 612, supports the components used to, with the second navigation system, track the position and orientation of the tracker 602. In the illustrated version of the invention, these components include the LEDs 122, the outputs of which are monitored by localizer 40. In the illustrated version of the invention, three LEDs 122 are mounted to a set of three heads 616. Heads 616 are arranged in an equiangular triangle and are mounted to the top of the upper circuit board 612.

Also mounted to the upper circuit board are the components that facilitate signal exchange between tracker 602 and the external processor 44. Specifically, tracker has a set of IR sensitive photocells 618. There are three photocells 618 mounted in a head 620. The photocells 618 are equangularly spaced apart from each other. Head 620 is centered in the center of the triangle defined by heads 616.

Disposed on the top of the head 620 is an IR emitting LED 624. LED 624, like photocells 618 is part of the processor 44 to tracker 62 communication system. The photocells 618 receive the data/instruction type IR signals emitted by transceiver 132. LED 624 transmits data to the transceiver 132.

Not identified are the openings in shell 606 through which heads 616 and head 620 extend.

The lower of the two circuit boards, circuit board 614, supports the components used to exchange signals with the complementary transducers (or EM emitters) in the bone marker 490.

The opposed rear end corners both circuit boards 612 and 614 are formed to define rectangular cut-outs. (Only the cut-outs 628 defined by the upper circuit board 612 are identified.) Disposed within each pair of aligned cutouts is a transmitter assembly 82a and 84a. Here it is seen that each transmitter assembly 82a and 84a is in the form of square core. Wires are wound around the sides and top of the core to form the individual transmitting antenna, 86a-90a and 86b-90b.

A plate 630 formed of non-conductive material is fitted to the bottom of shell 614 below lower circuit board 614. Plate 630 forms the bottom base of the tracker 602. The plate 630 is also the component of the tracker that supports the transmitter assemblies 82 and 84a. Standoffs, two partially seen but not identified in FIG. 34, extend upwardly from plate 630. These standoffs hold circuit board 614 above the plate 630 and circuit board 612 above circuit board 614.

Tracker 602 of this embodiment of the invention is constructed so that both transmitter assemblies 82a and 84a are located adjacent the rear end of the tracker shell 604. A benefit of this construction is that the front end of the tracker can be positioned relatively close to a ferromagnetic object, such as cutting guide 135 (FIG. 6) without the object adversely effecting the emission of the EM signals by the tracker.

Figure 35A:
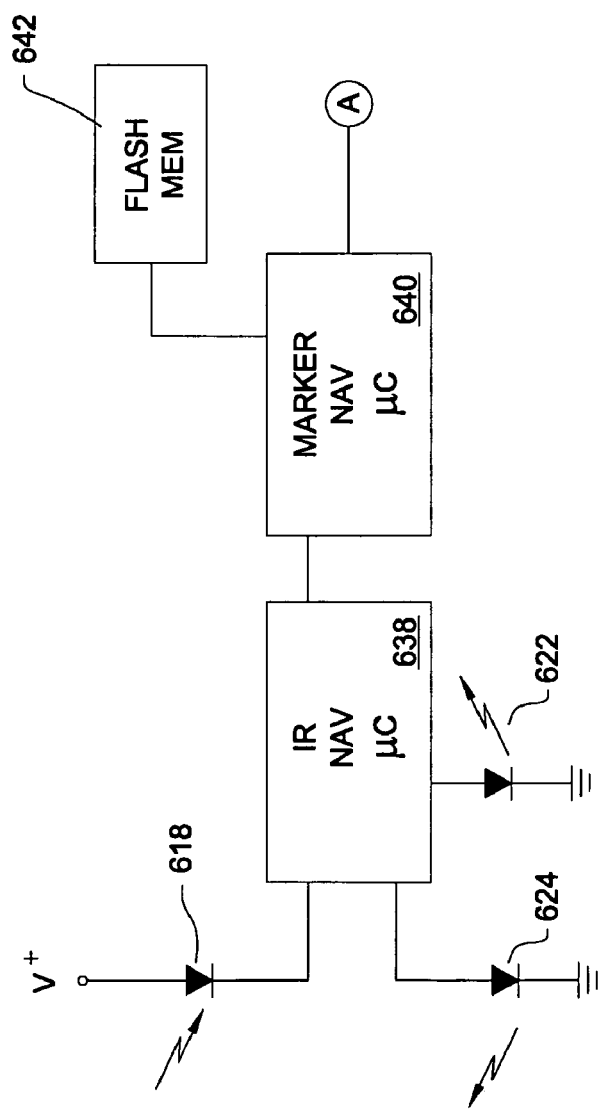
FIGS. 35A and 35B collectively form a block diagram of the electrical components internal to the tracker of FIG. 32.
Figure 35B:
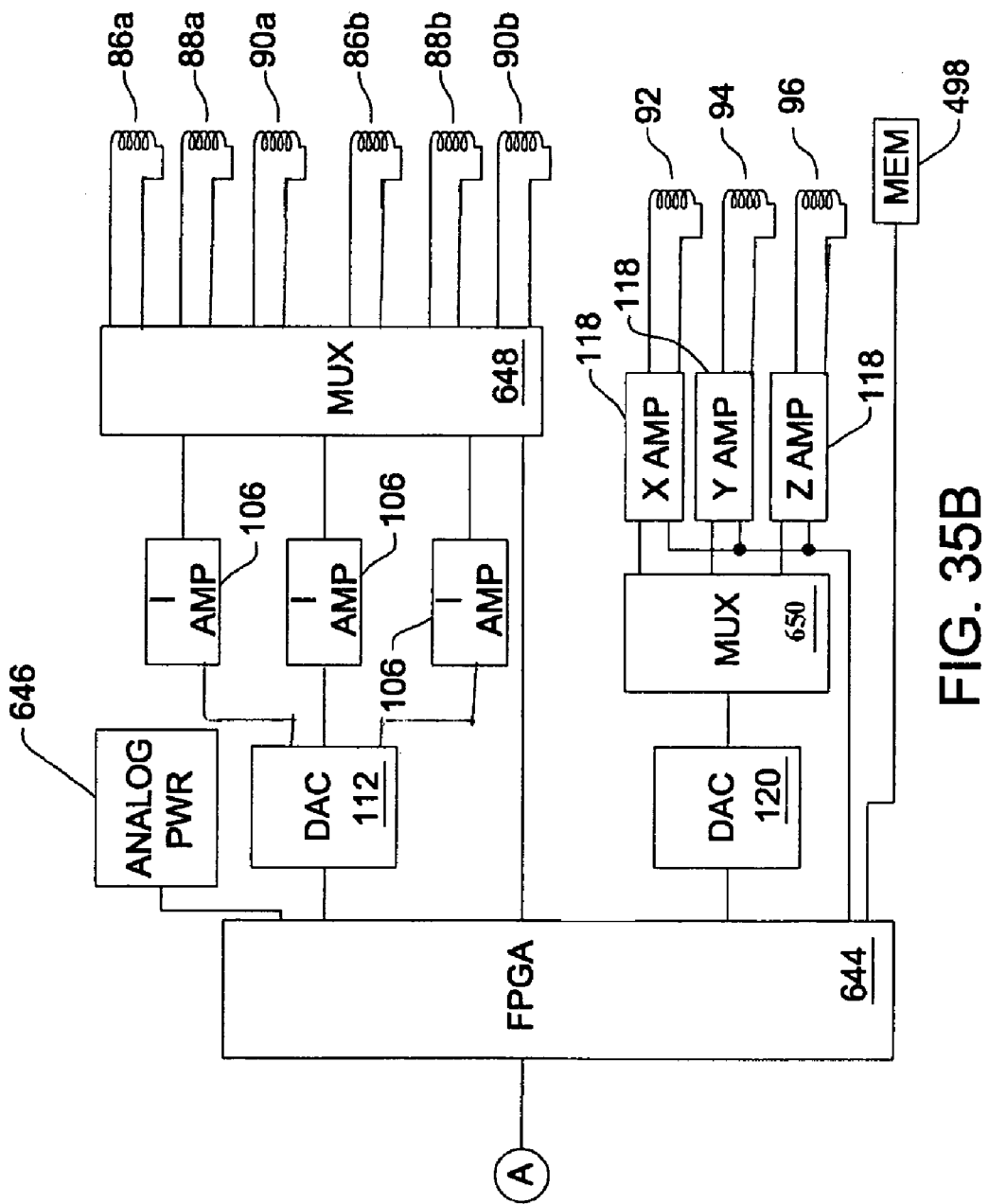

FIGS. 35A and 35B illustrate the basic components of the circuit internal to marker 490 and tracker 602. These components include the LEDs 122 that emit the light monitored by the localizer 40 and the photocells 618 that monitor the IR signals emitted by transceiver 132. For purposes of simplicity only a single one of the LEDs 122 and a single photocell 618 are illustrated. Still another one of these components is the LED 624 that emits the IR data signals monitored by transceiver 132. Also not shown are the circuits that generate the drive current applied to LEDs 122 and 624 and the circuits that amplify the signals emitted by photocells 618.

The actuation of LEDs 122 and 624 and the basic processing of the data signals received by the photocells 618 is performed by an IR navigation microcontroller 638. Microcontroller 638 can be constructed from the P89LPC932A1, an 8051-based microcontroller available from (Philips) Keil Elektronik GmbH in Grasbrunn, Germany. One function of microcontroller 638 is controlling the actuation of the LEDs 122 so the IR navigation system can track the position and orientation of tracker 602. A second function of microcontroller 638 is to facilitate the exchange of signals between system processor 44 and the navigation system formed by the bone marker 498 and the tracker 602.

A second microcontroller, the marker navigation microcontroller 640 is also contained in tracker 602. Microcontroller 640 receives the instruction data extracted by microcontroller 638 for the marker-tracker navigation system. Microcontroller 640 also formats the data generated by the marker-tracker navigation system into a form in which it can be processed by microcontroller 638 and forwards the data to microcontroller 638. Microcontroller 638 then selectively actuates LED 624 so as to cause the LED 624 to broadcast these data. The type of microcontroller employed as microcontroller 638 can also be employed as the marker navigation microcontroller 640

Marker navigation controller 640 performs its functions based on instructions contained in a flash memory 642.

The marker navigation microcontroller 640 also initializes an FPGA 644, also part of the marker-tracker navigation system. In one version of the invention the XCS400 FPGA available from Xilinx is used is employed as the FPGA 644. The FPGA 644 regulates the instantaneous operation of the marker-tracker navigation system. One function of the FPGA is to generate the instructions that cause the transmitter assemblies 82a and 84a to emit the appropriate EM signals. Thus, the FPGA generates to the DAC 112 digital instructions that cause the individual antenna 86a-90a and 86b-90b to emit EM signals of the appropriate magnitude and frequency. The DAC 112 output analog versions of these signals to the voltage controlled current sources 106. In the version of the invention illustrated in FIG. 35B there are three current sources 106, one for each axis along which the EM signals are to be transmitted. The output signals from the current sources 106 are applied to a multiplexer 648. Multiplexer 648 applies the signals from the current sources to either the antennae 86a-90a forming transmitter assembly 82a or the antennae 86b-90b forming transmitting assembly 84a. Which transmitter assembly 82a or 84a the current signals are applied is based on a control signal asserted by the FPGA 644 that is applied to the multiplexer 648.

The FPGA 644 also receives the digitized signals representative of the strength of the EM waves monitored by the transducers internal to the marker 490. In FIG. 35B, these transducers are illustrated as coils 92, 94 and 96. Each marker coil 92, 94, 96 is connected to a separate variable gain amplifier 118 internal to the tracker 602. The output signals from the amplifiers 118 are applied to a 3:1 multiplexer 650. The amplified transducer signal switched on by the multiplexer 650 is digitized by analog to digital converter 120. The digitized representations of the amplified transducers signals are applied from the converter 120 to the FPGA 644.

The FPGA 644 is the component of the marker-tracker navigation system that performs a fast Fourier transformation (FFT) of the digitized transducer signals. The FPGA forwards the data produced as a result of these analyses to the marker navigation microcontroller 640. The marker navigation microcontroller 640 then forwards these data to the IR navigation microcontroller 638 so that the microcontroller 638 can over LED 624 broadcast these data to the system processor 44.

FPGA 644 further functions as the interface to the memory 498 integral with the marker 492. Data read from the memory 498 are read through the FPGA 644. Data written to the memory 498 are forward to the memory from the FPGA 644.

The FPGA 644 also controls an analog power supply 646 also part of the marker-tracker navigation system and internal to the tracker 602. While the connections are not shown, analog power supply 646 is understood to provide the energization signals to the current sources 106 and the current amplifiers 106, DAC 112, amplifiers 118, ADC 120, and the multiplexers 638 and 650. The FPGA 644 only activates the analog power supply 646 when one of the components energized by the power supply is to be actuated. This serves to reduce the overall amount of charge drawn from the battery 134 (FIG. 5) internal to the tracker 602.

In comparison to a processor such as a DSP, FPGA 644 uses less power to regulate the operation of the transmitter assemblies 82a and 84a and perform FFT transformations of the signals received from the marker transducer assembly. Thus, this construction of the tracker is designed to further reduce the overall amount of power that needs to be drawn from the battery 134 in order to operate the tracker of this invention.

XIV. Alternative Embodiments

While in some versions of the invention, EM waves are the medium through which energy is transmitted through the body it should be appreciated that this exemplary, not limiting. In other versions of the invention, the energy exchange may be by RF waves. Still in other versions of the invention sonic or ultrasonic energy may be transmitted between the subcutaneous tissue marker and the above skin level tracker.

It should also be understood that the second navigation system, the system used to determine the position and orientation of the tracker 32 relative to the localizer 40, may rely on transmission of other forms of energy than IR energy to determine the position and orientation of the tracker. These alternative forms of energy include but are not limited to, sonic, ultrasonic, visible light, ultraviolet light, EM and RF energy.

Further there is no requirement that in all versions of the inventions a wired connection exist between the tracker and the marker. In some versions of the invention, the marker may have its own battery or receive power inductively from the tracker. In these versions of the invention, the signals generated by the sensors internal to the marker are transmitted at RF wavelengths to a complementary receiver in the tracker.

Likewise, in some versions of the invention, the tissue marker contains the components that emit energy. In these versions of the invention, the tracker contains the sensors that monitor the strength of the emitted energy.

Also, both the frequency hopping processes of this invention and the integration of the EM producing devices to the EM navigation system are not limited to implementation in the disclosed hybrid navigation system. These features of the invention of this application can be integrated into a conventional unitary navigation system that relies on the measurement of EM signals to determine the position and orientation of a tracker. Again, the Applicant's incorporated by reference U.S. patent application Ser. No. 11/123,985 describe constructions of EM navigation system to which the above features of this invention can be integrated.

It should be appreciated that in these navigation systems, the components in the tracker 32 and localizer 40 may be reversed. Thus, in some of these navigation systems, the tracker contains the EM signal emitting assemblies and the localizer contains the sensors used to measure the strength of the EM signals. In alternative versions of these systems, the localizer contains the EM signal emitting assemblies; the tracker contains the EM sensors.

Further in alternative surgical navigation systems such as systems wherein the strength of RF, photonic or ultrasonic signals are monitored, the frequency shifting process of this invention can be employed to reduce the instances wherein ambient releases of energy adversely affect can adversely affect the determination of either tracker position and orientation and/or marker position and orientation. Thus, it should be understood that the frequency detecting and frequency shifting processes of this invention are not limited to implementation in navigation systems that monitor EM energy emissions.

In some versions of the invention, the conductors over which tracker either outputs signals to or receives signals from the components in the bone marker function as the tether through which a pull force is applied to the marker.

Therefore, it is an object of the appended claims to cover all such variations and modifications that come within the true spirit and scope of the invention.

What is claimed is:

1. A surgical tracker, said tracker comprising:
   a housing, said housing having a surface area of 180 cm$^2$ or less and a maximum depth of 8 cm so that said housing can be placed against skin that extends over body tissue which is to be tracked;
   at least one first navigation system component mounted to said housing for receiving or transmitting signals from or to a static navigation unit remote from said housing so that the position of said housing relative to the static navigation unit can be determined wherein, the signals exchanged by said at least one first navigation system component are signals other than electromagnetic or radiofrequency signals and there is no wired connection by that at least one first navigation system component and the static navigation unit;
   at least one second navigation system component mounted to said housing for transmitting electromagnetic or radio frequency signals to or receiving electromagnetic or radio frequency signals from the body tissue adjacent said housing;
   a marker separate from said housing, said marker dimensioned to be implanted subcutaneously, said marker including: a stem dimensioned to be embedded in the body tissue so as to hold said marker in a static state in the body tissue; and at least one marker navigation component that receives electromagnetic or radio frequency signals from or transmits electromagnetic or radio frequency signals to said second navigation system component in said housing so that, based on exchanged signals, the position of said marker relative to said housing can be determined wherein, said at least one second navigation system component and said at least one marker navigation component are spaced apart a maximum distance of 25 cm so that the said at least one of said at least one second navigation system component or said at least one marker navigation component that transmits signals transmits signals at a power level of 1.67 Watts or less;
   a cable that extends from said housing into the body tissue to said marker over which signals are transmitted between said housing and said marker at least one navigation system component;
   a data transmitter attached to said housing and connected to said at least one second navigation system component or, through said cable, to said at least one marker navigation system component, said data transmitter configured to wirelessly transmit to a processor remote from said housing signals based on the transmission of signals between said at least one second navigation system component and said at least one marker navigation component so that the processor, which also receives the exchanges signals between the static navigation unit and said first navigation system component, based on the exchanged signals between the static navigation unit and said at least one first navigation system component and the exchanged signals between said at least one second navigation system component and said at least one marker navigation component, can determine the position of said marker relative to the static navigation unit; and
   a battery disposed in said housing for powering said at least one first navigation system component, said at least one second navigation system component or said marker navigation component and said data transmitter.

2. The surgical tracker of claim 1, further including a coupling assembly for releasably holding said cable to said housing.

3. The surgical tracker of claim 1, wherein the at least one first navigation system component of said housing transmits or receives one from the following types of energy: light energy; sonic energy; and ultrasonic energy.

4. The surgical tracker of claim 1, wherein:
   said at least one second navigation system component in said housing is a transmitter; and
   a current source is disposed in said housing for applying signals to said second navigation system transmitter for transmission by said second navigation system transmitter and said current source is a variable current source able to apply signals of varying strength to said second navigation system transmitter wherein the maximum power of the signal output by said current source is 1.67 Watts.

5. The surgical tracker of claim 1, wherein:
   said at least one marker navigation component is configured to receive electromagnetic or radio frequency signals transmitted by said at last one second navigation system component of said housing;
   the signals received by said at least one marker navigation component are transmitted from said marker to said housing over said cable;
   an analog to digital converter disposed in said housing converts the signals received by said at least one marker navigation component into digital signals and forwards the digitized signals to said transmitter; and
   said transmitter transmits the digitized signals received from said at least one marker navigation component to the remote processor.

6. The surgical tracker of claim 5, further including a variable gain amplifier disposed in said housing that selectively amplifies the signals received by said at least one marker navigation component.

7. The surgical tracker of claim 1, wherein said housing includes first and second sets of the second navigation components, both said sets of said second navigation components capable of either transmitting signals to or receiving signals from the said at least one marker navigation system component wherein, said first and second sets of second navigation components each have at least one component capable of transmitting signals to or receiving signals from the said at least one marker navigation component and are spaced apart from each other.

8. The surgical tracker of claim 1, wherein:
a plurality of coils are mounted in said housing or in said marker, said plurality of coils functioning as a plurality of said housing second navigation system components that transmit electromagnetic or radio frequencies signals; and
a current source is mounted to said housing for supplying the signals that are transmitted by said coils, wherein said current source is able to supply power to said coils so that said coils can simultaneously transmit signals and each said coil transmits a signal at a power level of 1.67 Watts or less.

9. The surgical tracker of claim 8, wherein there are three said coils mounted in said housing or in said marker that transmit electromagnetic or radio frequency signals.

10. The surgical tracker of claim 1, wherein said data transmitter is able to wirelessly receive signals from and transmit signals to the remote processor and said signal exchange is by the exchange of light signals.

11. A surgical tracker and marker assembly, said assembly including:
a housing, said housing having a surface area of 180 cm$^2$ or less and a maximum depth of 8 cm so that said housing can be placed against skin that extends over body tissue which is to be tracked;
at least one navigation system component mounted to said housing for receiving signals from or transmitting signals to a static navigation unit remote from said housing so that the position of said housing relative the static navigation unit can be determined wherein, said at least one navigation system component receives or transmits signals other than electromagnetic or radio frequency signals and there is no wired connection between said at least one navigation system component and the static navigation unit;
a first coil assembly disposed in said housing, said first coil assembly having at least one coil;
a second coil assembly disposed in said housing, said second coil assembly having at least one coil and being separate from said first coil assembly and spaced from said first coil assembly;
at least one current source disposed in said housing that is connected to said first and second coil assemblies, said current source able to output an AC signal that, when applied to either one of said coil assemblies causes said coil assembly to output an electromagnetic or radiofrequency signals into adjacent body tissue wherein, the signal output by said at least one current source to a single coil of either said coil assembly has a maximum power level of 1.67 Watts;
a control circuit internal to said housing, said control circuit configured to regulate which one of said first or second coil assemblies outputs the electromagnetic or radiofrequency signals so that each one of said first or second coil assemblies is the only coil assembly that outputs the electromagnetic or radiofrequency signals;
a data transmitter disposed in said housing, said data transmitter able to wirelessly transmit signals to a receiver to which a processor remote from said housing is connected;
a battery disposed in said housing for powering said at least one navigation system component, said coil assemblies, said control circuit and said data transmitter;
a marker separate from said housing, said marker dimensioned to be implanted subcutaneously, said marker including: a stem dimensioned to be embedded in the body tissue so as to hold said marker in a static state to the body tissue; and at least one transducer attached to said stem, said transducer being located a maximum distance of 25 cm from said housing coil assemblies so that said transducer can receive and be sensitive to the signals transmitted by said coil assemblies and that generates a signals based on the sensed signals, wherein said transducer is connected to said housing data transmitter, and said housing data transmitter is able to transmit through the receiver to the remote processor the signals generated by said marker transducer so that the remote processor, which receives signals exchanged between the static navigation unit and the housing at least one navigation system component, based on the exchanged signals between the static navigation unit and said housing at least one navigation system component and the signals generated by said marker transducer, can determine the position of said marker relative to the static navigation unit.

12. The surgical tracker and marker assembly of claim 11, further including a cable that extends between said marker and said housing over which the signals output by said at least one marker transducer are forwarded to said housing data transmitter.

13. The surgical tracker and marker assembly of claim 11, wherein:
each said coil assembly includes a plurality of coils; and
said at least one current source is configured to simultaneously source current to said plural coils so that the plural coils of each said coil assembly are able to simultaneously output signals.

14. The surgical tracker and marker assembly of claim 11, wherein:
plural said current sources are disposed in said housing, wherein a first set of current sources output AC signals to said first coil assembly and a second set of current sources output AC signals to said second coil assembly; and
said housing control circuit is connected to said current sources for actuating said current sources, so as to, by selective actuation of said current sources, control which one of said coil assemblies outputs the electromagnetic or radio frequency signals.

15. The surgical tracker and marker assembly of claim 11, wherein:
a multiplexer is connected between, at a first end, said at least one current source and, at a second end, both said first and second coil assemblies, said multiplexer configured to selectively connect said at least one current source to either of said coil assemblies; and
said control circuit is connected to said multiplexer for determining to which one of said coil assemblies said at least one current source is connected.

16. The surgical tracker of claim 11, wherein said at least one navigation system component transmits photonic signals.

17. A surgical tracker and marker assembly, said assembly including:
- a housing, said housing having a surface area of 180 cm² or less so that said housing can be placed against skin that extends over body tissue which is to be tracked;
- at least one navigation system component mounted to said housing for receiving signals from or transmitting signals to a localizer remote from said housing so that the position of said housing relative to the localizer can be determined wherein the signals received by or transmitted from said at least one navigation system component are signals other than electromagnetic or radiofrequency signals;
- a coil assembly disposed in said housing, said coil assembly having at least one coil;
- at least one bi-polar current source disposed in said housing that is connected to said coil assembly, said current source able to output an AC signal that, when applied to said coil assembly causes said coil assembly to output an electromagnetic or radiofrequency signals into adjacent body tissue;
- a data transmitter disposed in said housing, said transmitter able to wirelessly transmit signals to a receiver to which a processor remote from said housing is connected;
- a battery disposed in said housing that powers said at least one navigation system component, said at least one current source and said data transmitter; and
- a marker separate from said housing, said marker dimensioned to be implanted subcutaneously, said marker including: a stem dimensioned to be embedded in the body tissue so as to hold said marker in a static state to the body tissue; and at least one transducer attached to said stem, said transducer being sensitive to the signals transmitted by said coil assembly and that generates signals based on the sensed signals, wherein said transducer is spaced a maximum distance of 25 cm from said coil assembly so that the signal output by said at least one coil of said coil assembly has a maximum power of 1.67 Watts and said transducer is connected to said housing data transmitter, and said housing data transmitter is able to transmit to through the receiver to the remote processor the signals generated by said marker transducer so that the remote processor, based on the exchange of signals between the localizer and said housing at least one navigation system component and the signals generated by said marker transducer, can determine the position of said marker relative to the localizer.

18. The surgical tracker and marker of claim 17, wherein:
said coil assembly includes a plurality of coils; and
a plurality of said current sources are disposed in said housing, said current sources being connected to different said coils and each said current source being able to independently controllable to output a select current so that, collectively, said plural coils are able to simultaneously output signals at different current levels.

19. The surgical tracker and marker assembly of claim 17, further including a cable that extends between said marker and said housing over which the signals output by said at least one marker transducer are forwarded to said housing transmitter.

20. The surgical tracker of claim 17, wherein said at least one navigation system component transmits photonic signals.

* * * * *